United States Patent
Chen et al.

(10) Patent No.: US 10,596,163 B2
(45) Date of Patent: *Mar. 24, 2020

(54) AZA-ARYL 1H-PYRAZOL-1-YL BENZENE SULFONAMIDES

(71) Applicant: ChemoCentryX, Inc., Mountain View, CA (US)

(72) Inventors: Xi Chen, E. Palo Alto, CA (US); Junfa Fan, Foster City, CA (US); Pingchen Fan, Fremont, CA (US); Antoni Krasinski, San Jose, CA (US); Lianfa Li, San Jose, CA (US); Rebecca M. Lui, Santa Clara, CA (US); Jeffrey P. McMahon, San Francisco, CA (US); Jay P. Powers, Pacifica, CA (US); Yibin Zeng, Foster City, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,752

(22) Filed: Oct. 25, 2018

(65) Prior Publication Data

US 2019/0060304 A1    Feb. 28, 2019

Related U.S. Application Data

(63) Continuation of application No. 14/541,637, filed on Nov. 14, 2014, now Pat. No. 10,137,120, which is a continuation of application No. 13/781,412, filed on Feb. 28, 2013, now Pat. No. 8,916,601.

(60) Provisional application No. 61/604,998, filed on Feb. 29, 2012.

(51) Int. Cl.

| | |
|---|---|
| A61K 31/4709 | (2006.01) |
| C07D 405/14 | (2006.01) |
| C07D 401/10 | (2006.01) |
| A61K 45/06 | (2006.01) |
| C07D 403/10 | (2006.01) |
| A61K 31/517 | (2006.01) |
| C07D 231/42 | (2006.01) |
| A61K 31/415 | (2006.01) |
| A61K 31/502 | (2006.01) |
| A61K 31/5377 | (2006.01) |
| C07D 401/04 | (2006.01) |
| A61K 31/4725 | (2006.01) |
| C07D 401/06 | (2006.01) |
| C07D 403/04 | (2006.01) |

(52) U.S. Cl.
CPC ........ *A61K 31/4709* (2013.01); *A61K 31/415* (2013.01); *A61K 31/4725* (2013.01); *A61K 31/502* (2013.01); *A61K 31/517* (2013.01); *A61K 31/5377* (2013.01); *A61K 45/06* (2013.01); *C07D 231/42* (2013.01); *C07D 401/04* (2013.01); *C07D 401/06* (2013.01); *C07D 401/10* (2013.01); *C07D 403/04* (2013.01); *C07D 403/10* (2013.01); *C07D 405/14* (2013.01)

(58) Field of Classification Search
None
See application file for complete search history.

(56) References Cited

U.S. PATENT DOCUMENTS

| | | |
|---|---|---|
| 8,916,601 B2 | 12/2014 | Chen et al. |
| 2009/0005410 A1 | 1/2009 | Charvat et al. |
| 2010/0075963 A1 | 3/2010 | Lehr et al. |
| 2011/0130426 A1 | 6/2011 | Bladh et al. |

FOREIGN PATENT DOCUMENTS

| | | |
|---|---|---|
| CN | 101855206 A | 10/2010 |
| WO | WO 2002/000651 A2 | 1/2002 |
| WO | WO 2003/099773 A1 | 12/2003 |
| WO | WO 2004/046092 A2 | 6/2004 |
| WO | WO 2004/058736 A1 | 7/2004 |
| WO | WO 2004/108692 A1 | 12/2004 |
| WO | WO 2005/113513 A2 | 12/2005 |
| WO | WO 2008/008374 A2 | 1/2008 |
| WO | WO 2009/038847 A1 | 3/2009 |
| WO | WO 2012/064715 A1 | 5/2012 |

OTHER PUBLICATIONS

Babu et al., *Journal of Infectious Diseases*, 191:1018-26 (2005).
Campbell et al., *J. Exp. Med.*, 195(1):135-141 (2002).
CAS RN 1177125-28-8; STN entry date: Aug. 28, 20092,3-Dihydro-N-[1-(8-methoxy-4-methyl-2-quinolinyl)-3-methyl-1H-pyrazol-5-yl]-2-oxo-6-benzoxazolesulfonamide, 2009 (1 page).
Database Chemcats, Chemical Abstracts Service, XP002694860, Columbus, Ohio, US, 7 pages (Jan. 1, 2013).
Diamond et al., *Am. J. Physiol.*, 266:F926-33 (1994).
Eddy & Giachelli, *Kidney Int.*, 47:1546-57 (1995).
Eksteen et al., "Hepatic Endothelial CCL25 Mediates the Recruitment of CCR9+ Gut-homing Lymphocytes to the Liver in Primary Sclerosing Cholangitis," *The Journal of Experimental Medicine*, 200(11):1511-1517 (Dec. 6, 2004).

(Continued)

*Primary Examiner* — Jeffrey S Lundgren
*Assistant Examiner* — Stephanie K Springer
(74) *Attorney, Agent, or Firm* — Barnes & Thornburg LLP; Ryan L. Marshall; Jonathan Hartley

(57) ABSTRACT

Compounds are provided that act as potent antagonists of the CCR(9) receptor. Animal testing demonstrates that these compounds are useful for treating inflammation, a hallmark disease for CCR(9). The compounds are generally aryl sulfonamide derivatives and are useful in pharmaceutical compositions, methods for the treatment of CCR(9)-mediated diseases, and as controls in assays for the identification of CCR(9) antagonists.

19 Claims, No Drawings

(56) References Cited

OTHER PUBLICATIONS

Engel et al., "T Helper Type 1 Memory Cells Disseminate Postoperative Ileus Over the Entire Intestinal Tract," *Nature Medicine*, 16(12):1407-1414 (Dec. 2010).
Gonzalez-Cuadrado et al., *Clin. Exp. Immunol.*, 106:518-22 (1996).
International Search Report and Written Opinion for Application No. PCT/US2013/028328, 14 pages (dated Apr. 25, 2013).
Kontoyiannis et al., *J. Exp. Med.*, 196(12):1563-1574 (Dec. 16, 2002).
Kunkel et al., *J. Exp. Med.*, 192(5):761-768 (2000).
Lloyd et al., *J. Exp. Med.*, 185:1371-80 (1997).
Morii et al., *J. Diabetes Complications*, 17:11-5 (2003).
Notice of Acceptance for related Australian Application No. 2013225938, dated Jul. 31, 2017 (3 pages).
Papadakis et al., *Gastroenterology*, 121(2):246-254 (2001).
Papadakis et al., *J. Immunol.*, 165(9):5069-5076 (2000).
Registry(STN) [online], 2009 (searched on: Aug. 25, 2016), CAS Registry No. 1177996-59-6; 1177981-13-3; 1177948-38-7; 1177920-00-1; 1177898-89-3; 1177808-74-0; 1177743-40-6; 1177735-96-4; 1177679-16-1; 1177643-05-8 (5 pages).
Rivera-Nieves et al., *Gastroenterology*, 131(5):1518-29 (Nov. 2006).
Schall et al., *Curr. Opin. Immunol.*, 6:865-873 (1994).
Schall, *Cytokine*, 3:165-183 (1991).
Segerer et al., *J. Am. Soc. Nephrol.*, 11:152-76 (2000).
Uehara et al., *J. Immunol*, 168(6):2811-2819 (2002).
Wurbel et al., *Blood*, 98(9):2626-2632 (2001).
Zaballos et al., *J. Immunol.*, 162(10):5671-5675 (1999).

AZA-ARYL 1H-PYRAZOL-1-YL BENZENE SULFONAMIDES

REFERENCE TO EARLIER FILED APPLICATIONS

The present application is a continuation of U.S. patent application Ser. No. 14/541,637, filed Nov. 14, 2014, which is a continuation of U.S. patent application Ser. No. 13/781,412, filed Feb. 28, 2013, which claims the benefit under 35 U.S.C. § 119(e) of U.S. Provisional Patent Application No. 61/604,998, filed Feb. 29, 2012, and titled "AZA-ARYL 1H-PYRAZOL-1-7L ENZENE SULFONAMIDES," which are incorporated, in their entirety, by this reference.

BACKGROUND

The present invention provides compounds and pharmaceutical compositions containing one or more of those compounds or their pharmaceutically acceptable salts, that are effective in inhibiting the binding or function of various chemokines to chemokine receptors. As antagonists or modulators of chemokine receptors, the compounds and compositions have utility in treating various immune disorder conditions and diseases.

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, Cytokine, 3:165-183 (1991), Schall et al., Curr. Opin. Immunol., 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., J. Am. Soc. Nephrol., 11:152-76 (2000); Morii et al., J. Diabetes Complications, 17:11-5 (2003); Lloyd et al. J. Exp. Med., 185:1371-80 (1997); Gonzalez-Cuadrado et al. Clin. Exp. Immunol., 106:518-22 (1996); Eddy & Giachelli, Kidney Int., 47:1546-57 (1995); Diamond et al., Am. J. Physiol., 266:F926-33 (1994)).

Tlymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor-9 (CCR(9)) has been noted to be expressed on gut-homing T cells in peripheral blood, elevated in patients with small bowel inflammation such as Crohn's disease and celiac disease. The only CCR(9) ligand identified to date, TECK (thymus-expressed chemokine) is expressed in both the small and large intestines and the ligand receptor pair is now thought to play a pivotal role in the development of IBD. In particular, this pair mediates the migration of disease causing inflammatory cells to the intestine. See for example, Zaballos et al., J. Immunol., 162(10):5671-5675 (1999); Kunkel et al., J. Exp. Med., 192(5):761-768 (2000); Papadakis et al., J. Immunol., 165(9):5069-5076 (2000); Papadakis et al., Gastroenterology, 121(2):246-254 (2001); Campbell et al., J. Exp. Med., 195(1):135-141 (2002); Wurbel et al., Blood, 98(9):2626-2632 (2001); and Uehara et al., J. Immunol, 168(6):2811-2819 (2002); Rivera-Nieves et al., Gastroenterology, 2006 November; 131(5):1518-29; and Kontoyiannis et al., J. Exp. Med., Vol. 196, Number 12, Dec. 16, 2002. In addition CCR(9) bearing lymphocytes have been show to mediate the pathology of filariasis (lymphatic filarial disease) and inhibition of CCR(9) has been correlated with reduction of the pathology associated with such conditions. See for example Babu et al., Journal of Infectious Diseases, 191: 1018-26, 2005.

The identification of compounds that modulate the function of CCR(9) represents an attractive new family of therapeutic agents for the treatment of inflammatory and other conditions and diseases associated with CCR(9) activation, such as inflammatory bowel disease.

US 2011/0130426 discloses compounds of formula I and their use in medical therapy such as modulating the glucocorticoid receptor in warm blooded animals:

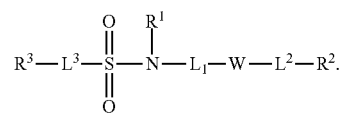

WO 02/00651 discloses compounds of formula (Ia) as inhibitors of trypsin-like serine protease enzymes, and methods of using the same as anti-coagulant agents for treatment and prevention of thromboembolic disorders:

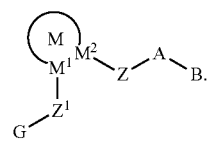

(Ia)

BRIEF SUMMARY

The present invention is directed to compounds and pharmaceutically acceptable salts thereof, compositions, and methods useful in modulating chemokine activity and chemokine receptor activity. The compounds and salts thereof, compositions, and methods described herein are useful in treating or preventing chemokine-mediated conditions or diseases, including certain inflammatory and immunoregulatory disorders and diseases.

The compounds of the present invention have been shown to modulate one or more of CCR1, CCR2, CCR3, CCR4, CCR5, CCR6, CCR7, CCR8, CCR(9), CCR10, CCR11, CCR12, CXCR1, CXCR2, CXCR3, CXCR4, CXCR5, CXCR6, CXCR7, CX3CR1, C5aR, chemR23, FPRL1, FPR1, and FPRL2. In particular, various compounds of the present invention modulate CCR(9) as shown in the examples.

In one embodiment, the present compounds may be represented by formula (I) or salts thereof:

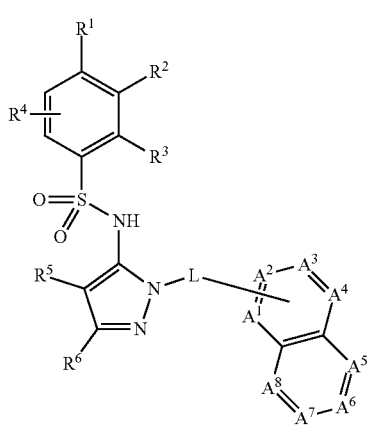

(I)

where $R^1$, $R^2$, $R^3$, $R^4$, $R^5$, $R^6$, L, $A^1$, $A^2$, $A^3$, $A^4$, $A^5$, $A^6$, $A^7$, and $A^8$ are as defined below.

In another aspect, the present invention provides compositions useful in modulating chemokine activity. In one embodiment, a composition according to the present invention comprises a compound according to the invention and a pharmaceutically acceptable carrier or excipient.

In yet another aspect, the present invention provides methods of modulating chemokine function in a cell, comprising contacting the cell with a therapeutically effective amount of a compound or composition according to the invention.

In still another aspect, the present invention provides methods for modulating chemokine function, comprising contacting a chemokine receptor with a therapeutically effective amount of a compound or composition according to the invention.

In still another aspect, the present invention provides methods for treating a chemokine-mediated condition or disease, comprising administering to a subject a safe and effective amount of a compound or composition according to the invention. The administering may be oral, parenteral, rectal, transdermal, sublingual, nasal or topical. In some aspects the compound may be administered in combination with an anti-inflammatory or analgesic agent.

In addition to the compounds provided herein, the present invention further provides pharmaceutical compositions containing one or more of these compounds, as well as methods for the use of these compounds in therapeutic methods, primarily to treat diseases associated with chemokine signaling activity. The CCR(9) mediated disease or condition is inflammatory bowel diseases, an allergic disease, psoriasis, atopic dermatitis, asthma, fibrotic diseases, graft rejection, immune mediated food allergies, autoimmune diseases, Celiac disease, rheumatoid arthritis, thymoma, thymic carcinoma, leukemia, solid tumor, acute lymphocytic leukemia, melanoma, primary sclerosing cholangitis, hepatitis, inflammatory hepatic disease, or postoperative ileus.

DETAILED DESCRIPTION

General

The present invention is directed to compounds and salts thereof, compositions and methods useful in the modulation of chemokine receptor function, particularly CCR(9) function. Modulation of chemokine receptor activity, as used herein in its various forms, is intended to encompass antagonism, agonism, partial antagonism, inverse agonism and/or partial agonism of the activity associated with a particular chemokine receptor, preferably the CCR(9) receptor. Accordingly, the compounds of the present invention are compounds which modulate at least one function or characteristic of mammalian CCR(9), for example, a human CCR(9) protein. The ability of a compound to modulate the function of CCR(9), can be demonstrated in a binding assay (e.g., ligand binding or agonist binding), a chemotaxis (migration assay), a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

The term "alkyl" by itself or as part of another substituent refers to a hydrocarbon group which may be linear, cyclic, or branched or a combination thereof having the number of carbon atoms designated (i.e., $C_{1-8}$ means one to eight carbon atoms). The term "cycloalkyl" by itself or as a part of another substituent refers to a cyclic alkyl group having the number of carbons designated and is a subset of the term "alkyl." Other subsets of the term "alkyl" include "linear" and "branched" alkyl groups which refer to two different types of acyclic alkyl groups. Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. In this list of examples, the methyl, ethyl, n-propyl, and n-butyl alkyl examples are also examples of "linear alkyl" groups. Similarly, isopropyl and t-butyl are also examples of "branched alkyl" groups. Cyclopentyl, cyclohexyl, (cyclohexyl)methyl, cyclopropylmethyl, bicyclo[2.2.1]heptane, bicyclo[2.2.2]octane are examples of "cycloalkyl" groups. In some embodiments, cyclopropyl may be used as a bridging group between two other moieties and represented as —CH(CH$_2$)CH—. Alkyl groups can be substituted or unsubstituted, unless otherwise indicated. Examples of substituted alkyl include haloalkyl, thioalkyl, aminoalkyl, and the like. Additional examples of suitable substitutions of alkyl include, but are not limited to, hydroxy-isopropyl, —C(CH$_3$)$_2$—OH, aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl.

"Alkoxy" refers to —O-alkyl. Examples of an alkoxy group include methoxy, ethoxy, n-propoxy etc. The alkyl portion of alkoxy may be alkyl of from 1 to 16 carbons, and in some embodiments of from 1 to 8 carbons.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Alkylamino" refers to —N(alkyl)$_2$ or —NH(alkyl). When the alkylamino group contains two alkyl groups, the alkyl groups may be combined together to form a carbocyclic or heterocylic ring. It is to be understood that the alkyl groups of the alkylamino group may be substituted or unsubstituted. Examples of an alkylamino group include methylamino, tert-butylamino, dimethylamino, di-isopropylamino, morpholino, and the like.

"Aminoalkyl", as a substituted alkyl group, refers to a monoaminoalkyl or polyaminoalkyl group, most typically substituted with from 1-2 amino groups. Examples include aminomethyl, 2-aminoethyl, 2-diethylaminoethyl, and the like.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated. Substituted aryl may be substituted with one or more substituents. Suitable substituents for aryl include substituted or unsubstituted $C_{1-8}$ alkyl and those substituents as discussed above for substituted alkyl.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms with the caveat that at least one heteroatom is present. In some embodiments, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In the definitions above, suitable substituents for substituted alkyl, alkeynyl, and alkynyl include: halogen, —CN, —CO2R', —C(O)R', —C(O)NR'R", oxo (═O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'—C(NHR")═NR''', —SiR'R"R''', —OSiR'R"R''', —N$_3$, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical. With respect to substituted alkyl, R', R" and R''' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6-, or 7-membered ring.

In one preferred embodiment, heterocyclic groups may be represented by formula (AA) below:

AA where formula (AA) is attached via a free valence on either $M^1$ or $M^2$; $M^1$ represents O, NR$^e$, or S(O)$_i$; $M^2$ represents CR$^f$R$^g$, O, S(O)$_i$, or NR$^e$; where it may be necessary to omit one R$^f$, R$^g$, or R$^e$ to create a free valence on $M^1$ or $M^2$ such as, for example CR$^f$, CR$^g$, or N; l is 0, 1 or 2; j is 1, 2 or 3 and k is 1, 2 or 3, with the proviso that j+k is 3, 4, or 5; and R$^a$, R$^b$, R$^c$, R$^d$, R$^e$, R$^f$, and R$^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —COR$^h$, —CO$_2$R$^h$, —CONR$^h$R$^i$, —NR$^h$COR$^i$, —SO$_2$R$^h$, —SO$_2$NR$^h$R$^i$, —NR$^h$SO$_2$R$^i$, —NR$^h$R$^i$, —OR$^h$, —SiR$^h$R$^i$R$^j$, —OSiR$^h$R$^i$R$^j$, -Q$^1$COR$^h$, -Q$^1$CO$_2$R$^h$, -Q$^1$CONR$^h$R$^i$, -Q$^1$NR$^h$COR$^i$, -Q$^1$SO$_2$R$^h$, -Q$^1$SO$_2$NR$^h$R$^i$, -Q$^1$NR$^h$SO$_2$R$^i$, -Q$^1$NR$^h$R$^i$, -Q$^1$OR$^h$, wherein Q$^1$ is a member selected from the group consisting of $C_{1-4}$ alkylene, $C_{2-4}$ alkenylene and $C_{2-4}$ alkynylene, and R$^h$, R$^i$ and R$^j$ are independently selected from the group consisting of hydrogen and $C_{1-8}$ alkyl, and wherein the aliphatic portions of each of the R$^a$, R$^b$, R$^c$, R$^d$, R$^e$, R$^f$, R$^g$, R$^h$, R$^i$ and R$^j$ substituents are optionally substituted with from one to three members selected from the group consisting of halogen, —OH, —OR'', —OC(O)NHR'', —OC(O)NR''R$^o$, —SH, —SR'', —S(O)R'', —S(O)$_2$R'', —SO$_2$NH$_2$, —S(O)$_2$NHR'', —S(O)$_2$NR''R$^o$, —NHS(O)$_2$R'', —NR''S(O)$_2$R$^o$, —C(O)

$NH_2$, —C(O)NHR″, —C(O)NR″R°, —C(O)R″, —NHC(O)R°, —NR″C(O)R°, —NHC(O)NH_2, —NR″C(O)NH_2, —NR″C(O)NHR°, —NHC(O)NHR″, —NR″C(O)NR°R^p, —NHC(O)NR″R°, —CO_2H, —CO_2R″, —NHCO_2R″, —NR″CO_2R°, —CN, —NO_2, —NH_2, —NHR″, —NR″R°, —NR″S(O)NH_2 and —NR″S(O)_2NHR°, wherein R″, R° and R^p are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In another preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —COR^h, —CO_2R^h, —CONR^hR^i, —NR^hCOR^h, —SO_2R^h, —SO_2NR^hR^i, —NSO_2R^hR^i, —NR^hR^i, and —OR^h, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, —OH, —OR″, —OC(O)NHR″, —OC(O)NR″R°, —SH, —SR″, —S(O)R°, —S(O)_2R″, —SO_2NH_2, —S(O)_2NHR°, —S(O)_2NR″R°, —NHS(O)_2R″, —NR″S(O)_2R°, —C(O)NH_2, —C(O)NHR″, —C(O)NR″R®, —C(O)R″, —NHC(O)R″, —NR″C(O)R°, —NHC(O)NH_2, —NR″C(O)NH_2, —NR″C(O)NHR°, —NHC(O)NHR″, —NR″C(O)NR°R^p, —NHC(O)NR″R°, —CO_2H, —CO_2R″, —NHCO_2R″, —NR″CO_2R°, —CN, —NO_2, —NH_2, —NHR″, —NR″R°, —NR″S(O)NH_2, and —NR″S(O)_2NHR°, wherein R″, R° and R^p are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms.

More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or —O⁻), the resulting group may have either a carbonyl (—C(O)—) or a N-oxide (—N⁺—O⁻).

Suitable substituents for substituted alkyl, substituted alkenyl, and substituted alkynyl include halogen, —CN, —CO_2R', —C(O)R', —C(O)NR'R", oxo (=O or —O⁻), —OR', —OSiR'R"R'", —OC(O)R', —OC(O)NR'R"—NO_2, —NR'C(O)R", —NR'"C(O)NR'R", —NR'R", —NR'CO_2R", —NR'S(O)R", —NR'S(O)_2R'", —NR'"S(O)NR'R", —NR'"S(O)_2NR'R", —SR', —S(O)R', —S(O)_2R', —S(O)_2NR'R", —NR'—C(NHR")=NR'", —SiR'R"R'", —N_3, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO_2R', —C(O)R', —C(O)NR'R", oxo (=O or —O⁻), —OR', —OSiR'R"R'", —OC(O)R', —OC(O)NR'R", —NO_2, —NR'C(O)R", —NR'"C(O)NR'R", —NR'R", —NR'CO_2R", —NR'S(O)R", —NR'S(O)_2R", —NR'"S(O)NR'R", —NR'"S(O)_2NR'R", —SR', —S(O)R', —S(O)_2R', —S(O)_2NR'R", —NR'—C(NHR")=NR'", —SiR'R"R'", —N_3, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to the total number of open valences on the aromatic ring system.

As used above, R', R" and R'" each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R'", or R' and R'" may together with the atom(s) to which they are attached, form a substituted or unsubstituted 5-, 6-, or 7-membered ring.

Two of the substituents on adjacent atoms of an aryl or heteroaryl ring may optionally be replaced with a substituent of the formula -T-C(O)—(CH_2)_q—U—, wherein T and U are independently —NR""—, —O—, —CH_2— or a single bond, and q is an integer of from 0 to 2. Alternatively, two of the substituents on adjacent atoms of the aryl or heteroaryl ring may optionally be replaced with a substituent of the formula -A'—(CH_2)_r—B'—, wherein A' and B' are independently —CH_2—, —O—, —NR""—, —S—, —S(O)—, —S(O)_2—, —S(O)_2NR""— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH_2)_s—X—(CH_2)_t—, where s and t are independently integers of from 0 to 3, and XIV is —O—, —NR""—, —S—, —S(O)—, —S(O)$_2$—, or —S(O)$_2$NR'—. R'''' in is selected from hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. In some embodiments, the compounds include a sodium addition salt.

Also included are salts of amino acids such as arginate and the like, and salts of organic acids like glucuronic or galactunoric acids and the like (see, for example, Berge, S. M. et al, "Pharmaceutical Salts", *J. Pharmaceutical Science*, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs may be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The compounds of the invention may be present in the form of pharmaceutically acceptable metabolites thereof. The term "metabolite" means a pharmaceutically acceptable form of a metabolic derivative of a compound of the invention (or a salt thereof). In some aspects, the metabolite may be a functional derivative of a compound that is readily convertible in vivo into an active compound. In other aspects, the metabolite may be an active compound.

The term "acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include: hydroxamic acids, sulfonic acids, sulfinic acids, sulfonamides, acyl-sulfonamides, phosphonic acids, phosphinic acids, phosphoric acids, tetrazole, and oxo-oxadiazoles.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms; all such tautomeric forms of the compounds being within the scope of the invention. For example, some compounds having heteroaryl may be substituted with one or more hydroxyl groups. Tautomeric forms would, therefore, include oxo substitutions. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The compounds of the present invention may include a detectable label. A detectable label is a group that is detectable at low concentrations, usually less than micromolar, probably less than nanomolar and possibly less than picomolar, and that can be readily distinguished from other molecules, due to differences in a molecular property (e.g. molecular weight, mass to charge ratio, radioactivity, redox potential, luminescence, fluorescence, electromagnetic properties, binding properties, and the like). Detectable labels may be detected by spectroscopic, photochemical, biochemical, immunochemical, electrical, magnetic, electromagnetic, optical or chemical means and the like.

A wide variety of detectable labels are within the scope of the present invention, including hapten labels (e.g. biotin, or labels used in conjunction with detectable antibodies such as horse radish peroxidase antibodies); mass tag labels (e.g. stable isotope labels); radioisotopic labels (including $^3$H, $^{125}$I, $^{35}$S, $^{14}$C, or $^{32}$P); metal chelate labels; luminescent labels including fluorescent labels (such as fluorescein, isothiocyanate, Texas red, rhodamine, green fluorescent protein, and the like), phosphorescent labels, and chemiluminescent labels, typically having quantum yield greater than 0.1; electroactive and electron transfer labels; enzyme modulator labels including coenzymes, organometallic catalysts horse radish peroxidase, alkaline phosphatase and others commonly used in an ELISA; photosensitizer labels; magnetic bead labels including Dynabeads; colorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; and carbon black labels. Patents teaching the use of such detectable labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

Detectable labels are commercially available or may be prepared as known to one skilled in the art. Detectable labels may be covalently attached to the compounds using a reactive functional group, which can be located at any appropriate position. Methods for attaching a detectable label are known to one skilled in the art. When the reactive group is attached to an alkyl, or substituted alkyl chain tethered to an aryl nucleus, the reactive group may be located at a terminal position of an alkyl chain.

Compounds

The present invention provides compounds that modulate the activity of CCR(9). Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

For example, compounds of this invention act as potent CCR(9) antagonists, and this antagonistic activity has been further confirmed in animal testing for inflammation, one of the hallmark disease states for CCR(9). Accordingly, the compounds provided herein are useful in pharmaceutical compositions, methods for the treatment of CCR(9)-mediated diseases, and as controls in assays for the identification of competitive CCR(9) antagonists.

In the formulae set forth below, when a variable appears more than once in the same formula, it can be either the same or different. For example, in formula (I), one $R^8$ can be —NH$_2$ and the remainder can be hydrogen.

In one embodiment, the compounds of the present invention are represented by formula (I), or salts thereof:

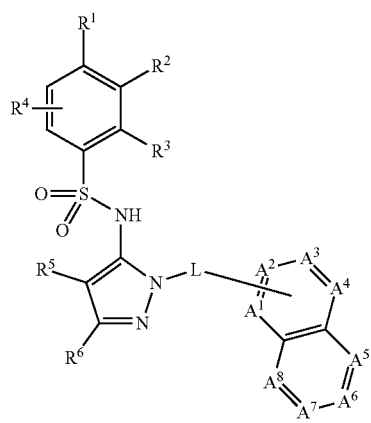
(I)

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl; $R^2$ is H, F, Cl, substituted or unsubstituted $C_{1-8}$ alkoxy; or $R^1$ and $R^2$ together with the carbon atoms to which they are attached form a non-aromatic carbocyclic ring or a heterocyclic ring; $R^3$ is H, substituted or unsubstituted $C_{1-8}$ alkyl, substituted or unsubstituted $C_{1-8}$ alkoxy, or halo; $R^4$ is H or F; $R^5$ is H, F, Cl, or —CH$_3$; $R^6$ is H, halo, —CN, —CO$_2$R$^a$, —CONH$_2$, —NH$_2$, substituted or unsubstituted $C_{1-8}$ alkyl, substituted or unsubstituted $C_{1-8}$ alkoxy, or substituted or unsubstituted $C_{1-8}$ aminoalkyl; $R^a$ is H or substituted or unsubstituted $C_{1-8}$ alkyl; where $R^5$ and $R^6$ may together form a carbocyclic ring; L is a bond or —CH$_2$—, or —CH(CH$_3$)—; each of $A^1$, $A^2$, $A^3$, $A^4$, $A^5$, $A^6$, $A^7$, and $A^8$ are independently selected from the group consisting of N, N—O, and —CR$^8$—; where at least one and not more than two of $A^1$, $A^2$, $A^3$, $A^4$, $A^5$, $A^6$, $A^7$ and $A^8$ are N or N—O; $R^8$ is each independently selected from the group consisting of H, halo, —CN, —OH, oxo, substituted or unsubstituted $C_{1-8}$ alkyl, substituted or unsubstituted $C_{1-8}$ alkoxy, and —NR$^{20}$R$^{21}$, substituted or unsubstituted aryl, substituted or unsubstituted heteroaryl, and substituted or unsubstituted heterocyclyl; and $R^{20}$ and $R^{21}$ are each independently H, or substituted or unsubstituted $C_{1-8}$ alkyl.

In one embodiment of formula (I), $R^1$ is substituted or unsubstituted $C_{2-8}$ alkyl; preferably $R^1$ is t-butyl; $R^2$, $R^3$, $R^4$ and $R^5$ are H; $R^6$ is substituted or unsubstituted $C_{1-8}$ alkyl, substituted or unsubstituted $C_{1-8}$ alkoxy, —CN, —CONH$_2$, —NH$_2$, or $C_{1-8}$ aminoalkyl; preferably $R^6$ is unsubstituted $C_{1-8}$ alkyl, or $C_{1-8}$ haloalkyl; more preferably $R^6$ is —CH$_3$, —CH$_2$F, —CHF$_2$, or —CF$_3$; L is a bond; and $A^1$, $A^2$, $A^3$, $A^4$, $A^5$, $A^6$, $A^7$, $A^8$, and $R^8$ are as defined formula (I).

In another embodiment of formula (I), $R^1$ is substituted or unsubstituted $C_{2-8}$ alkyl; preferably $R^1$ is t-butyl; $R^2$ is F; $R^3$, $R^4$ and $R^5$ are H; $R^6$ is substituted or unsubstituted $C_{1-8}$ alkyl, substituted or unsubstituted $C_{1-8}$ alkoxy, —CN, —CONH$_2$, —NH$_2$, or substituted or unsubstituted $C_{1-8}$ aminoalkyl; preferably $R^6$ is unsubstituted $C_{1-8}$ alkyl, or $C_{1-8}$ haloalkyl; more preferably $R^6$ is —CH$_3$, —CH$_2$F, —CHF$_2$, or —CF$_3$; L is a bond; and $A^1$, $A^2$, $A^3$, $A^4$, $A^5$, $A^6$, $A^7$, $A^8$, and $R^8$ are as defined formula (I).

In one embodiment, the compounds of formula (I) of the present invention are represented by formula (II), or salts thereof:

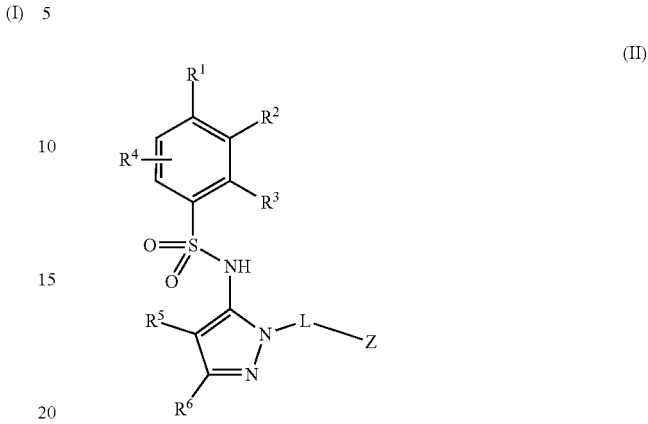
(II)

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl; $R^2$ is H, F, Cl, or substituted or unsubstituted $C_{1-8}$ alkoxy; or $R^1$ and $R^2$ together with the carbon atoms to which they are attached form a non-aromatic carbocyclic ring or a heterocyclic ring; $R^3$ is H, substituted or unsubstituted $C_{1-8}$ alkyl, substituted or unsubstituted $C_{1-8}$ alkoxy, or halo; $R^4$ is H or F; $R^5$ is H, F, Cl, or —CH$_3$; $R^6$ is H, halo, —CN, —CO$_2$R$^a$, —CONH$_2$, —NH$_2$, substituted or unsubstituted $C_{1-8}$ aminoalkyl, substituted or unsubstituted $C_{1-8}$ alkyl, or substituted or unsubstituted $C_{1-8}$ alkoxy; $R^a$ is H or substituted or unsubstituted $C_{1-8}$ alkyl; where $R^5$ and $R^6$ may together form a carbocyclic ring; L is a bond, —CH$_2$—, or —CH(CH$_3$)—; Z is selected from the group consisting of

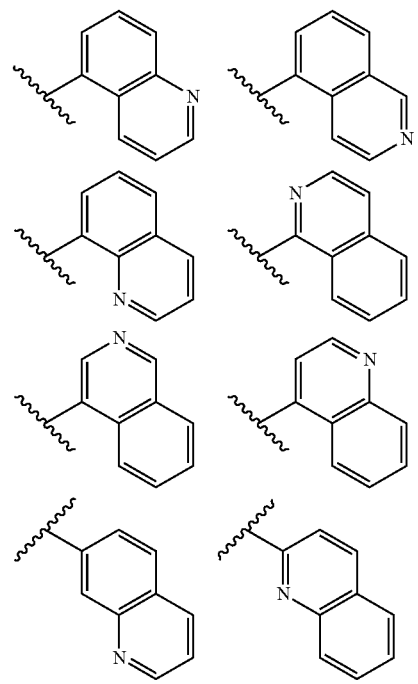

-continued

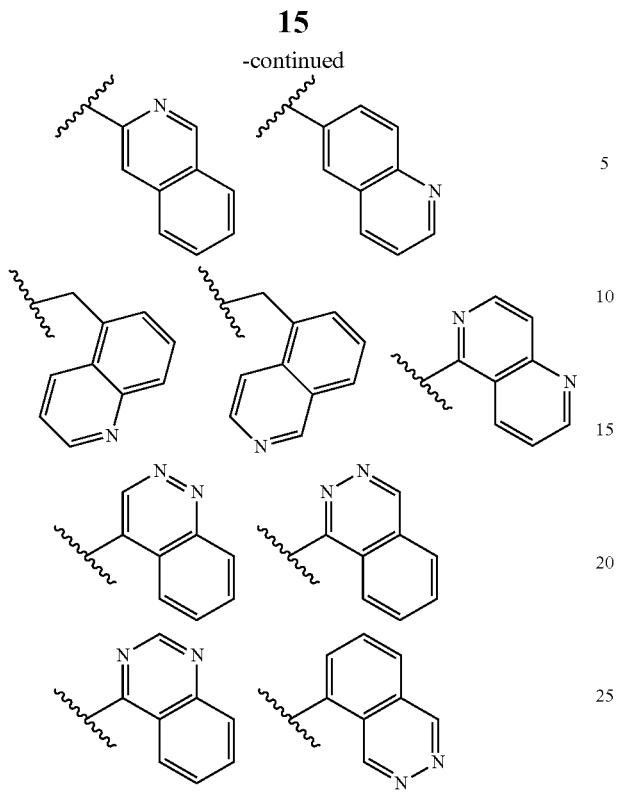

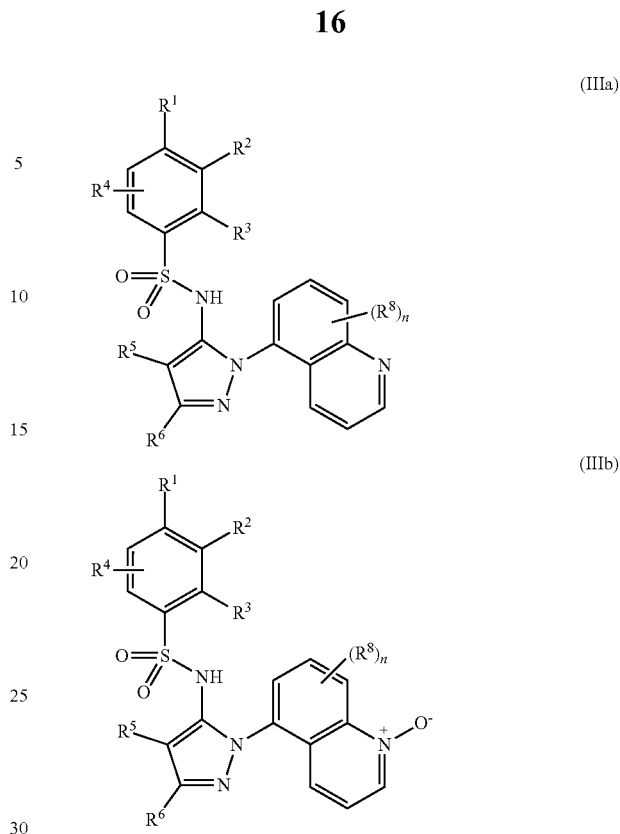

and N-oxides thereof; where the Z group may be unsubstituted or substituted with 1 to 3 independently selected $R^8$ substituents; each $R^8$ is independently selected from the group consisting of H, halo, —CN, —OH, oxo, substituted or unsubstituted $C_{1-8}$ alkyl, substituted or unsubstituted $C_{1-8}$ alkoxy, —$NR^{20}R^{21}$, substituted or unsubstituted aryl, substituted or unsubstituted heteroaryl, and substituted or unsubstituted heterocyclyl; and $R^{20}$ and $R^{21}$ are each independently H, or substituted or unsubstituted $C_{1-8}$ alkyl.

In one embodiment of formula II, Z is selected from the group consisting of: substituted or unsubstituted quinolinyl, substituted or unsubstituted isoquinolinyl, substituted or unsubstituted 1,6-naphthyridinyl, substituted or unsubstituted cinnolinyl, substituted or unsubstituted phthalazinyl, substituted or unsubstituted quinazolinyl.

In one embodiment of formula (II), $R^1$ is substituted or unsubstituted $C_{2-8}$ alkyl; preferably $R^1$ is t-butyl; $R^2$, $R^3$, $R^4$ and $R^5$ are H; and $R^6$ is substituted or unsubstituted $C_{1-8}$ alkyl, substituted or unsubstituted $C_{1-8}$ alkoxy, —CN, —$CONH_2$, —$NH_2$, or substituted or unsubstituted $C_{1-8}$ aminoalkyl; preferably $R^6$ is unsubstituted $C_{1-8}$ alkyl, or $C_{1-8}$ haloalkyl; more preferably $R^6$ is —$CH_3$, —$CH_2F$, —$CHF_2$, or —$CF_3$.

In another embodiment of formula (II), $R^1$ is substituted or unsubstituted $C_{2-8}$ alkyl; preferably $R^1$ is t-butyl; $R^2$ is F; $R^3$, $R^4$ and $R^5$ are H; and $R^6$ is substituted or unsubstituted $C_{1-8}$ alkyl, substituted or unsubstituted $C_{1-8}$ alkoxy, —CN, —$CONH_2$, —$NH_2$, or substituted or unsubstituted $C_{1-8}$ aminoalkyl; preferably $R^6$ is unsubstituted $C_{1-8}$ alkyl, or $C_{1-8}$ haloalkyl; more preferably $R^6$ is —$CH_3$, —$CH_2F$, —$CHF_2$, or —$CF_3$.

In one embodiment, the compounds of formula (I) of the present invention are represented by formula (IIIa) or (IIIb), or salts thereof:

where $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl; preferably substituted or unsubstituted $C_{2-8}$ alkyl; more preferably t-butyl; $R^2$ is H, F, Cl, or substituted or unsubstituted $C_{1-8}$ alkoxy; preferably H or F; more preferably H; or $R^1$ and $R^2$ together with the carbon atoms to which they are attached form a non-aromatic carbocyclic ring or a heterocyclic ring; $R^3$ is H, substituted or unsubstituted $C_{1-8}$ alkyl, substituted or unsubstituted $C_{1-8}$ alkoxy, or halo; preferably H or halo; more preferably H; $R^4$ is H or F; preferably H; $R^5$ is H, F, Cl, or —$CH_3$; preferably H; $R^6$ is H, halo, —CN, —$CO_2R^a$, —$CONH_2$, —$NH_2$, substituted or unsubstituted $C_{1-8}$ aminoalkyl, substituted or unsubstituted $C_{1-8}$ alkyl, or substituted or unsubstituted $C_{1-8}$ alkoxy; preferably unsubstituted $C_{1-8}$ alkyl, or $C_{1-8}$ haloalkyl; more preferably —$CH_3$, —$CH_2F$, —$CHF_2$, or —$CF_3$; $R^a$ is H or substituted or unsubstituted $C_{1-8}$ alkyl; or where $R^5$ and $R^6$ together with the carbon atoms to which they are attached form a carbocyclic ring; each $R^8$ is independently selected from the group consisting of H, halo, —CN, —OH, oxo, substituted or unsubstituted $C_{1-8}$ alkyl, substituted or unsubstituted $C_{1-8}$ alkoxy, and —$NR^{20}R^{21}$, substituted or unsubstituted aryl, substituted or unsubstituted heteroaryl, and substituted or unsubstituted heterocyclyl; $R^{20}$ and $R^{21}$ are each independently H, or substituted or unsubstituted $C_{1-8}$ alkyl; and n is 0, 1, 2, or 3.

In one embodiment of formula (IIIa) or (IIIb), $R^1$ is substituted or unsubstituted $C_{2-8}$ alkyl; preferably $R^1$ is t-butyl; $R^2$, $R^3$, $R^4$ and $R^5$ are H; $R^6$ is substituted or unsubstituted $C_{1-8}$ alkyl, substituted or unsubstituted $C_{1-8}$ alkoxy, —CN, —$CONH_2$, —$NH_2$, or substituted or unsubstituted $C_{1-8}$ aminoalkyl; preferably $R^6$ is unsubstituted $C_{1-8}$ alkyl, or $C_{1-8}$ haloalkyl; more preferably $R^6$ is —$CH_3$, —$CH_2F$, —$CHF_2$, or —$CF_3$; L is a bond; and $A^1$, $A^2$, $A^3$, $A^4$, $A^5$, $A^6$, $A^7$, $A^8$, and $R^8$ are as defined formula (I).

In one embodiment of formula (IIIa) or (IIIb), R¹ is substituted or unsubstituted C$_{2-8}$ alkyl; preferably R¹ is t-butyl; R² is F; R³, R⁴ and R⁵ are H; R⁶ is substituted or unsubstituted C$_{1-8}$ alkyl, substituted or unsubstituted C$_{1-8}$ alkoxy, —CN, —CONH$_2$, —NH$_2$, or substituted or unsubstituted C$_{1-8}$ aminoalkyl; preferably R⁶ is unsubstituted C$_{1-8}$ alkyl, or C$_{1-8}$ haloalkyl; more preferably R⁶ is —CH$_3$, —CH$_2$F, —CHF$_2$, or —CF$_3$; L is a bond; and A¹, A², A³, A⁴, A⁵, A⁶, A⁷, A⁸, and R⁸ are as defined formula (I).

In one embodiment of formula (IIIa) or (IIIb), R¹ is selected from the group consisting of —CH$_2$CH$_3$, —CH(CH$_3$)$_2$, —C(CH$_3$)$_3$, —C(CH$_3$)$_2$CH$_2$CH$_3$, C(CH$_2$CH$_2$)CN, —C(OH)(CH$_3$)$_2$, —OCH$_3$, —OCH$_2$CH$_3$, —OCH(CH$_3$)$_2$, —OC(CH$_3$)$_3$, —OCH$_2$CH(CH$_3$)$_2$, —OCF$_3$, and morpholino; preferably R¹ is —C(CH$_3$)$_3$; R² is H, F, or Cl; preferably R² is H or F; R¹ and R² may together form —OC(CH$_3$)$_2$CH$_2$— or —C(CH$_3$)$_2$CH$_2$CH$_2$—; R³ is H, —CH$_3$, or —OCH$_3$; preferably R³ is H; R⁴ is H or F; preferably R⁴ is H; R⁵ is H; R⁶ is H, —CH$_3$, —CH$_2$CH$_3$, —CH(CH$_3$)$_2$, C$_3$H$_7$, —CH$_2$F, —CHF$_2$, —CF$_2$CH$_3$, —CF$_3$, —CH$_2$OCH$_3$, —CH$_2$OH, —CH$_2$CN, —CN, or —CONH$_2$; preferably R⁶ is —CH$_3$, —CH$_2$F, —CHF$_2$, or —CF$_3$; and R⁸ is each independently selected from the group consisting of H, F, Cl, Br, —CH$_3$, —OH, —OCH$_3$, —OCH$_2$CH$_3$, —NH$_2$, —N(CH$_3$)$_2$, and —CN; preferably R⁸ is H or —NH$_2$.

In some embodiments, R² is H. In some embodiments, R² is F.

In one embodiment, the compounds of formula (IIIa) or (IIIb), or salts thereof are selected from the group consisting of:

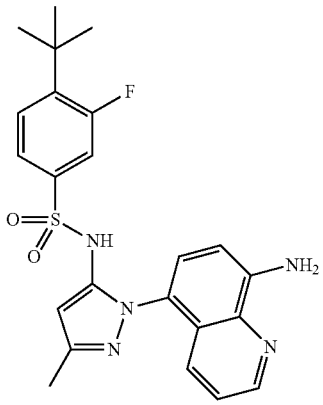

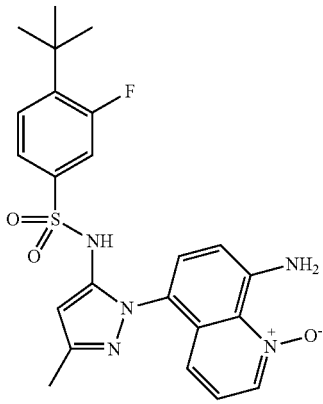

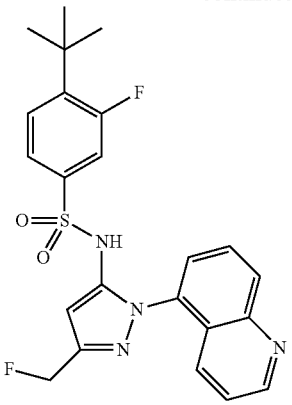

-continued

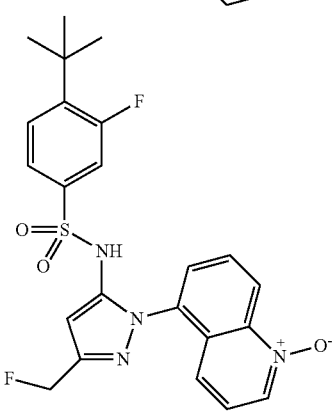

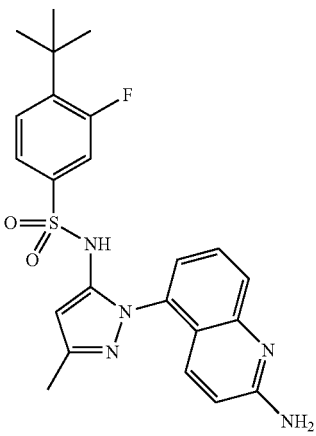

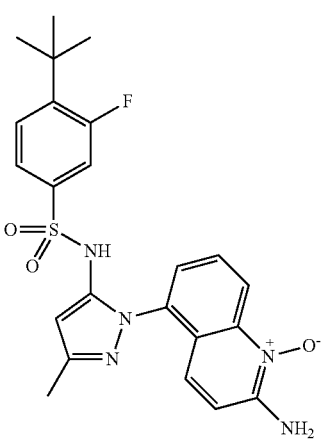

19
-continued
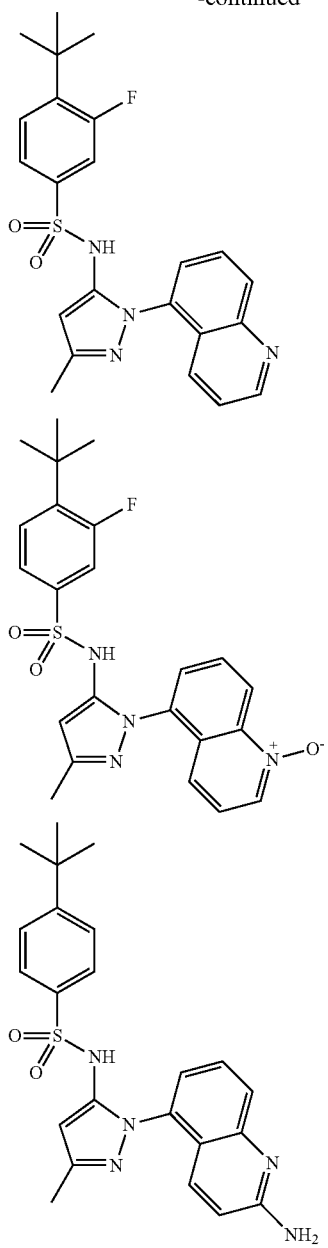
20
-continued
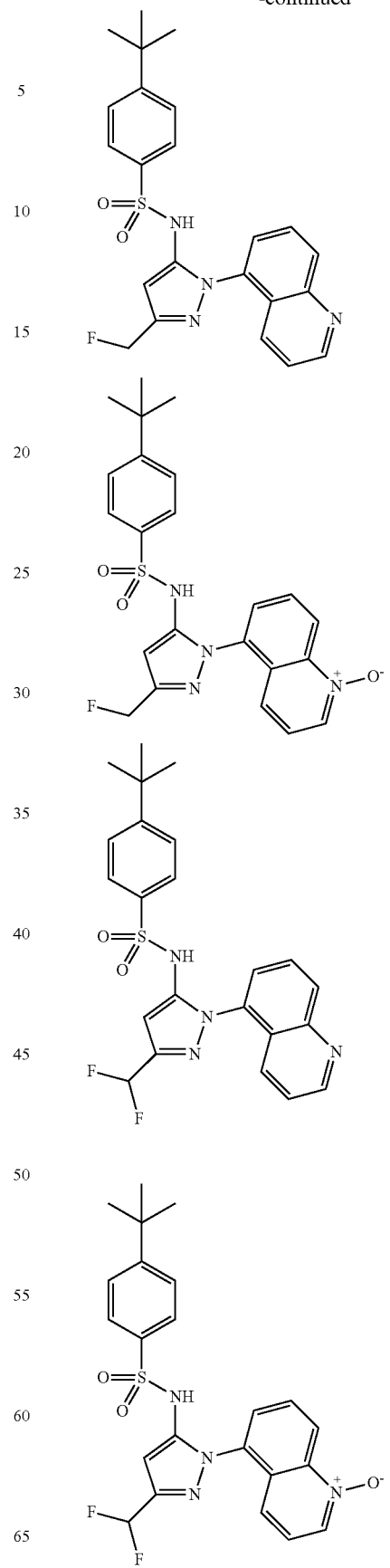

-continued

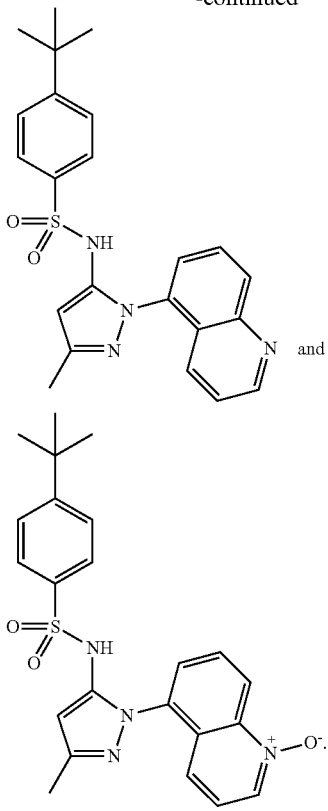

Preferred R¹ Substituents

In formulae (I, II, IIIa, and IIIb), $R^1$ is selected from the group consisting of substituted or unsubstituted $C_{2-8}$ alkyl, substituted or unsubstituted $C_{1-8}$ alkoxy, substituted or unsubstituted $C_{1-8}$ alkylamino, and substituted or unsubstituted $C_{3-10}$ heterocyclyl. When $R^1$ is substituted alkyl, the alkyl group is preferably substituted with halo or hydroxy. When $R^1$ is substituted alkoxy, the alkoxy group is preferably substituted with halo. Preferably $R^1$ is unsubstituted $C_{2-8}$ alkyl, including $C_{3-8}$ cycloalkyl, $C_{2-8}$ haloalkyl, $C_{1-8}$ hydroxyalkyl, unsubstituted $C_{1-8}$ alkoxy, $C_{1-8}$ haloalkoxy, and $C_{1-8}$ alkylamino; more preferably unsubstituted $C_{2-8}$ alkyl, $C_{2-8}$ haloalkyl, unsubstituted $C_{1-8}$ alkoxy, and $C_{1-8}$ alkylamino; even more preferably unsubstituted 02-8 alkyl, unsubstituted $C_{1-8}$ alkoxy, and morpholino; still more preferably unsubstituted $C_{2-8}$; and most preferably t-butyl.

Preferred R⁶ Substituents

In formulae (I, II, IIIa, and IIIb), $R^6$ is H, halo, —CN, —$CO_2R^a$, —$CONH_2$, —$NH_2$, substituted or unsubstituted $C_{1-8}$ alkyl, substituted or unsubstituted $C_{1-8}$ alkoxy, or substituted or unsubstituted $C_{1-8}$ aminoalkyl. When $R^6$ is substituted alkyl, the alkyl group is preferably substituted with halo, hydroxy, alkoxy, or cyano. Preferably $R^6$ is —CN, —$CONH_2$, —$NH_2$, unsubstituted $C_{1-8}$ alkyl, unsubstituted $C_{1-8}$ haloalkyl, and unsubstituted $C_{1-8}$ alkoxy; more preferably unsubstituted $C_{1-8}$ alkyl, or unsubstituted $C_{1-8}$ haloalkyl, even more preferably unsubstituted $C_{1-8}$ alkyl; most preferably methyl.

Compositions that Modulate Chemokine Activity

In another aspect, the present invention provides compositions that modulate chemokine activity, specifically CCR (9) activity. Generally, the compositions for modulating chemokine receptor activity in humans and animals will comprise a pharmaceutically acceptable excipient or diluent and a compound having any of the formulae I-III.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

In one embodiment, the present invention provides a composition consisting of a pharmaceutically acceptable carrier and a compound of the invention.

Methods of Treatment

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In some embodiments, compounds of the present invention are administered as part of a combination therapy. For instance an amount of a chemotherapeutic agent or radiation is administered to the subject prior to, subsequent to or in combination with the compounds of the present invention. In some embodiments, the amount is sub-therapeutic when the chemotherapeutic agent or radiation is administered alone. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

In still other embodiments, the present methods are directed to the treatment of allergic diseases, wherein a compound or composition of the invention is administered either alone or in combination with a second therapeutic agent, wherein said second therapeutic agent is an antihistamine or an anti-inflammatory. When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease (including Crohn's disease and ulcerative colitis), allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, aminosalicylates, corticosteroids and other immunosuppressive drugs, a non-steroidal antiinflammatory agent, or a cytokine-suppressing antiinflammatory agent, for example with a compound such as acetaminophen, aspirin, codeine, biological TNF sequestrants, biological agents which target $\alpha 4\beta 7$, ACE2 inhibitors, protein linase C inhibitors, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a $\beta 2$-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating or Preventing CCR(9)-Mediated Conditions or Diseases

In yet another aspect, the present invention provides methods of treating or preventing a CCR(9)-mediated condition or disease by administering to a subject having such a condition or disease a therapeutically effective amount of any compound of formulae above. Compounds for use in the present methods include those compounds according to the above formulae, those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR(9)-mediated condition or disease" and related phrases and terms refer to a condition or disease characterized by inappropriate, i.e., less than or greater than normal, CCR(9) functional activity. Inappropriate CCR(9) functional activity might arise as the result of CCR(9) expression in cells which normally do not express CCR(9), increased CCR(9) expression (leading to, e.g., inflammatory and immunoregulatory disorders and diseases) or decreased CCR(9) expression. Inappropriate CCR(9) functional activity might also arise as the result of TECK secretion by cells which normally do not secrete TECK, increased TECK expression (leading to, e.g., inflammatory and immunoregulatory disorders and diseases) or decreased TECK expression. A CCR(9)-mediated condition or disease may be completely or partially mediated by inappropriate CCR(9) functional activity. However, a CCR(9)-mediated condition or disease is one in which modulation of CCR(9) results in some effect on the underlying condition or disease (e.g., a CCR(9) antagonist results in some improvement in patient well-being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR(9) function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, microscopic colitis, ileitis and enteritis, and postoperative ileus, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, (15) irritable bowel syndrome, (16) primary sclerosing cholangitis, (17) cancer (including both primary and metastatic), (18) bacterial associated syndromes such as hemorrhagic colitis and hemolytic uremic syndrome (19) melanoma, (20) primary sclerosing cholangitis, (21) post-operative ileus, (22) hepatitis, and (23) inflammatory hepatic diseases.

In another group of embodiments, diseases or conditions can be treated with modulators and agonists of CCR(9) function. Examples of diseases to be treated by modulating CCR(9) function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

In yet other embodiments, the present methods are directed to the treatment of psoriasis where a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a 02-agonist and a corticosteroid.

Preparation of Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation and aza-aryl N-oxide formation are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and aza-aryls; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention. In particular, when $R^8$ is OH and ortho to a nitrogen, although illustrated by formula as —N=C(OH)— it is to be understood that the tautomeric form —NH—C(O)— is also within the scope of the formula.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

EXAMPLES

Exemplary compounds used in the method of the invention and in pharmaceutical compositions of the invention include but are not limited to the compounds listed in the following table. Pharmaceutically acceptable salts of the compounds listed in this table are also useful in the method of the invention and in pharmaceutical compositions of the invention. These compounds are within the scope of this invention and were tested for CCR(9) activity as described below.

Compounds of the invention were assayed for activity in the chemotaxis assay described herein under the section below titled "Example of in vitro assay" where the "chemotaxis assay" is described. All compounds listed in Table 1 has IC$_{50}$ of <1000 nM in the chemotaxis assay.

TABLE 1

Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).

| Chemical Structure | CCR(9) Ca$^{2+}$ |
|---|---|
| (structure) | + |
| (structure) | +++ |
| (structure) | +++ |
| (structure) | +++ |
| (structure) | ++ |

TABLE 1-continued
Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).
| Chemical Structure | CCR(9) Ca$^{2+}$ |
|---|---|
| 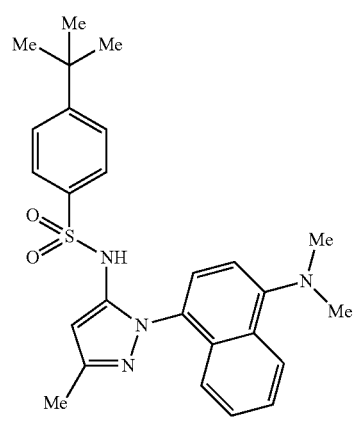 [SMILES: Cc1cc(NS(=O)(=O)c2ccc(C(C)(C)C)cc2)n(-c2ccc(N(C)C)c3ccccc23)n1] | +++ |
| 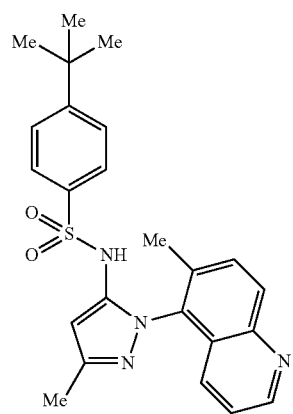 [SMILES: Cc1cc(NS(=O)(=O)c2ccc(C(C)(C)C)cc2)n(-c2c(C)ccc3ncccc23)n1] | +++ |

TABLE 1-continued

Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).

| Chemical Structure | CCR(9) Ca$^{2+}$ |
|---|---|
| (morpholine-fluoro-phenyl sulfonamide pyrazole quinoline, Me) | +++ |
| (tBu-phenyl sulfonamide cyclopropyl-pyrazole quinoline) | +++ |
| (tBu-OMe-phenyl sulfonamide Me-pyrazole quinoline) | +++ |
| (tBu-phenyl sulfonamide Me-pyrazole 2-quinoline) | ++ |
| (tBu-phenyl sulfonamide Me-pyrazole 3-Me-quinoline) | ++ |
| (tBu-phenyl sulfonamide Me-pyrazole 7-quinoline) | +++ |

TABLE 1-continued

Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).

| Chemical Structure | CCR(9) Ca$^{2+}$ |
|---|---|
| [structure: 4-tert-butylphenyl-SO$_2$NH-(4-fluoro-3-methyl-pyrazol-5-yl) with N1-quinolin-5-yl] | +++ |
| [structure: 4-tert-butylphenyl-SO$_2$NH-(3-methyl-pyrazol-5-yl) with N1-CH$_2$-isoquinolin-5-yl] | +++ |
| [structure: 4-tert-butylphenyl-SO$_2$NH-(3-cyanomethyl-pyrazol-5-yl) with N1-quinolin-5-yl] | +++ |
| [structure: 4-(1-methoxyethyl)phenyl-SO$_2$NH-(3-(1,1-difluoroethyl)-pyrazol-5-yl) with N1-quinolin-5-yl] | +++ |
| [structure: 4-isopropylphenyl-SO$_2$NH-(3-(1,1-difluoroethyl)-pyrazol-5-yl) with N1-quinolin-5-yl] | +++ |
| [structure: 4-tert-butylphenyl-SO$_2$NH-(3-(1,1-difluoroethyl)-pyrazol-5-yl) with N1-quinolin-5-yl] | +++ |

TABLE 1-continued
Exemplary compounds with CCR(9) activity in calcium mobilization assay. Compounds having an $IC_{50}$ value of less than 100 nM are labeled (+++); from 100-1000 nM are labeled (++); and above 1000 nM are labeled (+).
| Chemical Structure | CCR(9) $Ca^{2+}$ |
|---|---|
| 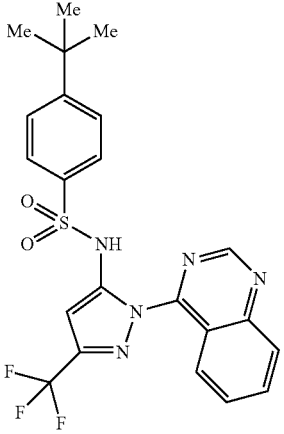 [SMILES: CC(C)(C)c1ccc(S(=O)(=O)Nc2cc(C(F)(F)F)nn2-c2ncnc3ccccc23)cc1] | +++ |
| 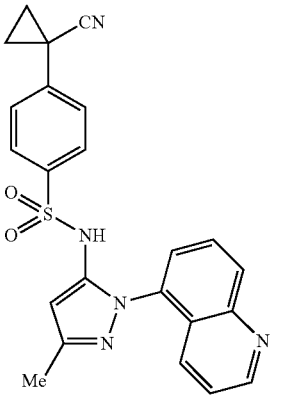 | +++ |
| 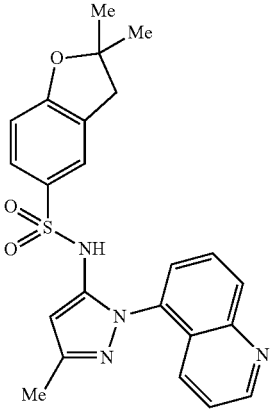 [SMILES: Cc1cc(NS(=O)(=O)c2ccc3c(c2)CC(C)(C)O3)n(-c2cccc3ncccc23)n1] | +++ |
| 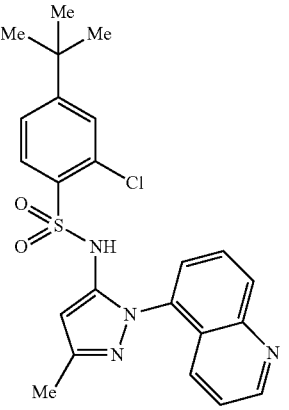 | +++ |
| 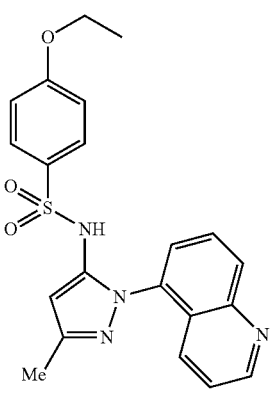 [SMILES: CCOc1ccc(S(=O)(=O)Nc2cc(C)nn2-c2cccc3ncccc23)cc1] | +++ |
| 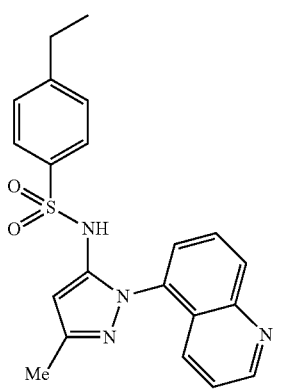 [SMILES: CCc1ccc(S(=O)(=O)Nc2cc(C)nn2-c2cccc3ncccc23)cc1] | +++ |

TABLE 1-continued
Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).
| Chemical Structure | CCR(9) Ca$^{2+}$ |
|---|---|
| 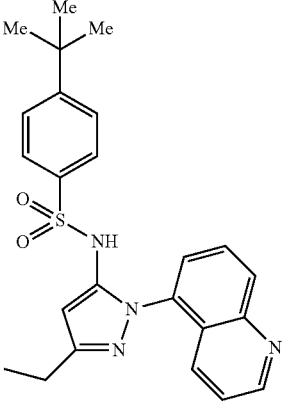 [SMILES: CCc1cc(NS(=O)(=O)c2ccc(C(C)(C)C)cc2)n(-c2cccc3ncccc23)n1] | +++ |
| 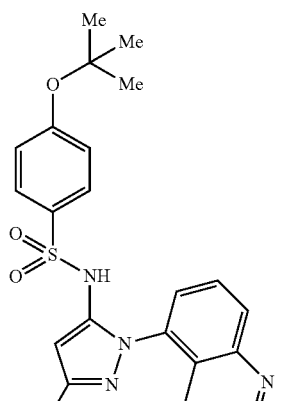 | ++ |
| 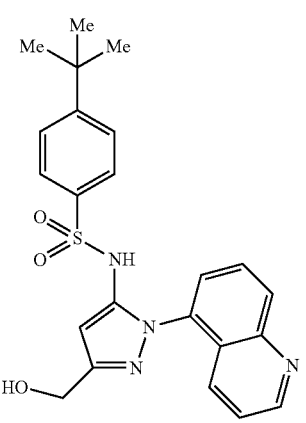 | ++ |
| 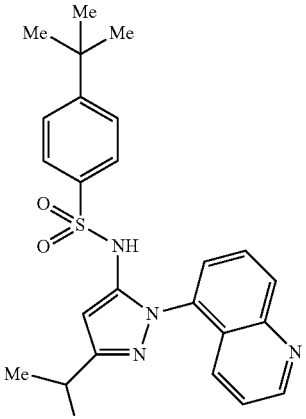 | + |
| 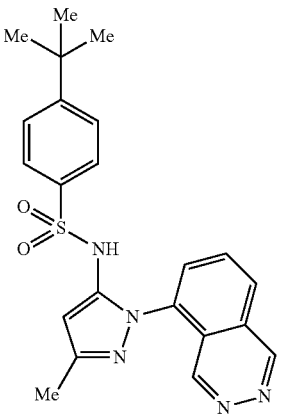 [SMILES: Cc1cc(NS(=O)(=O)c2ccc(C(C)(C)C)cc2)n(-c2cccc3cnncc23)n1] | +++ |
| 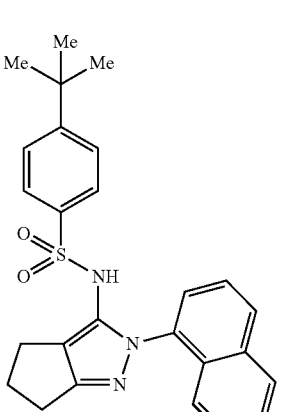 | +++ |

TABLE 1-continued
Exemplary compounds with CCR(9) activity in calcium mobilization assay. Compounds having an $IC_{50}$ value of less than 100 nM are labeled (+++); from 100-1000 nM are labeled (++); and above 1000 nM are labeled (+).
| Chemical Structure | CCR(9) $Ca^{2+}$ |
|---|---|
| 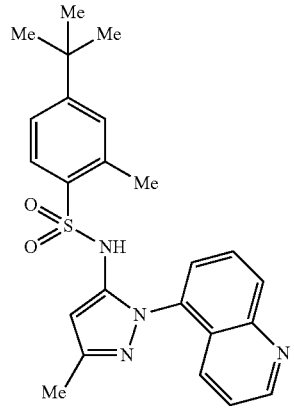 | ++ |
| 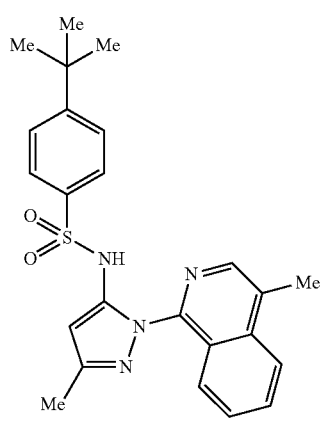 [SMILES: Cc1cc(NS(=O)(=O)c2ccc(C(C)(C)C)cc2)n(-c2ncc(C)c3ccccc23)n1] | +++ |
| 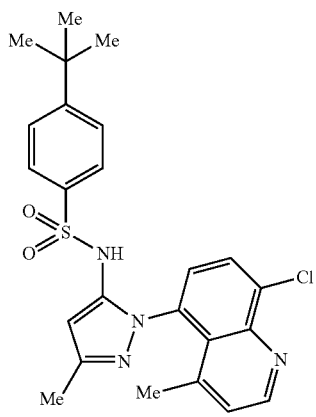 [SMILES: Cc1cc(NS(=O)(=O)c2ccc(C(C)(C)C)cc2)n(-c2ccc(Cl)c3nccc(C)c23)n1] | +++ |
| 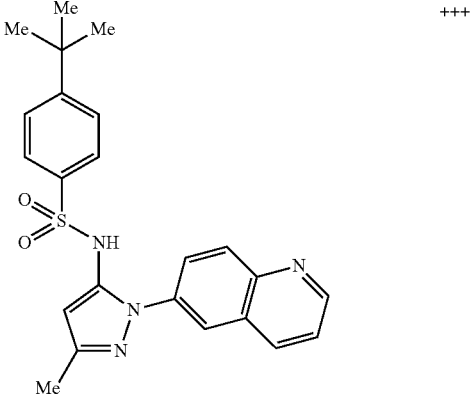 | +++ |
| 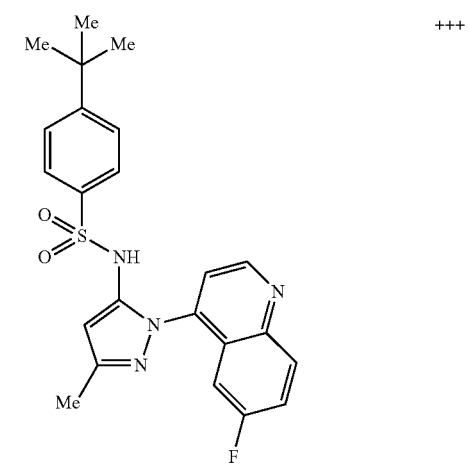 | +++ |
| 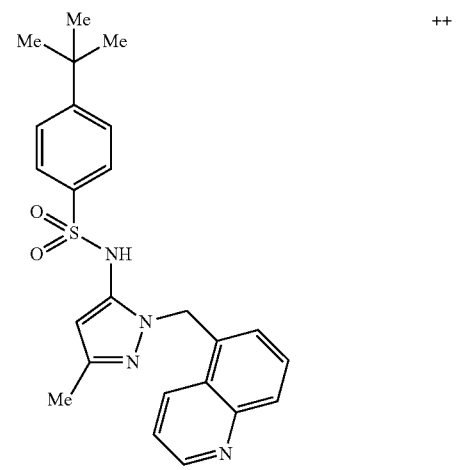 | ++ |

TABLE 1-continued

Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).

| Chemical Structure | CCR(9) Ca$^{2+}$ |
| --- | --- |
| [structure: 4-tert-butylphenylsulfonamide-N-(1-(isoquinolin-3-yl)-3-methyl-1H-pyrazol-5-yl)] | +++ |
| [structure: 4-tert-butylphenylsulfonamide-N-(1-(8-chloro-3-methylquinolin-5-yl)-3-methyl-1H-pyrazol-5-yl)] | +++ |
| [structure: 2,2-dimethylchroman-6-sulfonamide-N-(3-methyl-1-(quinolin-5-yl)-1H-pyrazol-5-yl)] | +++ |

TABLE 1-continued

Exemplary compounds with CCR(9) activity in calcium mobilization assay. Compounds having an IC$_{50}$ value of less than 100 nM are labeled (+++); from 100-1000 nM are labeled (++); and above 1000 nM are labeled (+).

| Chemical Structure | CCR(9) Ca$^{2+}$ |
| --- | --- |
| [structure: 4-tert-butyl-N-(3-carbamoyl-1-(quinolin-5-yl)-1H-pyrazol-5-yl)benzenesulfonamide] | ++ |
| [structure: 4-tert-butyl-N-(3-methyl-1-(naphthalen-2-yl)-1H-pyrazol-5-yl)benzenesulfonamide] | +++ |

TABLE 2

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
| --- | --- |
| [structure: 4-tert-butyl-N-(1-(quinolin-5-yl)-3-(trifluoromethyl)-1H-pyrazol-5-yl)benzenesulfonamide] | ++ |

TABLE 2-continued
Exemplary compounds with CCR(9) activity in serum migration assay. Compounds having an IC$_{50}$ value of less than 500 nM are labeled (+++); from 501-2500 nM are labeled (++); and above 2501 nM are labeled (+).
| Chemical Structure | A2 |
|---|---|
|  | ++ |
| 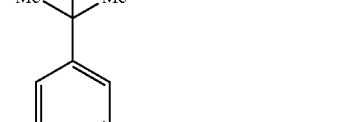 | +++ |
|  | ++ |
| 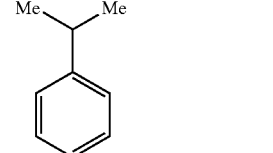 | ++ |
| 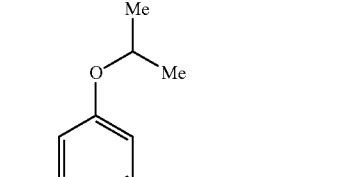 | +++ |
| | ++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| 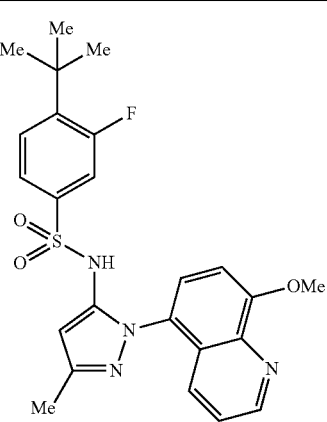 | +++ |
| 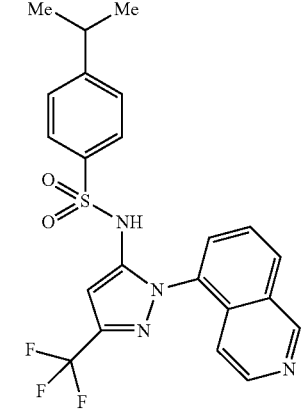 [SMILES: CC(C)c1ccc(S(=O)(=O)Nc2cc(C(F)(F)F)nn2-c2cccc3cnccc23)cc1] | ++ |
| 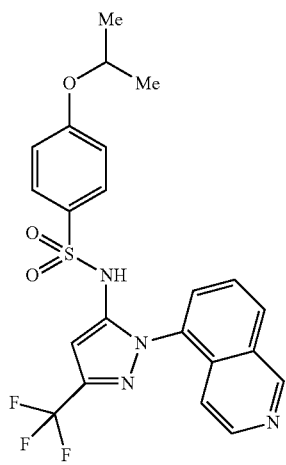 [SMILES: CC(C)Oc1ccc(S(=O)(=O)Nc2cc(C(F)(F)F)nn2-c2cccc3cnccc23)cc1] | ++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| 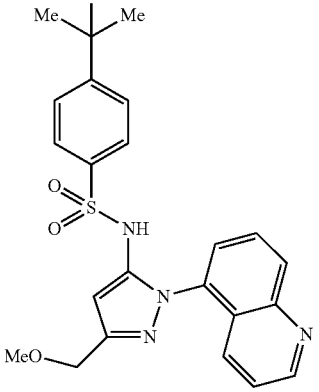 | +++ |
| 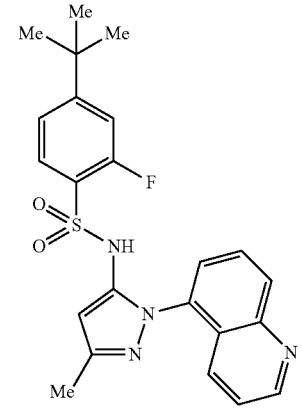 [SMILES: Cc1cc(NS(=O)(=O)c2ccc(C(C)(C)C)cc2F)n(-c2cccc3ncccc23)n1] | ++ |
| 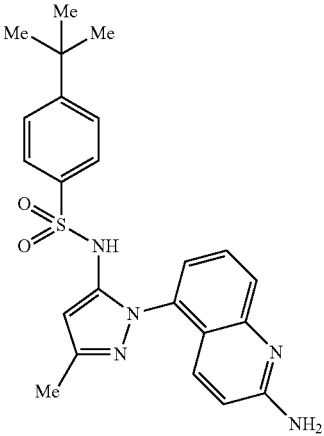 [SMILES: Cc1cc(NS(=O)(=O)c2ccc(C(C)(C)C)cc2)n(-c2cccc3nc(N)ccc23)n1] | +++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| (structure) | ++ |
| (structure) | ++ |
| (structure) | ++ |
| (structure) | ++ |
| (structure) | ++ |
| (structure) | ++ |

TABLE 2-continued
Exemplary compounds with CCR(9) activity in serum migration assay. Compounds having an IC$_{50}$ value of less than 500 nM are labeled (+++); from 501-2500 nM are labeled (++); and above 2501 nM are labeled (+).
| Chemical Structure | A2 |
|---|---|
| 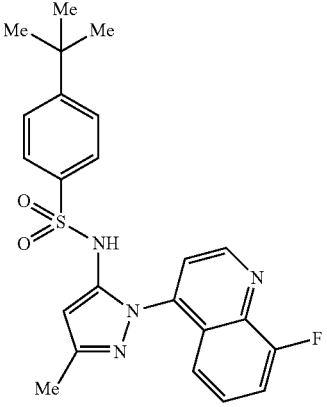 [SMILES: Cc1cc(NS(=O)(=O)c2ccc(C(C)(C)C)cc2)n(-c2ccnc3c(F)cccc23)n1] | ++ |
| 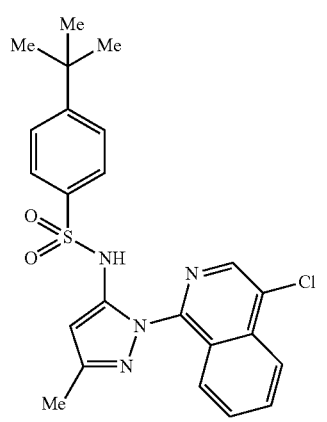 | + |
| 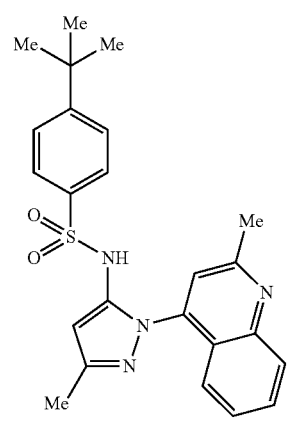 [SMILES: Cc1cc(-n2nc(C)cc2NS(=O)(=O)c2ccc(C(C)(C)C)cc2)c2ccccc2n1] | ++ |
| 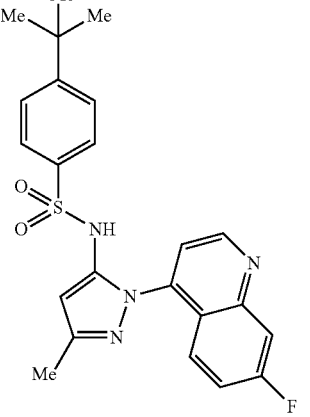 | ++ |
| | +++ |
| | ++ |

TABLE 2-continued
Exemplary compounds with CCR(9) activity in serum migration assay. Compounds having an IC$_{50}$ value of less than 500 nM are labeled (+++); from 501-2500 nM are labeled (++); and above 2501 nM are labeled (+).
| Chemical Structure | A2 |
|---|---|
| 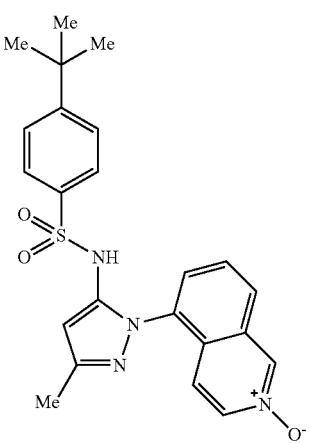 [SMILES: Cc1cc(NS(=O)(=O)c2ccc(C(C)(C)C)cc2)n(-c2cccc3c[n+]([O-])ccc23)n1] | + |
| 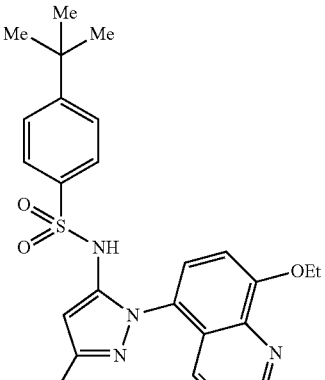 | ++ |
| 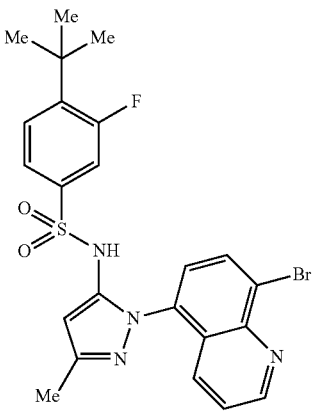 | +++ |
| 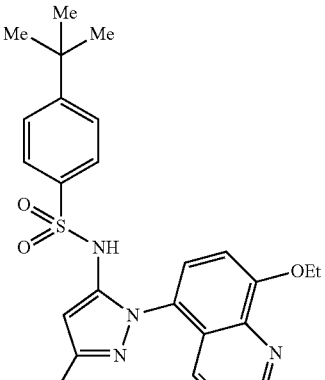 | ++ |
| 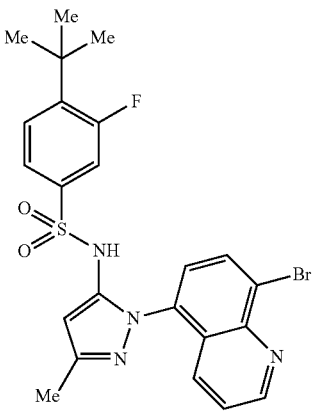 | +++ |
| 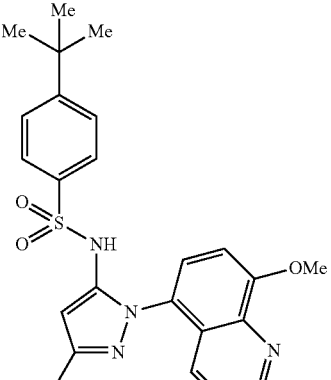 | +++ |
| 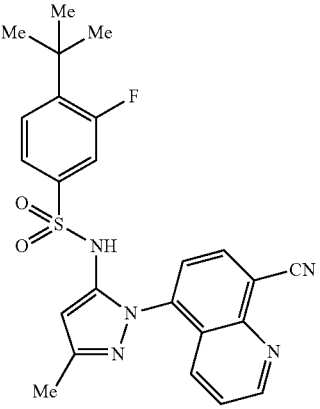 [SMILES: Cc1cc(NS(=O)(=O)c2ccc(C(C)(C)C)c(F)c2)n(-c2ccc(C#N)c3ncccc23)n1] | +++ |

TABLE 2-continued

Exemplary compounds with CCR(9) activity in serum migration assay. Compounds having an $IC_{50}$ value of less than 500 nM are labeled (+++); from 501-2500 nM are labeled (++); and above 2501 nM are labeled (+).

| Chemical Structure | A2 |
|---|---|
| (4-isobutoxyphenyl)sulfonamide-pyrazole-quinoline with Me on pyrazole | + |
| (4-tert-butylphenyl)sulfonamide-pyrazole-isoquinoline with Me on pyrazole | ++ |
| 4-(1-methylethyl)phenyl sulfonamide-pyrazole-quinoline with Me on pyrazole | ++ |
| 4-(2-methylbutan-2-yl)phenyl sulfonamide-pyrazole-quinoline with Me on pyrazole | ++ |
| 4-tert-butylphenyl sulfonamide-pyrazole-quinoline with CN on pyrazole | ++ |
| 4-tert-butylphenyl sulfonamide-pyrazole-quinoline | + |

TABLE 2-continued

Exemplary compounds with CCR(9) activity in serum migration assay. Compounds having an $IC_{50}$ value of less than 500 nM are labeled (+++); from 501-2500 nM are labeled (++); and above 2501 nM are labeled (+).

| Chemical Structure | A2 |
|---|---|
| 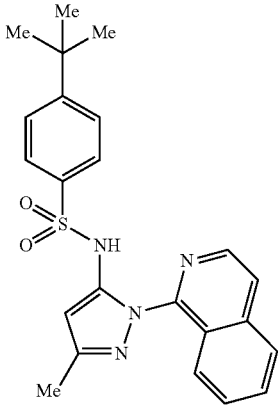 | ++ |
| 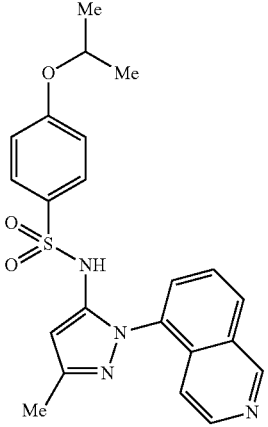 [SMILES: Cc1cc(NS(=O)(=O)c2ccc(OC(C)C)cc2)n(-c2cccc3cnccc23)n1] | ++ |
| 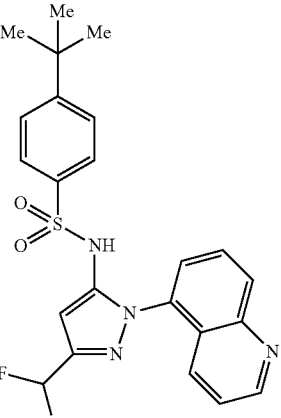 | +++ |

TABLE 2-continued

Exemplary compounds with CCR(9) activity in serum migration assay. Compounds having an $IC_{50}$ value of less than 500 nM are labeled (+++); from 501-2500 nM are labeled (++); and above 2501 nM are labeled (+).

| Chemical Structure | A2 |
|---|---|
| 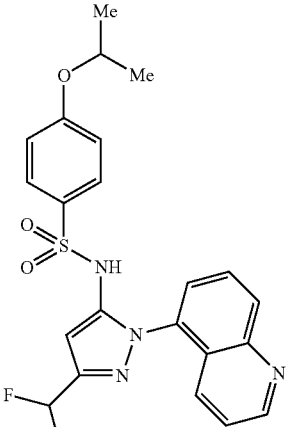 | +++ |
| 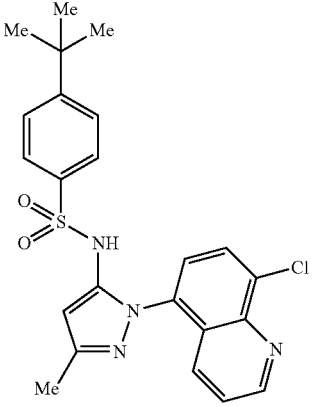 [SMILES: Cc1cc(NS(=O)(=O)c2ccc(C(C)(C)C)cc2)n(-c2ccc(Cl)c3ncccc23)n1] | +++ |
| 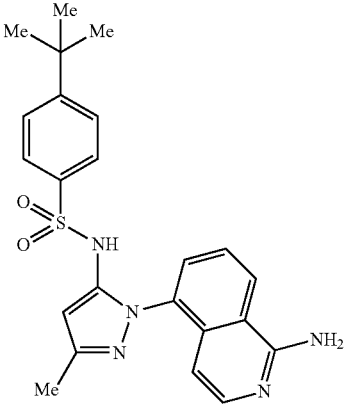 [SMILES: Cc1cc(NS(=O)(=O)c2ccc(C(C)(C)C)cc2)n(-c2cccc3c(N)nccc23)n1] | ++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| 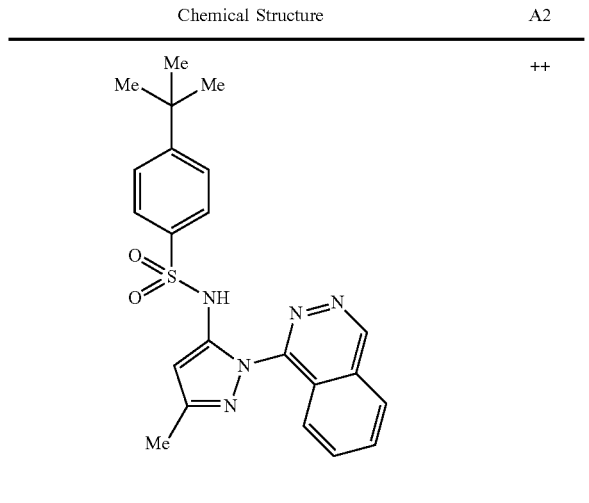 | ++ |
| 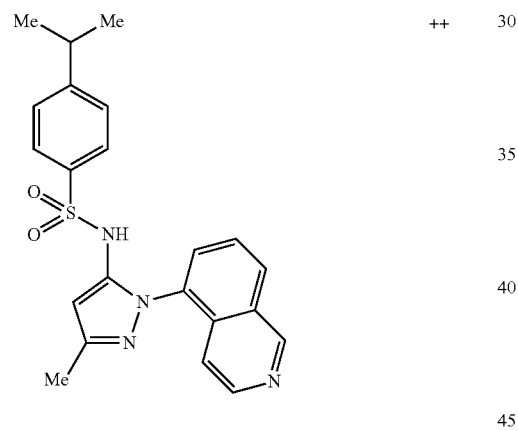 | ++ |
| 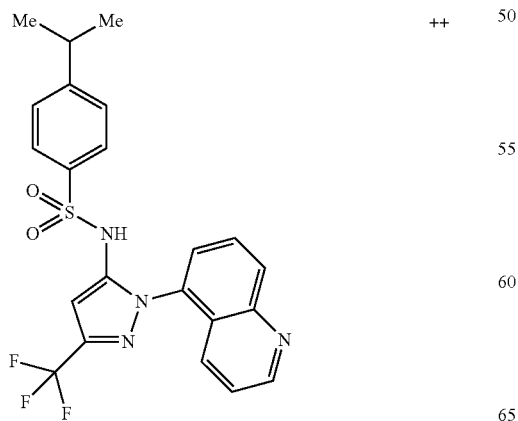 | ++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| 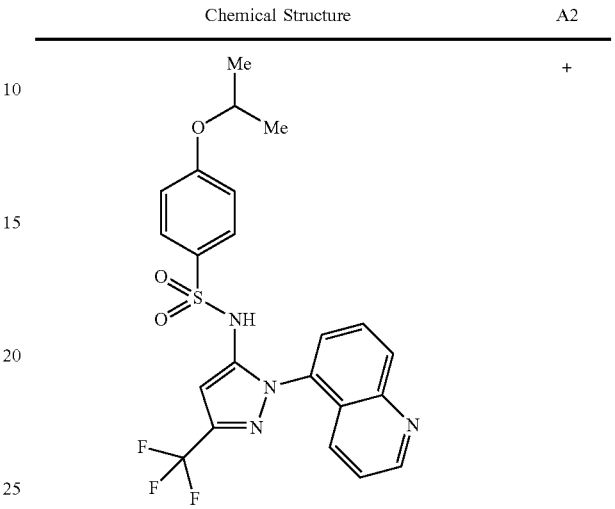 | + |
| 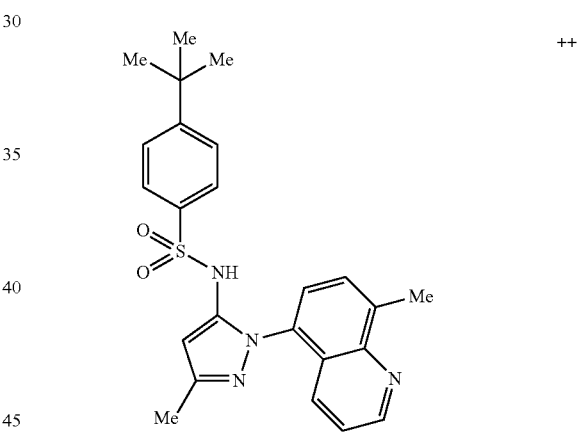 | ++ |
| 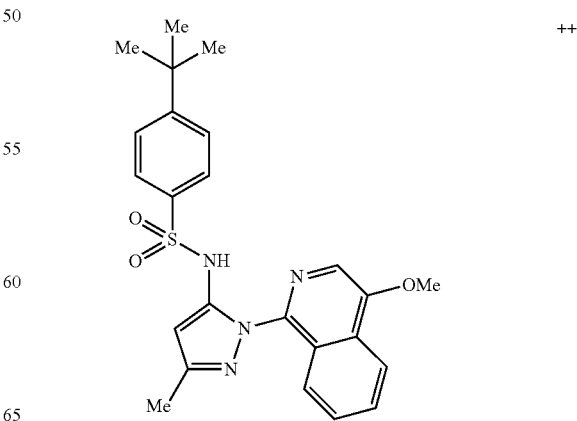 | ++ |

TABLE 2-continued

Exemplary compounds with CCR(9) activity in serum migration assay. Compounds having an $IC_{50}$ value of less than 500 nM are labeled (+++); from 501-2500 nM are labeled (++); and above 2501 nM are labeled (+).

| Chemical Structure | A2 |
| --- | --- |
| (4-tert-butylphenyl)sulfonamide linked to 3-methyl-1-(1-aminoisoquinolin-4-yl)pyrazol-5-yl | ++ |
| (4-tert-butyl-3-fluorophenyl)sulfonamide linked to 3-methyl-1-(quinolin-5-yl)pyrazol-5-yl | +++ |
| (4-tert-butyl-3-fluorophenyl)sulfonamide linked to 3-(difluoromethyl)-1-(quinolin-5-yl)pyrazol-5-yl | ++ |
| (4-tert-butyl-3-fluorophenyl)sulfonamide linked to 3-methyl-1-(8-aminoquinolin-5-yl)pyrazol-5-yl | ++ |
| (4-tert-butyl-3-fluorophenyl)sulfonamide linked to 3-(fluoromethyl)-1-(quinolin-5-yl)pyrazol-5-yl | +++ |
| (4-tert-butylphenyl)sulfonamide linked to 3-methyl-1-(8-fluoroquinolin-5-yl)pyrazol-5-yl | ++ |

TABLE 2-continued

Exemplary compounds with CCR(9) activity in serum migration assay. Compounds having an IC$_{50}$ value of less than 500 nM are labeled (+++); from 501-2500 nM are labeled (++); and above 2501 nM are labeled (+).

| Chemical Structure | A2 |
|---|---|
| (structure: 3-chloro-4-tert-butylphenylsulfonamide linked to 1-(quinolin-5-yl)-3-methylpyrazol-5-amine) | ++ |
| (structure: 3,5-difluoro-4-tert-butylphenylsulfonamide linked to 1-(quinolin-5-yl)-3-methylpyrazol-5-amine) | +++ |
| (structure: 4-tert-butylphenylsulfonamide linked to 1-(quinolin-5-yl)-3-methylpyrazol-5-amine) | +++ |
| (structure: 4-tert-butylphenylsulfonamide linked to 1-(7-methylquinolin-5-yl)-3-methylpyrazol-5-amine) | ++ |
| (structure: 4-(isopropoxy)-3-fluorophenylsulfonamide linked to 1-(quinolin-5-yl)-3-methylpyrazol-5-amine) | ++ |
| (structure: 4-tert-butylphenylsulfonamide linked to 1-(8-amino-quinolin-5-yl)-3-methylpyrazol-5-amine) | +++ |

TABLE 2-continued

Exemplary compounds with CCR(9) activity in serum migration assay. Compounds having an $IC_{50}$ value of less than 500 nM are labeled (+++); from 501-2500 nM are labeled (++); and above 2501 nM are labeled (+).

| Chemical Structure | A2 |
|---|---|
| (structure with Me, Me, Me group, phenyl, sulfonamide, pyrazole-Me, quinoline-CN) | ++ |

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H, M+Na, etc.) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

Compounds of the present invention may be synthesized by General Synthesis A shown below. Treatment of an aryl sulfonyl chloride of formula A with the pyrazole amine B in the presence of a base such as pyridine at a suitable temperature, for example 80° C., affords the aryl sulfonamides of formula C. The pyrazole amines, B, may be synthesized treatment of hydrazine D with nitrile C at a suitable elevated temperature in a solvent such as ethanol. One skilled in the art will understand that the substituents, including, for example, $R^1$, $R^2$, $R^3$, $R^4$, and $R^6$ may need to be protected as known to one skilled in the art with standard protecting groups during the synthesis depending upon their reactivity to the reaction conditions.

General Synthesis A

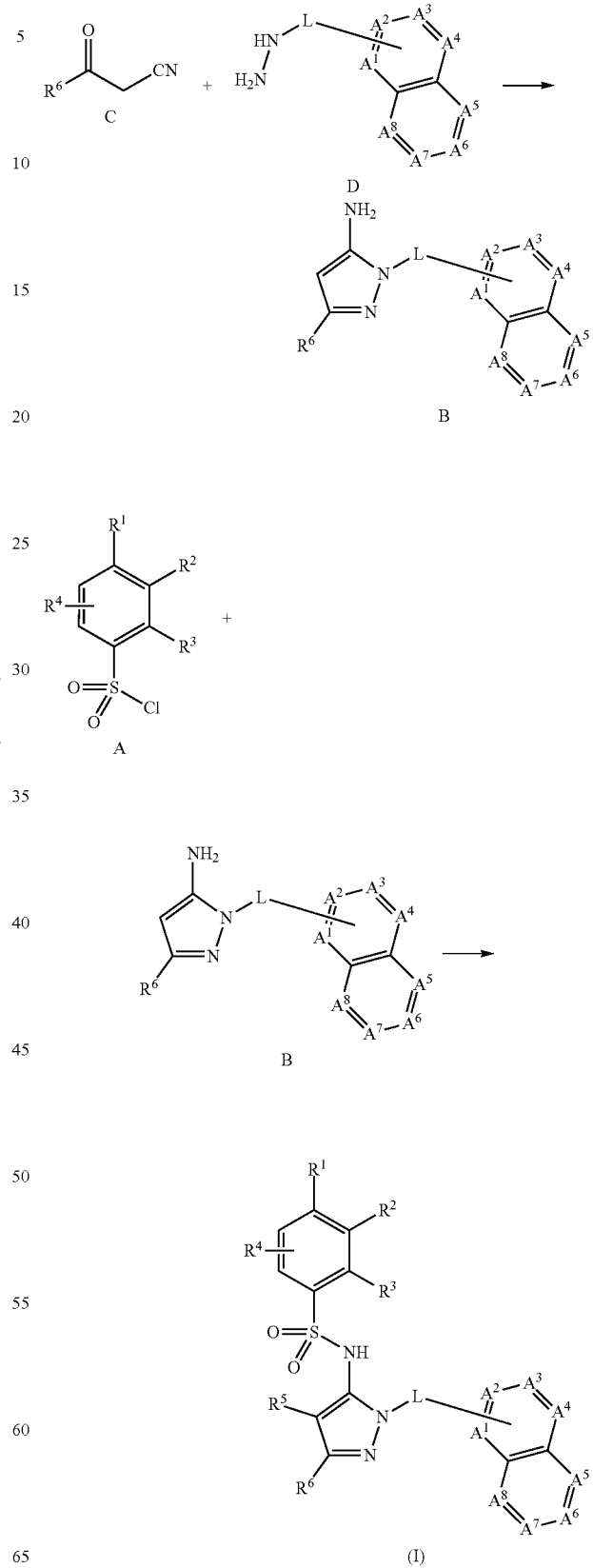

Example 1: Synthesis of 4-t-butyl-N-(3-methyl-1-(quinazolin-4-yl)-1H-pyrazol-5-yl)benzenesulfonamide

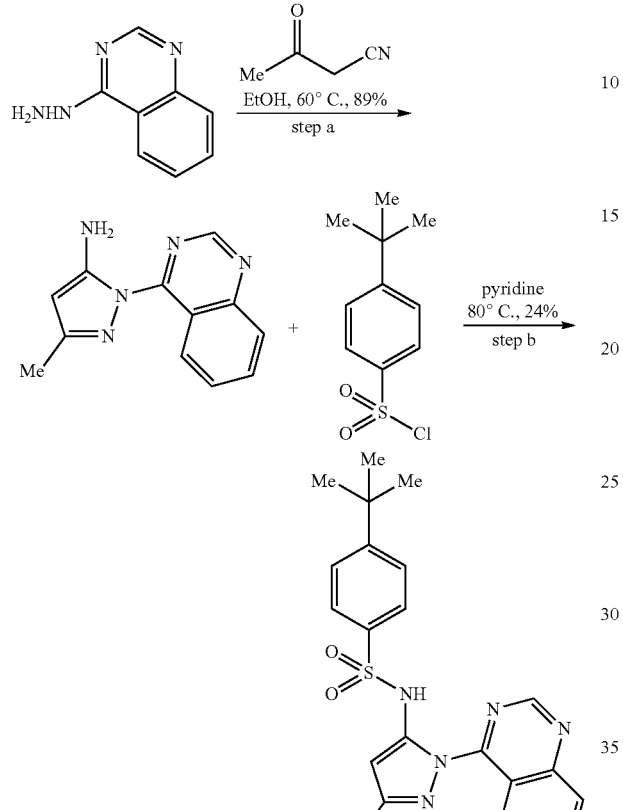

Example 2: Synthesis of 4-t-butyl-N-(1-(isoquinolin-4-yl)-3-methyl-1H-pyrazol-5-yl)benzenesulfonamide

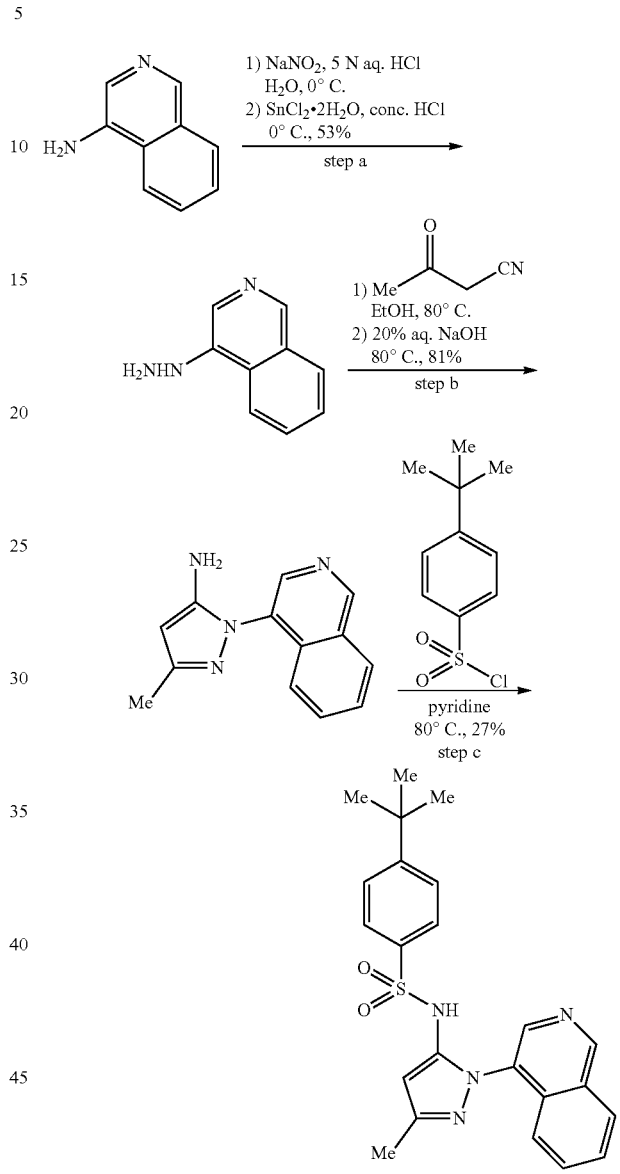

a) To a stirring solution of 4-hydrazinoquinazoline (0.16 g, 1.0 mmol) and 3-oxo-butyronitrile (0.083 g, 1.0 mmol) in ethanol (10 mL) was heated at 60° C. for 18 h. After cooling to room temperature, the reaction mixture was concentrated in vacuo. The crude residue was purified by flash chromatography (SiO$_2$, 30% ethyl acetate in hexanes) to give the desired compound (0.20 g, 0.089 mmol, 89%).

b) To a mixture of 4-t-butylbenzenesulfonyl chloride (0.084 g, 0.36 mmol) and 3-methyl-1-(quinazolin-4-yl)-1H-pyrazol-5-amine (0.067 g, 0.30 mmol) in pyridine (0.6 mL) was heated at 80° C. for 15 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by flash chromatography (SiO$_2$, 5-60% ethyl acetate in hexanes) to give the title compound as a white solid (0.30 g, 0.071 mmol, 24%). $^1$H NMR (400 MHz, CDCl$_3$) δ 10.92 (s, 1H), 9.27 (dd, J=1.2, 8.8 Hz, 1H), 9.98 (s, 1H), 7.99 (dd, J=0.8, 8.4 Hz, 1H), 7.89 (ddd, J=1.2, 6.8, 8.4 Hz, 1H), 7.66-7.61 (m, 2H), 7.28-7.25 (m, 2H), 6.34 (s, 1H), 2.37 (s, 3H), 1.13 (s, 9H); MS: (ES) m/z calculated for C$_{22}$H$_{24}$F$_3$N$_5$O$_2$S [M+H]$^+$ 422.2, found 422.3.

a) To a stirring solution of 4-aminoisoquinoline (1.4 g, 10.0 mmol) in 5 N aqueous hydrochloric acid (12 mL) at 0° C. was added a solution of sodium nitrite (NaNO$_2$, 0.069 g, 10.0 mmol) in deionized water (1 mL), while maintaining the internal temperature below 0° C. The reaction mixture was stirred at 0° C. for 30 min and a solution of tin(II) chloride dihydrate (SnCl$_2$.2H$_2$O, 5.6 g, 25.0 mmol) dissolved in concentrated hydrochloric acid (5 mL) was added dropwise. The mixture was stirred at room temperature for 2 h and the solution was adjusted to pH ~12-14 with 20% aqueous sodium hydroxide. The mixture was extracted with 2:1 CHCl$_3$/iPrOH. The organic layer was dried (Na$_2$SO$_4$), filtered, and concentrated in vacuo. The resulting crude product was purified by flash chromatography (SiO$_2$, 50% ethyl acetate in hexanes) to give the desired compound (0.84 g, 5.3 mmol, 53%).

b) To a stirring suspension of 4-hydrazinylisoquinoline (0.32 g, 2.0 mmol) and 3-oxo-butyronitrile (0.16 g, 0.19 mmol) in ethanol (10 mL) was heated at 80° C. for 3 h. After cooling to room temperature, 20% aqueous sodium hydroxide (1 mL) was added to the reaction mixture and was further heated at 80° C. for 1 h. The reaction mixture was cooled to room temperature and concentrated in vacuo. The crude residue was dissolved in 1:1 dichloromethane/methanol (40 mL) and the phases were separated. The organic layer was dried (Na$_2$SO$_4$), and filtered through a pad of Celite. The filtrate was concentrated in vacuo and the crude residue was purified by flash chromatography (SiO$_2$, 50-100% ethyl acetate in hexanes) to give the desired product (0.36 g, 1.6 mmol, 81%).

c) A mixture of 4-t-butylbenzenesulfonyl chloride (0.10 g, 0.43 mmol) and 1-(isoquinolin-4-yl)-3-methyl-1H-pyrazol-5-amine (0.080 g, 0.36 mmol) in pyridine (5 mL) was heated at 80° C. for 15 h with stirring. After cooling to room temperature, the reaction mixture was concentrated in vacuo. The crude residue was purified by flash chromatography (SiO$_2$, 50-100% ethyl acetate in hexanes) to give the title compound as a white solid (0.18 g, 0.12 mmol, 27%). $^1$H NMR (400 MHz, CDCl$_3$) δ 8.89 (s, 1H), 8.02 (s, 1H), 8.87 (dd, J=1.6, 6.8 Hz, 1H), 7.58-7.53 (m, 2H), 7.58 (s, 1H), 7.56 (s, 1H), 7.39-7.35 (m, 3H), 6.25 (s, 1H), 2.34 (s, 3H), 1.32 (s, 9H); MS: (ES) m/z calculated for C$_{23}$H$_{25}$N$_4$O$_2$S [M+H]$^+$ 421.2, found 422.2.

Example 3: Synthesis of 4-t-butyl-N-(1-(8-fluoroquinolin-4-yl)-3-methyl-1H-pyrazol-5-yl)benzenesulfonamide reaction mixture was stirred at 0° C. for 30 min and a solution of SnCl$_2$.2H$_2$O (2.8 g, 12.4 mmol) dissolved in deionized water (3 mL) was then added dropwise. The mixture was stirred at room temperature for 2 h and the suspension was basified with aqueous sodium bicarbonate. The mixture was extracted with 2:1 CHCl$_3$/iPrOH. The organic layer was washed with 1 M aqueous sodium bisulfate, dried (Na$_2$SO$_4$), filtered, and concentrated in vacuo. The resulting crude product was used directly without further purification (0.34 g, 1.9 mmol, 31%).

b) To a solution of crude 4-chloro-8-fluoroquinoline (0.27 g, 1.5 mmol) and NH$_2$NH$_2$.H$_2$O (1.5 mL, 16.6 mmol) in ethanol (1.6 mL) was heated at 160° C. in microwave for 1 h with stirring. After cooling the mixture to room temperature, aqueous saturated sodium bicarbonate was added to the reaction mixture and the aqueous layer was extracted with 2:1 CHCl$_3$/iPrOH (2×5 mL). The combine organic layers were washed with water, dried (Na$_2$SO$_4$), filtered, and concentrated in vacuo. The crude residue was used directly without further purification (0.27 g, 1.5 mmol, 100%).

c) To a stirring solution of crude 8-fluoro-4-hydrazinylquinoline (0.27 g, 1.5 mmol) and 3-oxo-butyronitrile (0.15 g, 0.19 mmol) in pyridine (3 mL) was heated at 80° C. for 15 h. After cooling to room temperature, aqueous saturated sodium bicarbonate was added to the reaction mixture and extracted with dichloromethane (3×10 mL). The combined organic layers were dried (Na$_2$SO$_4$), filtered, and concentrated in vacuo. The crude residue was used directly without further purification (0.14 g, 0.76 mmol, 50%).

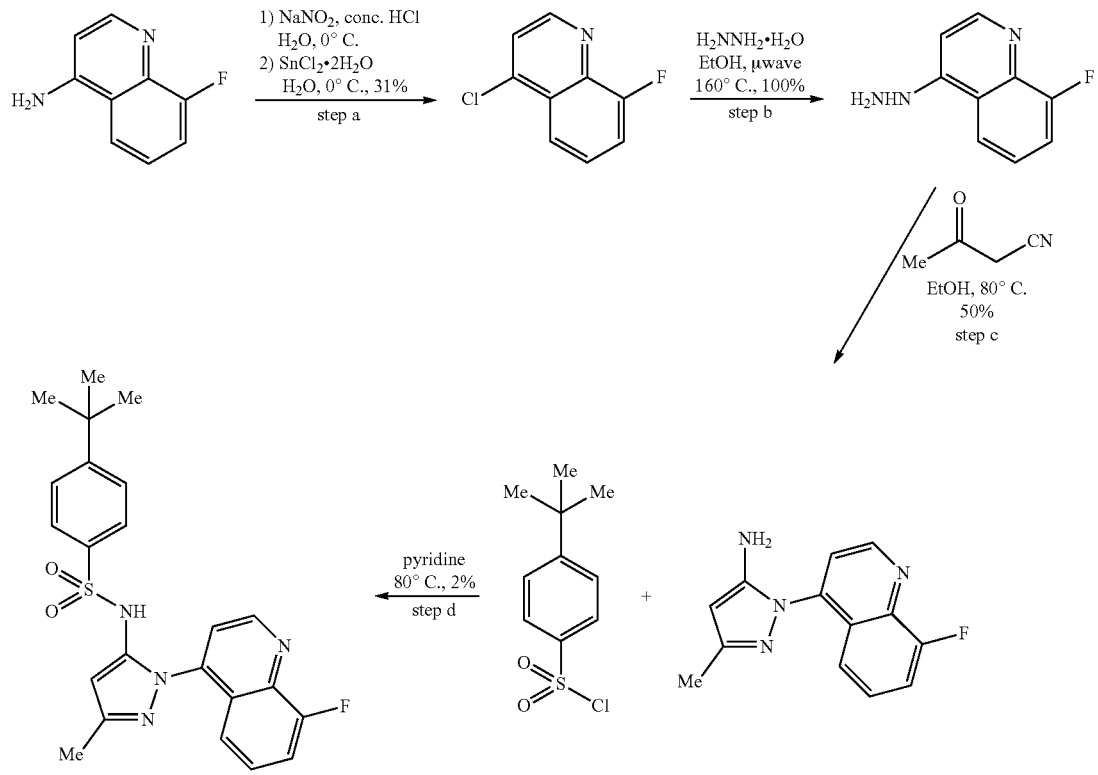

a) To a stirring solution of 8-fluoroquinolin-4-amine (1.0 g, 6.2 mmol) in concentrated hydrochloric acid (6.2 mL) and deionized water (6.0 mL) at 0° C. was added a solution of NaNO$_2$ (0.51 g, 7.4 mmol) in deionized water (3 mL). The d) A mixture of 4-t-butylbenzenesulfonyl chloride (0.13 g, 0.55 mmol) and crude 1-(8-fluoroquinolin-4-yl)-3-methyl-1H-pyrazol-5-amine (0.14 g, 0.55 mmol) in pyridine (1 mL) was heated at 80° C. for 15 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.005 g, 0.011 mmol, 2%). $^1$H NMR (400 MHz, CDCl$_3$) δ 8.80 (d, J=4.8 Hz, 1H), 7.61 (d, J=1.6 Hz, 1H), 7.59 (d, J=2.0 Hz, 1H), 7.47-7.41 (m, 5H), 7.13 (d, J=4.8 Hz, 1H), 6.20 (s, 1H), 2.35 (s, 3H), 1.35 (s, 9H); MS: (ES) m/z calculated for C$_{23}$H$_{24}$FN$_4$O$_2$S [M+H]$^+$ 439.5, found 439.3.

Example 4: Synthesis of 4-t-butyl-N-(3-methyl-1-(quinolin-5-yl)-1H-pyrazol-5-yl)benzenesulfonamide

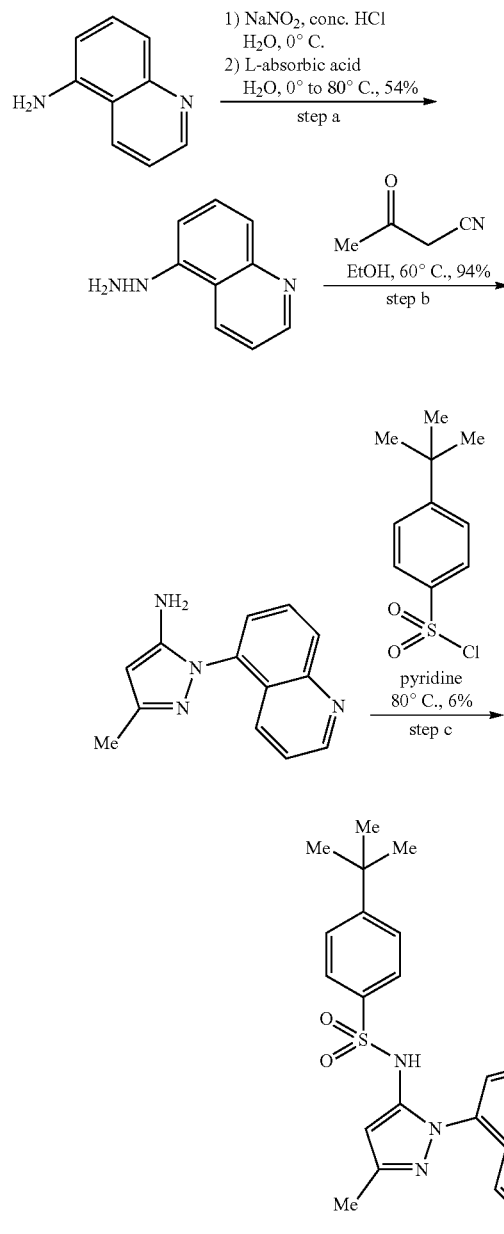

a) A solution of 5-aminoquinoline (0.75 g, 5.2 mmol) in concentrated hydrochloric acid (3.8 mL) was stirred at 0° C. for 10 min. A solution of sodium nitrite (0.43 g, 6.2 mmol) in deionized water (0.5 mL) was added to the cold reaction mixture over 10 min and stirred at 0° C. for 1 h to form a heterogeneous mixture. L-ascorbic acid (0.95 g, 5.4 mmol) was then added to the reaction mixture over 10 min. The reaction mixture was warmed to room temperature and stirred for 45 min. The reaction slurry was then heated at 80° C. for 20 min and deionized water (4 mL) was added. The suspension was re-cooled to 0° C. and stirred for 2 h. The solid was collected by filtration and washed with methanol to give the desired product (0.45 g, 2.8 mmol, 54%).

b) To a stirring suspension of quinolin-5-yl-hydrazine (0.25 g, 1.6 mmol) in 3:1 ethanol/deionized water (2.5 mL) was added 3-oxo-butyronitrile (0.13 g, 1.6 mmol). The reaction mixture was then heated at 60° C. for 2 h. After cooling to room temperature, the reaction mixture was concentrated in vacuo and the resulting crude product was used directly without further purification (0.21 g, 1.5 mmol, 94%)

c) A mixture of 4-t-butylbenzenesulfonyl chloride (0.59 g, 2.5 mmol) and crude 3-methyl-1-(quinolin-5-yl)-1H-pyrazol-5-amine (0.47 g, 2.1 mmol) in pyridine (0.6 mL) was heated at 80° C. for 15 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by flash chromatography (SiO$_2$, 1-10% methanol containing 10% ammonium hydroxide in dichloromethane) to give the title compound as a white solid (0.18 g, 0.12 mmol, 6%). $^1$H NMR (400 MHz, CDCl$_3$) δ 8.87 (dd, J=1.2, 4.0 Hz, 1H), 8.11 (d, J=8.4 Hz, 1H), 7.58-7.53 (m, 4H), 7.42 (s, 1H), 7.40 (s, 1H), 7.29-7.23 (m, 1H), 6.94 (d, J=7.2 Hz, 1H), 6.28 (s, 1H), 2.34 (s, 3H), 1.36 (s, 9H); MS: (ES) m/z calculated for C$_{23}$H$_{25}$N$_4$O$_2$S [M+H]+ 421.2, found 421.3.

Example 5: Synthesis of N-(3-methyl-1-(quinolin-5-yl)-1H-pyrazol-5-yl)-4-(trifluoromethoxy)benzenesulfonamide

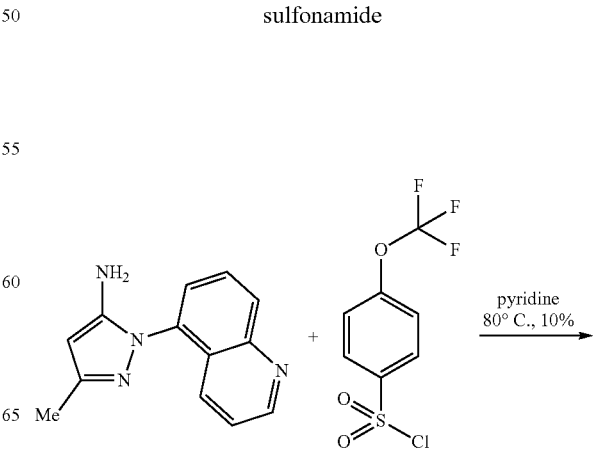

-continued

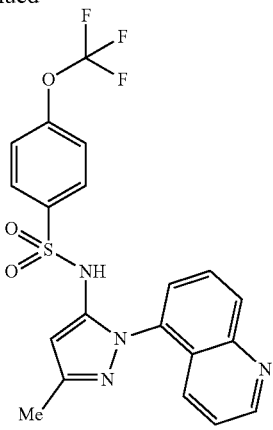

To a stirring mixture of 4-(trifluoromethoxy)benzene-1-sulfonyl chloride (0.060 g, 0.23 mmol) and 3-methyl-1-(quinolin-5-yl)-1H-pyrazol-5-amine (prepared from Example 4 step b, 0.050 g, 0.22 mmol) in pyridine (1.0 mL) was heated at 80° C. for 1 h. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by flash chromatography (SiO$_2$, 2-10% methanol in dichloromethane) and purification by reverse phase HPLC (C18 column, acetonitrile-H$_2$O with 0.1% TFA as eluent) to give the title compound as a white solid (0.010 g, 0.022 mmol, 10%). $^1$H NMR (400 MHz, CDCl$_3$) δ 8.75 (d, J=4.0 Hz, 1H), 8.01 (d, J=8.8 Hz, 1H), 7.71 (s, 1H), 7.69 (s, 1H), 7.56 (t, J=8.4 Hz, 1H), 7.49 (d, J=8.4 Hz, 1H), 7.21-7.17 (m, 4H), 6.12 (s, 1H), 2.34 (s, 3H); MS: (ES) m/z calculated for C$_{20}$H$_{16}$F$_3$N$_4$O$_3$S [M+H]$^+$ 449.1, found 449.7.

Example 6: Synthesis of 4-ethyl-N-(3-methyl-1-(quinolin-5-yl)-1H-pyrazol-5-yl)benzenesulfonamide

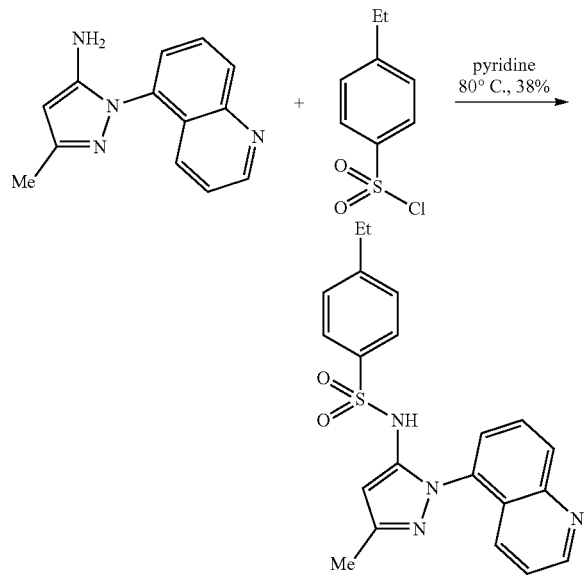

A mixture of 4-ethylbenzenesulfonyl chloride (0.033 g, 0.16 mmol) and 3-methyl-1-(quinolin-5-yl)-1H-pyrazol-5-amine (prepared from Example 4 step b, 0.030 g, 0.13 mmol) in pyridine (1.0 mL) was heated at 80° C. for 2 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.019 g, 0.049 mmol, 38%). $^1$H NMR (400 MHz, CDCl$_3$) δ 8.86 (dd, J=2.0, 4.0 Hz, 1H), 8.12 (d, J=8.8 Hz, 1H), 7.60 (dd, J=7.2, 8.4 Hz, 1H), 7.51-7.46 (m, 3H), 7.27-7.23 (m, 1H), 7.15 (s, 1H), 7.13 (s, 1H), 7.06 (d, J=7.6 Hz, 1H), 6.27 (s, 1H), 2.68 (q, J=7.6 Hz, 2H), 2.34 (s, 3H), 1.27 (t, J=7.6 Hz, 3H); MS: (ES) m/z calculated for C$_{21}$H$_{21}$N$_4$O$_2$S [M+H]+ 393.2, found 393.2.

Example 7: Synthesis of 4-isopropyl-N-(3-methyl-1-(quinolin-5-yl)-1H-pyrazol-5-yl)benzenesulfonamide

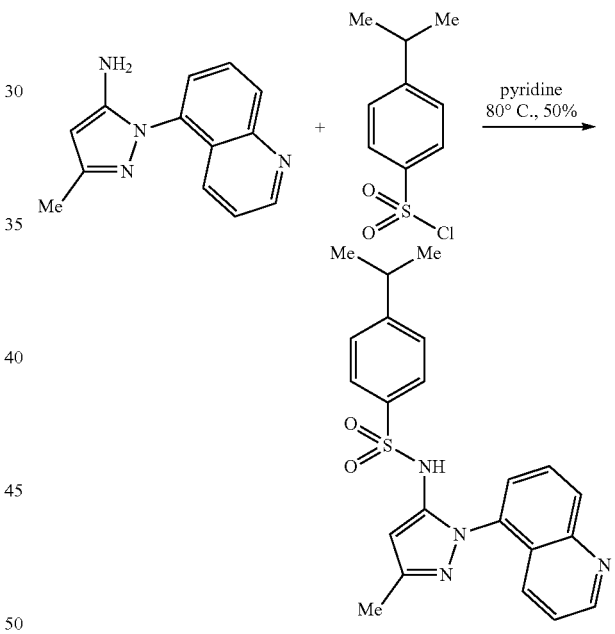

A mixture of 4-t-pentylbenzenesulfonyl chloride (0.028 g, 0.13 mmol) and 3-methyl-1-(quinolin-5-yl)-1H-pyrazol-5-amine (prepared from Example 4 step b, 0.023 g, 0.10 mmol) in pyridine (1.0 mL) was heated at 80° C. for 18 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.020 g, 0.05 mmol, 50%). $^1$H NMR (400 MHz, CDCl$_3$) δ 9.02 (d, J=4.4 Hz, 1H), 8.43 (d, J=8.8 Hz, 1H), 8.30 (d, J=8.4 Hz, 1H), 7.87-7.33 (m, 2H), 7.72-7.70 (m, 3H), 7.35 (s, 1H), 7.33 (s, 1H), 5.94 (s, 1H),

Example 8: Synthesis of 4-isopropoxy-N-(3-methyl-1-(quinolin-5-yl)-1H-pyrazol-5-yl)benzenesulfonamide

Example 9: Synthesis of 4-isobutoxy-N-(3-methyl-1-(quinolin-5-yl)-1H-pyrazol-5-yl)benzenesulfonamide

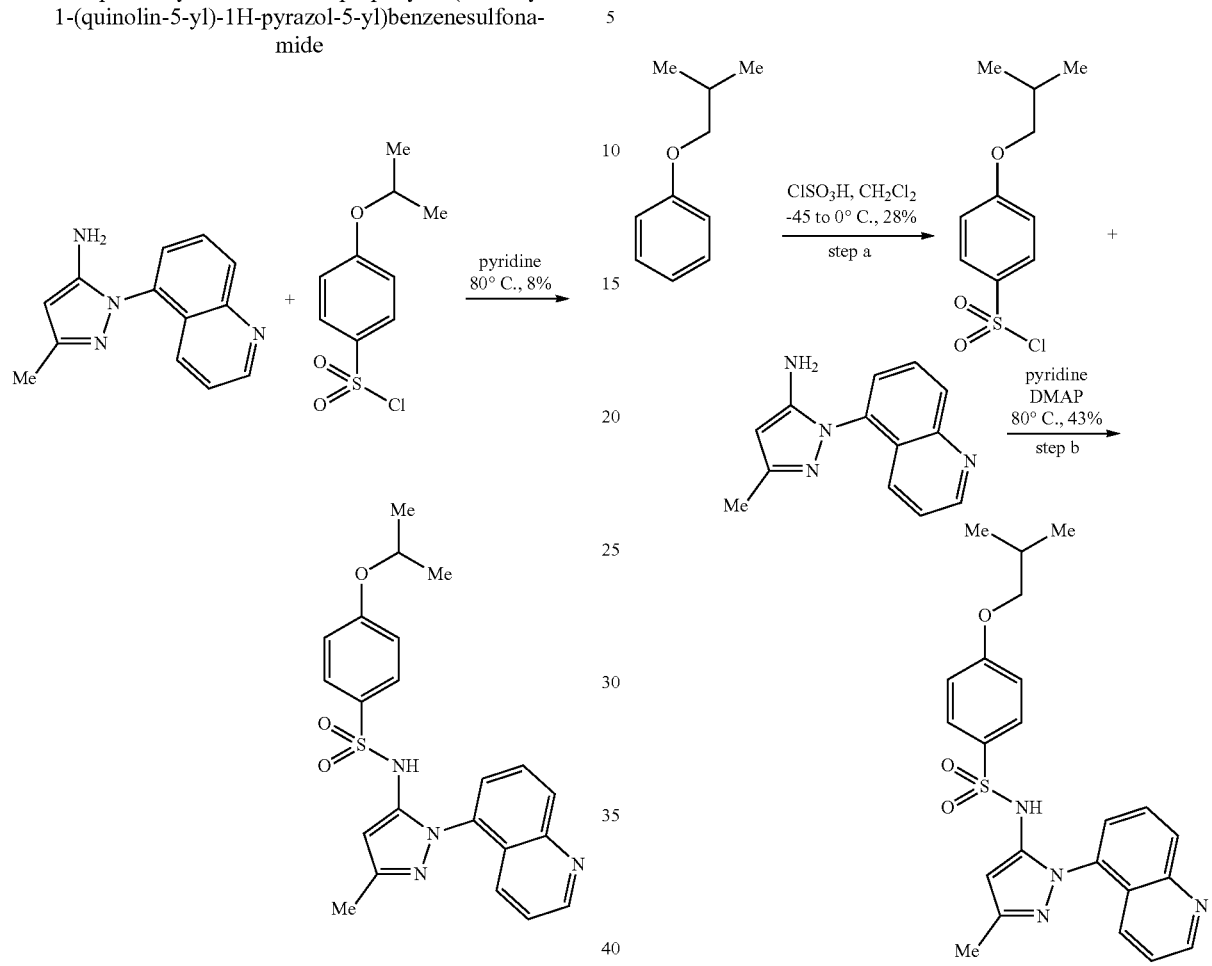

A stirred mixture of 4-isopropoxybenzene-1-sulfonyl chloride (0.10 g, 0.52 mmol) and 3-methyl-1-(quinolin-5-yl)-1H-pyrazol-5-amine (prepared from Example 4 step b, 0.10 g, 0.44 mmol) in pyridine (2 mL) was heated at 80° C. for 1 h. After cooling to room temperature, aqueous saturated sodium bicarbonate was added to the reaction mixture and extracted with dichloromethane. The organic layer was dried (Na$_2$SO$_4$), filtered, and concentrated in vacuo. The crude residue was purified by flash chromatography (SiO$_2$, 2-10% methanol in dichloromethane), followed by reverse phase HPLC (C18 column, acetonitrile-H$_2$O with 0.1% TFA as eluent) to give the title compound as a white solid (0.015 g, 0.036 mmol, 8%). $^1$H NMR (400 MHz, CDCl$_3$) δ 8.58 (dd, J=2.0, 4.0 Hz, 1H), 8.09 (d, J=8.4 Hz, 1H), 7.61 (dd, J=7.6, 8.4 Hz, 1H), 7.50 (d, J=2.0 Hz, 1H), 7.48 (d, J=1.6 Hz, 1H), 7.25-7.21 (m, 2H), 7.14 (dd, J=0.8, 7.2 Hz, 1H), 6.74 (d, J=2.4 Hz, 1H), 6.72 (d, J=2.0 Hz, 1H), 6.25 (s, 1H), 4.57 (hept, J=6.0 Hz, 1H), 2.33 (s, 3H), 1.39 (d, J=6.4 Hz, 6H); MS: (ES) m/z calculated for C$_{23}$H$_{23}$N$_4$O$_3$S [M+H]$^+$ 423.2, found 423.0.

a) To a stirring solution of isobutoxybenzene (0.60 g, 4.0 mmol) in dichloromethane (5 mL) at −45° C. was added chlorosulfonic acid (0.6 mL, 9.1 mmol) dropwise, and the reaction mixture was stirred at −45° C. for 1 h. The reaction mixture was then warmed to 0° C. and additional chlorosulfonic acid (0.6 mL, 9.1 mmol) was added dropwise. The reaction mixture was then stirred at 0° C. for 1 h and poured into ice. The aqueous layer was extracted with ethyl acetate and the organic layer was dried (Na$_2$SO$_4$), filtered, and concentrated in vacuo. The crude residue was purified by flash chromatography (SiO$_2$, 5-10% ethyl acetate in hexanes) to give 4-isobutoxybenzene-1-sulfonyl chloride (0.32 g, 1.1 mmol, 28%).

b) A stirred mixture of 4-isobutoxybenzene-1-sulfonyl chloride (0.060 g, 0.24 mmol), 3-methyl-1-(quinolin-5-yl)-1H-pyrazol-5-amine (prepared from Example 4 step b, 0.050 g, 0.22 mmol), and 4-(dimethylamino)pyridine (DMAP, 0.025 g, 0.20 mmol) in pyridine (2 mL) was heated at 80° C. for 2 h. After cooling to room temperature, aqueous saturated sodium bicarbonate was added to the reaction mixture and extracted with dichloromethane. The organic layer was dried (Na$_2$SO$_4$), filtered, and concentrated in vacuo. The crude residue was purified by flash chromatography (SiO$_2$, 2-5% methanol in dichloromethane), followed by reverse phase HPLC (C18 column, acetonitrile-H$_2$O with 0.1% TFA as eluent) to give the title compound as a white solid (0.041 g, 0.094 mmol, 43%). ¹H NMR (400 MHz, CDCl₃) δ 8.84 (d, J=4.0 Hz, 1H), 8.11 (d, J=8.0 Hz, 1H), 7.63 (t, J=8.0 Hz, 1H), 7.48-7.44 (m, 2H), 7.23 (d, J=4.0, Hz, 1H), 7.21 (d, J=4.0, Hz, 1H), 7.15 (dd, J=1.2, 7.2 Hz, 1H), 6.72 (d, J=2.4 Hz, 1H), 6.70 (d, J=2.4 Hz, 1H), 6.25 (s, 1H), 3.72 (dd, J=2.0, 6.4 Hz, 2H), 2.33 (s, 3H), 2.13 (hept, J=6.4 Hz, 1H), 1.08 (dd, J=2.4, 6.4 Hz, 6H); MS: (ES) m/z calculated for $C_{23}H_{25}N_4O_2S$ [M+H]⁺ 437.2, found 437.0.

Example 10: Synthesis of N-(3-methyl-1-(quinolin-5-yl)-1H-pyrazol-5-yl)-4-t-pentylbenzenesulfonamide

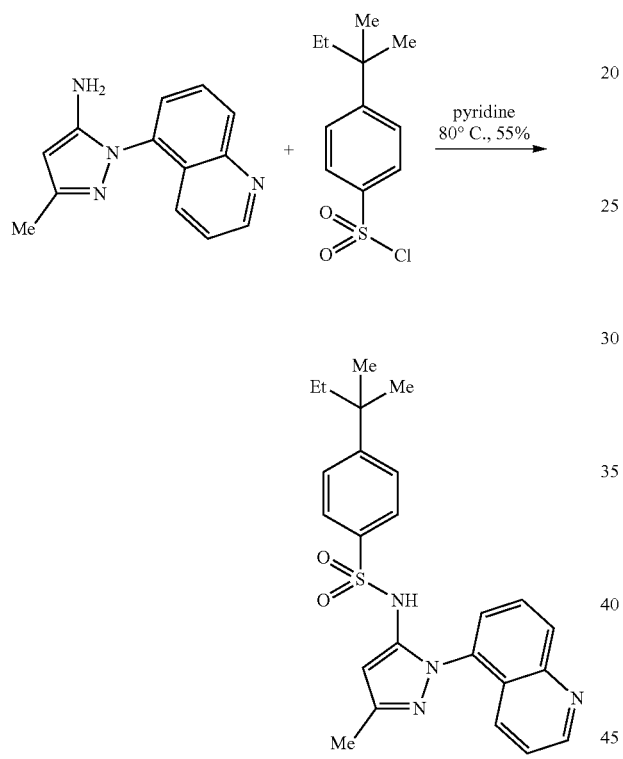

A mixture of 4-t-pentylbenzenesulfonyl chloride (0.13 g, 0.53 mmol) and 3-methyl-1-(quinolin-5-yl)-1H-pyrazol-5-amine (prepared from Example 4 step b, 0.10 g, 0.44 mmol) in pyridine (1.0 mL) was heated at 80° C. for 3 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na₂SO₄), filtered, and concentrated in vacuo. The crude residue was purified by reverse phase HPLC (C18 column, acetonitrile-H₂O with 0.1% TFA as eluent) to give the title compound as a white solid (0.11 g, 0.24 mmol, 55%). ¹H NMR (400 MHz, CDCl₃) δ 8.96 (dd, J=1.6, 4.8 Hz, 1H), 8.20 (d, J=8.8 Hz, 1H), 8.13 (d, J=8.4 Hz, 1H), 7.75 (d, J=7.6 Hz, 1H), 7.71 (s, 1H), 7.69 (s, 1H), 7.54 (dd, J=4.8, 8.4 Hz, 1H), 7.46-7.43 (m, 3H), 6.02 (s, 1H), 2.32 (s, 3H), 1.70 (q, J=7.2 Hz, 2H), 1.34 (s, 6H), 0.70 (t, J=7.2 Hz, 3H); MS: (ES) m/z calculated for $C_{24}H_{27}N_4O_2S$ [M+H]⁺ 435.2, found 435.1.

Example 11: Synthesis of 4-(2-hydroxypropan-2-yl)-N-(3-methyl-1-(quinolin-5-yl)-1H-pyrazol-5-yl)benzenesulfonamide

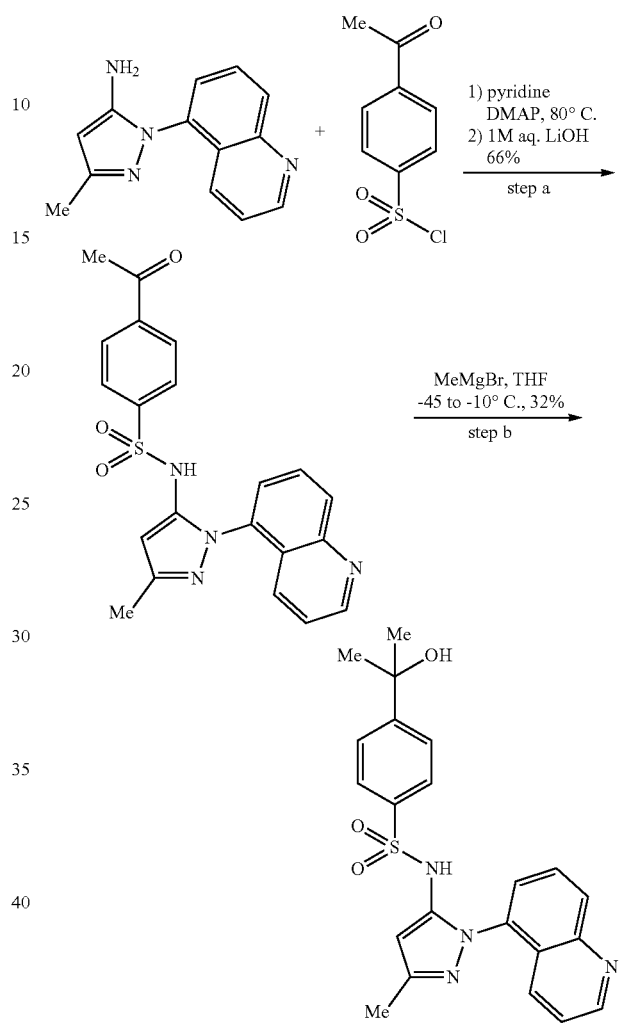

a) A mixture of 4-acetylbenzene-1-sulfonyl chloride (0.050 g, 0.22 mmol), 3-methyl-1-(quinolin-5-yl)-1H-pyrazol-5-amine (prepared from Example 4 step b, 0.060 g, 0.27 mmol), and DMAP (0.027 g, 0.22 mmol) in pyridine (2 mL) was heated at 80° C. for 2.5 h with stirring. After cooling to room temperature, 1 M aqueous lithium hydroxide (2 mL) was added to the reaction mixture and stirred for 2 h. The solution was added 4:1 dichloromethane/methanol and washed with 1 M aqueous ammonium chloride (5 mL). The solution was adjusted to pH ~8-9 with ammonium hydroxide and the phases were separated. The organic layer was dried (Na₂SO₄), filtered, and concentrated in vacuo. The crude residue was purified by flash chromatography (SiO₂, 2-5% methanol in dichloromethane). The product was then recrystallized in minimal amount of 4:1 dichloromethane/methanol and the solid was collected by filtration to give the desired solid (0.059 g, 0.15 mmol, 66%).

b) A solution of methyl magnesium bromide (1.4 M solution in 3:1 toluene/THF, 1.4 mL, 2.0 mmol) was added to a flask containing 4-acetyl-N-(3-methyl-1-(quinolin-5-yl)-1H-pyrazol-5-yl)benzenesulfonamide (0.059 g, 0.15 mmol) in THF (6 mL) at −45° C. with stirring. The reaction mixture was slowly warmed to −10° C. over 1 h and 4:1 dichloromethane/methanol was added (2 mL). The organic layer was washed with aqueous saturated ammonium chloride, dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.020 g, 0.047 mmol, 32%). $^1$H NMR (400 MHz, CD$_3$OD) δ 8.81 (d, J=4.4 Hz, 1H), 8.05 (d, J=8.8 Hz, 1H), 7.54 (t, J=8.0 Hz, 1H), 7.69 (d, J=8.0 Hz, 1H), 7.67 (s, 1H), 7.65 (s, 1H), 7.51-7.47 (m, 3H), 7.36 (dd, J=4.4, 8.4 Hz, 1H), 5.73 (s, 1H), 2.15 (s, 3H), 1.56 (s, 6H); MS: (ES) m/z calculated for C$_{22}$H$_{23}$N$_4$O$_3$S [M+H]$^+$ 433.2, found 433.0.

Example 12: Synthesis of 2,2-dimethyl-N-(3-methyl-1-(quinolin-5-yl)-1H-pyrazol-5-yl)-2,3-dihydrobenzofuran-5-sulfonamide

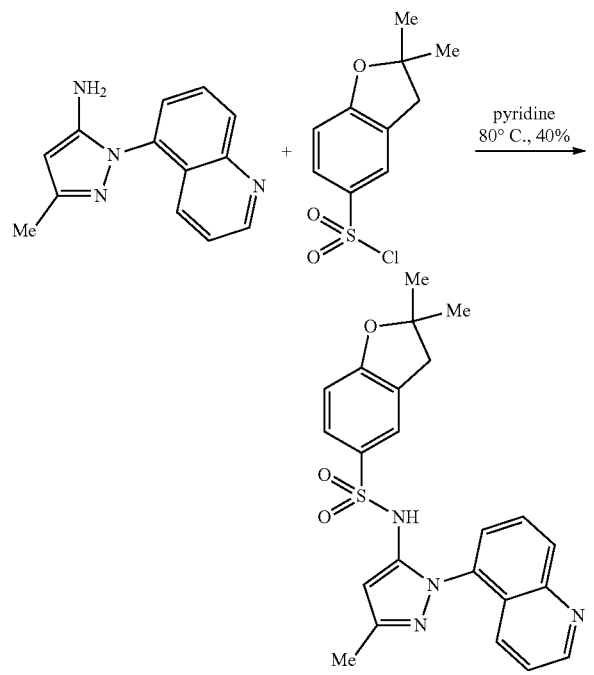

A stirring mixture of 2,2-dimethyl-2,3-dihydro-1-benzofuran-5-sulfonyl chloride (0.10 g, 0.41 mmol) and 3-methyl-1-(quinolin-5-yl)-1H-pyrazol-5-amine (prepared from Example 4 step b, 0.11 g, 0.49 mmol) in pyridine (0.41 mL) was heated at 80° C. for 1 h. After cooling to room temperature, the reaction mixture was concentrated in vacuo. The crude residue was purified by flash chromatography (SiO$_2$, 0-20% ethyl acetate in hexanes), followed by reverse phase HPLC (C18 column, acetonitrile-H$_2$O with 0.1% TFA as eluent) to give the title compound as a white solid (0.070 g, 0.16 mmol, 40%). $^1$H NMR (400 MHz, CDCl$_3$) δ 8.82 (s, 1H), 8.06 (d, J=8.0 Hz, 1H), 7.60 (t, J=7.6 Hz, 1H), 7.54 (d, J=8.0 Hz, 1H), 7.42 (d, J=8.4 Hz, 1H), 7.31 (s, 1H), 7.24 (d, J=3.2 Hz, 1H), 7.19 (d, J=6.8 Hz, 1H), 6.61 (d, J=8.8 Hz, 1H), 6.24 (s, 1H), 2.89 (s, 2H), 2.34 (s, 3H), 1.51 (s, 6H); MS: (ES) m/z calculated for C$_{23}$H$_{23}$N$_4$O$_3$S [M+H]$^+$ 435.2, found 435.3.

Example 13: Synthesis of 2,2-dimethyl-N-(3-methyl-1-(quinolin-5-yl)-1H-pyrazol-5-yl)chroman-6-sulfonamide

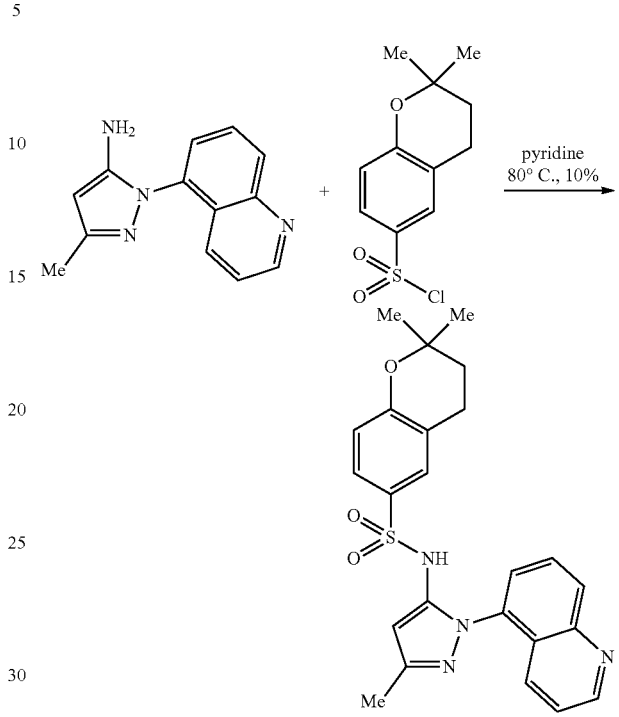

A stirring mixture of 2,2-dimethylchroman-6-sulfonyl chloride (0.050 g, 0.22 mmol) and 3-methyl-1-(quinolin-5-yl)-1H-pyrazol-5-amine (prepared from Example 4 step b, 0.068 g, 0.26 mmol) in pyridine (1.0 mL) was heated at 80° C. for 15 h. After cooling to room temperature, dichloromethane was added to the reaction mixture and washed with 1 M aqueous saturated bisulfate (1 mL). The aqueous layer was further extracted with dichloromethane (2×5 mL), and the combined organic layers were dried (Na$_2$SO$_4$), filtered, and concentrated in vacuo. The resulting crude residue was purified by flash chromatography (SiO$_2$, 0-20% ethyl acetate in hexanes), followed by reverse phase HPLC (C18 column, acetonitrile-H$_2$O with 0.1% TFA as eluent) to give the title compound as a white solid (0.010 g, 0.022 mmol, 10%). $^1$H NMR (400 MHz, CDCl$_3$) δ 9.09 (d, J=4.8 Hz, 1H), 8.38 (d, J=8.4 Hz, 1H), 8.29 (d, J=8.4 Hz, 1H), 7.87 (t, J=7.6 Hz, 1H), 7.66 (dd, J=4.8, 8.8 Hz, 1H), 7.61 (d, J=7.6 Hz, 1H), 7.40-7.38 (m, 2H), 6.72 (d, J=9.2 Hz, 1H), 6.09 (s, 1H), 2.71 (t, J=6.4 Hz, 2H), 2.34 (s, 3H), 1.83 (t, J=6.4 Hz, 2H), 1.36 (s, 6H); MS: (ES) m/z calculated for C$_{24}$H$_{25}$N$_4$O$_3$S [M+H]$^+$ 449.2, found 449.1.

Example 14: Synthesis of 1,1-dimethyl-N-(3-methyl-1-(quinolin-5-yl)-1H-pyrazol-5-yl)-2,3-dihydro-1H-indene-5-sulfonamide

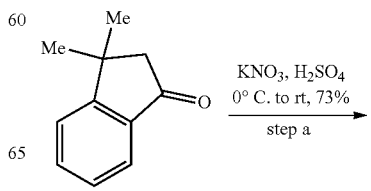

-continued

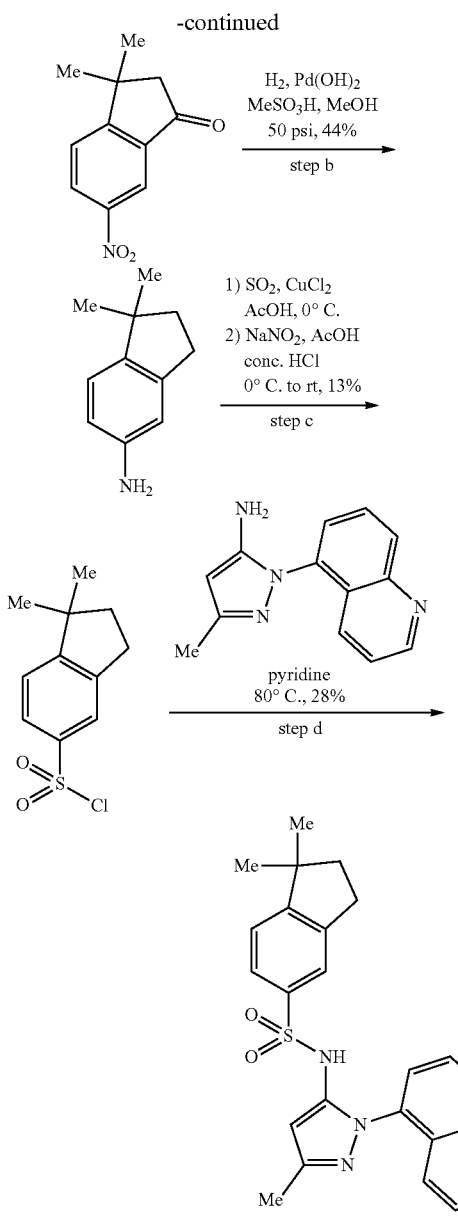

a) To a stirring solution of 3,3-dimethyl-1-indanone (0.10 g, 0.64 mmol) in sulfuric acid (0.63 mL) at 0° C. was added potassium nitrate (KNO₃, 0.063 g, 0.63 mmol) in sulfuric acid (0.2 mL). The reaction mixture was stirred at 0° C. for 1 h, then warmed to room temperature and stirred for 15 h. The reaction mixture was quenched with ice and the aqueous layer was extracted with ethyl acetate. The organic layer was dried (Na₂SO₄), filtered, and concentrated in vacuo. The crude residue was purified by flash chromatography (SiO₂, 20% ethyl acetate in hexanes) to give the desired product (0.096 g, 0.47 mmol, 73%).

b) In a Parr shaker flask containing 3,3-dimethyl-6-nitro-1-indanone (1.0 g, 4.8 mmol) and palladium hydroxide on carbon (Pd(OH)₂, 20% by weight, 0.52 g) in methanol (2 mL) and methane sulfonic acid (MeSO₃H, 0.4 mL, 6.2 mmol) was hydrogenated at 50 psi for 1.5 h. The reaction mixture was diluted with methanol and filtered through a pad of Celite. The filtrate was concentrated in vacuo and the resulting crude residue was purified by flash chromatography (SiO₂, 100% ethyl acetate) to give the desired product (0.34 g, 2.1 mmol, 44%).

c) To a solution of glacial acetic acid (8 mL) at 0° C. was bubbled in sulfur dioxide gas (SO₂) for 30 min. Copper(II) chloride (CuCl₂, 0.29 g, 2.16 mmol) was added to the reaction mixture and stirred for 30 min at 0° C. to give a blue/green solution. To another flask containing 1,1-dimethylindan-5-amine (0.34 g, 2.13 mmol) in concentrated hydrochloric acid (4.2 mL) at 0° C. was added NaNO₂ (0.22 g, 3.2 mmol) and stirred for 30 min. This diazonium solution was then slowly added to the prepared copper solution and stirred at 0° C. for 30 min. The reaction mixture was then slowly heated to 70° C. over 2 h. After cooling to room temperature, the reaction mixture was quenched with deionized water and the aqueous layer was extracted with ethyl acetate (2×10 mL). The combined organic layers were dried (Na₂SO₄), filtered, and concentrated in vacuo. The crude residue was purified by flash chromatography (SiO₂, 0-10% ethyl acetate in hexanes) to afford the desired product (0.067 g, 0.27 mmol, 13%).

d) A mixture of 1,1-dimethylindan-5-sulfonyl chloride (0.030 g, 0.13 mmol) and 3-methyl-1-(quinolin-5-yl)-1H-pyrazol-5-amine (prepared from Example 4 step b, 0.028 g, 0.12 mmol) in pyridine (0.12 mL) was heated at 80° C. for 1 h with stirring. After cooling to room temperature, the reaction mixture was concentrated in vacuo. The resulting crude residue was purified by flash chromatography (SiO₂, 20% ethyl acetate in hexanes), followed by reverse phase HPLC (C18 column, acetonitrile-H₂O with 0.1% TFA as eluent) to give the title compound as a white solid (0.015 g, 0.036 mmol, 28%). $^1$H NMR (400 MHz, DMSO-d₆) δ 10.30 (s, 1H), 8.90 (d, J=3.2 Hz, 1H), 8.06 (d, J=8.4 Hz, 1H), 7.73 (t, J=8.0 Hz, 1H), 7.57 (d, J=9.2 Hz, 1H), 7.46 (dd, J=4.0, 8.4 Hz, 1H), 7.30-7.26 (m, 2H), 7.18 (s, 1H), 7.11 (d, J=8.0 Hz, 1H), 6.05 (s, 1H), 2.71 (d, J=7.6 Hz, 2H), 2.20 (s, 3H), 1.84 (d, J=7.2 Hz, 2H), 1.18 (s, 6H); MS: (ES) m/z calculated for C₂₄H₂₅N₄O₂S [M+H]+ 433.2, found 433.1.

Example 15: Synthesis of 3-fluoro-N-(3-methyl-1-(quinolin-5-yl)-1H-pyrazol-5-yl)-4-morpholinobenzenesulfonamide

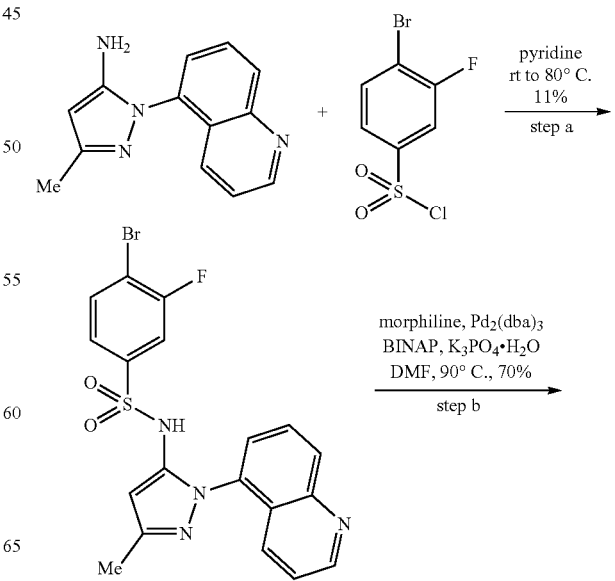

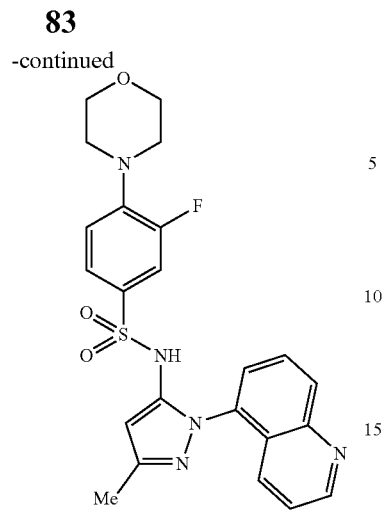

a) A mixture of 4-bromo-3-fluorobenzene-1-sulfonyl chloride (1.4 g, 5.2 mmol) and 3-methyl-1-(quinolin-5-yl)-1H-pyrazol-5-amine (prepared from Example 4 step b, 0.90 g, 4.0 mmol) in pyridine (10 mL) was stirred at room temperature for 2 h, then heated at 80° C. for 2 h. After cooling to room temperature, 1 N aqueous hydrochloric acid (1 mL) was added to the reaction mixture and extracted with dichloromethane (2×5 mL). The combined organic layers were dried (Na$_2$SO$_4$), filtered, and concentrated in vacuo. The crude residue was purified by flash chromatography (SiO$_2$, 0-10% methanol in ethyl acetate to give the desired product (0.20 g, 0.43 mmol, 11%).

b) A stirring mixture of 4-bromo-3-fluoro-N-(3-methyl-1-(quinolin-5-yl)-1H-pyrazol-5-yl)benzenesulfonamide (0.07 g, 0.15 mmol), morpholine (0.066 g, 0.75 mmol), tris(dibenzylideneacetone)dipalladium(0) (Pd$_2$(dba)$_3$, 0.007 g, 0.008 mmol), 2,2'-bis(diphenylphosphino)-1,1'-binaphthyl (BINAP, 0.014 g, 0.023 mmol), and potassium phosphate monobasic (K$_3$PO$_4$·H$_2$O, 0.21 g, 0.90 mmol) in anhydrous N,N-dimethylformamide (DMF, 6 mL) was purged with nitrogen for 5 min. The reaction mixture was heated at 90° C. for 4 h. After cooling to room temperature, ethyl acetate (10 mL) was added to the reaction mixture and washed with aqueous saturated sodium bicarbonate. The organic layer was dried (Na$_2$SO$_4$), filtered, and concentrated in vacuo. The resulting crude material was purified by reverse phase HPLC (C18 column, acetonitrile-H$_2$O with 0.1% TFA as eluent) to give the title compound as a white solid (0.049 g, 0.11 mmol, 70%). $^1$H NMR (400 MHz, CDCl$_3$) δ 9.06 (dd, J=1.6, 4.8 Hz, 1H), 8.36 (d, J=8.4 Hz, 1H), 8.31 (d, J=8.0 Hz, 1H), 7.88 (dd, J=8.4, 9.6 Hz, 1H), 7.68 (d, J=4.8 Hz, 1H), 7.66 (d, J=6.4 Hz, 1H), 7.37 (dd, J=1.6, 8.4 Hz, 1H), 7.31 (dd, J=2.4, 12.4 Hz, 1H), 6.80 (t, J=6.8 Hz, 1H), 6.09 (s, 1H), 3.90-3.86 (m, 4H), 3.21-3.18 (m, 4H), 2.35 (s, 3H); MS: (ES) m/z calculated for C$_{23}$H$_{23}$FN$_5$O$_3$S [M+H$^+$ 468.2, found 468.2.

Example 16: Synthesis of 4-t-butyl-N-(1-(quinolin-5-yl)-1H-pyrazol-5-yl)benzenesulfonamide

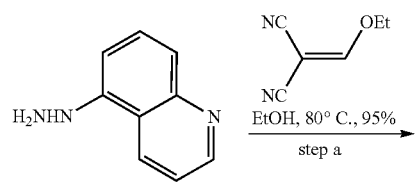

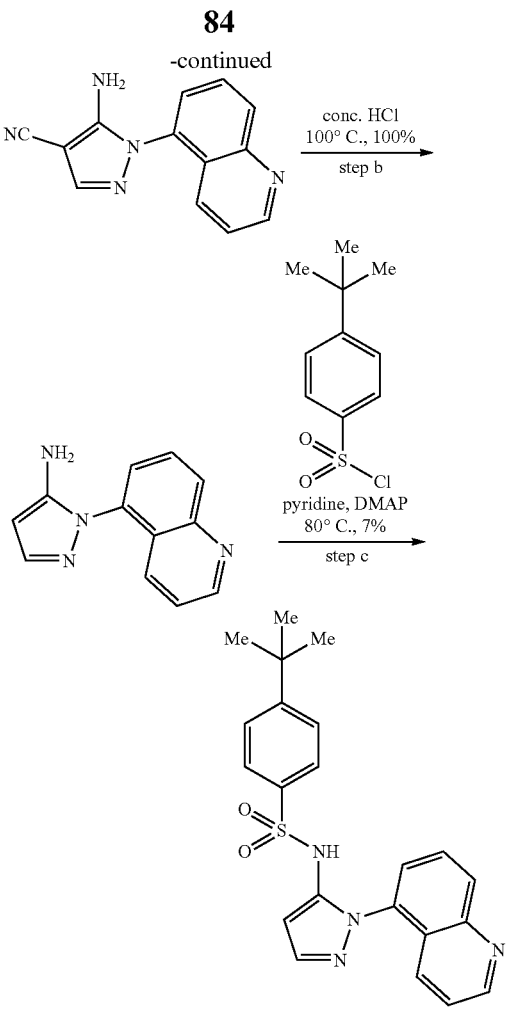

a) To a stirring solution of (ethoxymethylene)malononitrile (0.38 g, 3.2 mmol) and quinolin-5-yl-hydrazine (prepared from Example 4 step a, 0.5 g, 3.2 mmol) in ethanol (5 mL) was heated at 80° C. for 15 h. After cooling to room temperature, the reaction mixture was concentrated in vacuo and the crude solid was used directly without further purification (0.70 g, 3.0 mmol, 95%).

b) To a solution of crude 5-amino-1-(quinolin-5-yl)-1H-pyrazole-4-carbonitrile (0.40 g, 1.7 mmol) in concentrated hydrochloric acid (5 mL) was heated at 100° C. for 15 h with stirring. The reaction mixture was cooled to room temperature and basified with aqueous saturated sodium bicarbonate. The aqueous layer was extracted with 2:1 chloroform/iPrOH and the organic layer was dried (Na$_2$SO$_4$), filtered, and concentrated in vacuo. The crude residue was used directly without further purification (0.36 g, 1.7 mmol, 100%).

c) A stirred mixture of crude 1-(quinolin-5-yl)-1H-pyrazol-5-amine (0.080 g, 0.38 mmol), 4-t-butylbenzenesulfonyl chloride (0.13 g, 0.57 mmol), and DMAP (0.068 g, 0.57 mmol) in pyridine (1.5 mL) was heated at 80° C. for 2 h. After cooling to room temperature, aqueous saturated sodium bicarbonate was added to the reaction mixture and extracted with 2:1 chloroform/iPrOH. The organic layer was dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.010 g, 0.025 mmol, 7%). $^1$H NMR (400 MHz, CD$_3$OD) δ 8.87 (dd, J=2.0, 4.4

Hz, 1H), 8.13 (d, J=8.4 Hz, 1H), 7.76 (dd, J=7.2, 8.8 Hz, 1H), 7.69 (d, J=2.4 Hz, 1H), 7.65-7.62 (m, 1H), 7.52-7.42 (m, 3H), 7.51 (d, J=8.8 Hz, 1H), 7.43 (d, J=8.8 Hz, 1H), 7.28 (dd, J=1.2, 7.2 Hz, 1H), 6.25 (s, 1H), 1.35 (s, 9H); MS: (ES) m/z calculated for $C_{22}H_{23}N_4O_2S$ [M+H]+ 407.2, found 407.0.

Example 17: Synthesis of 4-t-butyl-N-(3-ethyl-1-(quinolin-5-yl)-1H-pyrazol-5-yl)benzenesulfonamide

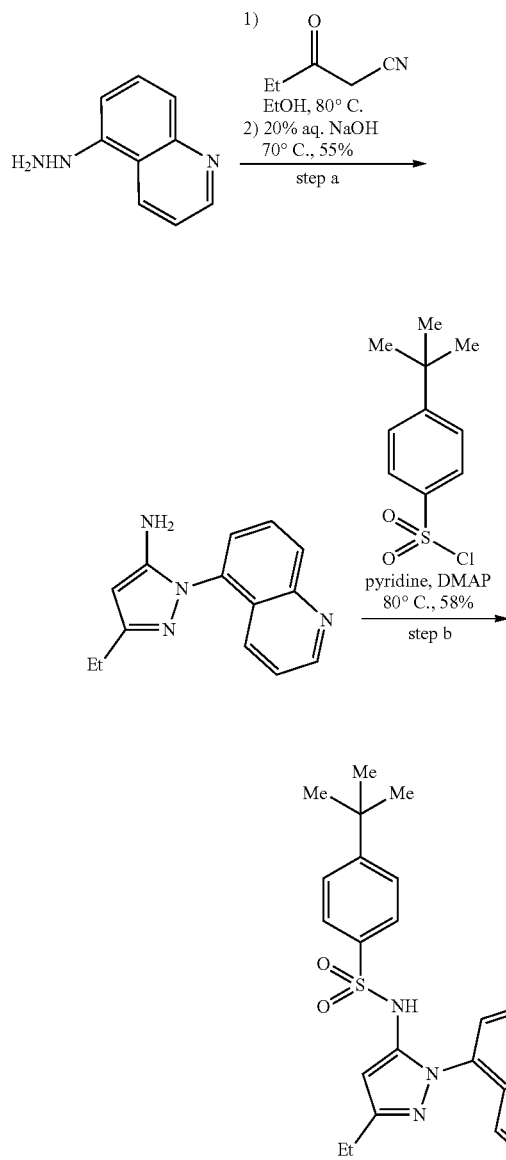

a) To a solution of 3-oxopentanenitrile (0.74 g, 7.6 mmol) and quinolin-5-yl-hydrazine (prepared from Example 4 step a, 1.0 g, 6.3 mmol) in ethanol (5 mL) was heated at 80° C. for 3 h with stirring. After cooling to room temperature, 20% aqueous sodium hydroxide (1.5 mL) was added to the reaction mixture and then heated at 70° C. for 3 h. The reaction mixture was cooled to room temperature and concentrated in vacuo. The crude residue was dissolved in 1:1 dichloromethane/methanol (40 mL) and the phases were separated. The organic layer was dried (Na$_2$SO$_4$), and filtered through a pad of Celite. The filtrate was concentrated in vacuo and the crude residue was purified by flash chromatography (SiO$_2$, 1-10% methanol containing 10% ammonium hydroxide in dichloromethane) to give the desired product (0.83 g, 3.5 mmol, 55%).

b) A mixture of 4-t-butylbenzenesulfonyl chloride (0.064 g, 0.27 mmol) and 3-ethyl-1-(quinolin-5-yl)-1H-pyrazol-5-amine (0.05 g, 0.21 mmol) in pyridine (0.5 mL) was heated at 80° C. for 15 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was dissolved in methanol (3 mL) and 1 M aqueous sodium hydroxide (1.0 mL, 1.0 mmol). The reaction mixture was stirred at room temperature for 1 h and the solvent was removed in vacuo. The resulting residue was partitioned between dichloromethane (3 mL) and 1 M aqueous sodium hydrogen sulfate (3 mL) and the phases were separated. The aqueous layer was extracted with dichloromethane (2×5 mL), and the combined organic layers were dried (Na$_2$SO$_4$), filtered, and concentrated in vacuo. The crude residue was purified by reverse phase HPLC (C18 column, acetonitrile-H$_2$O with 0.1% TFA as eluent) to give the title compound as a white solid (0.053 g, 0.12 mmol, 58%). $^1$H NMR (400 MHz, CDCl$_3$) δ 9.00 (d, J=3.6 Hz, 1H), 8.23 (d, J=8.8 Hz, 1H), 8.19 (d, J=8.0 Hz, 1H), 7.79 (dd, J=8.0, 8.4 Hz, 1H), 7.69-7.65 (m, 2H), 7.59 (dd, J=4.4, 8.8 Hz, 1H), 7.51-7.47 (m, 3H), 6.05 (s, 1H), 2.69 (q, J=7.6 Hz, 2H), 1.37 (s, 9H), 1.29 (t, J=7.6 Hz, 3H); MS: (ES) m/z calculated for $C_{24}H_{27}N_4O_2S$ [M+H]$^+$ 435.2, found 435.2.

Example 18: Synthesis of 4-t-butyl-N-(3-cyclopropyl-1-(quinolin-5-yl)-1H-pyrazol-5-yl)benzenesulfonamide

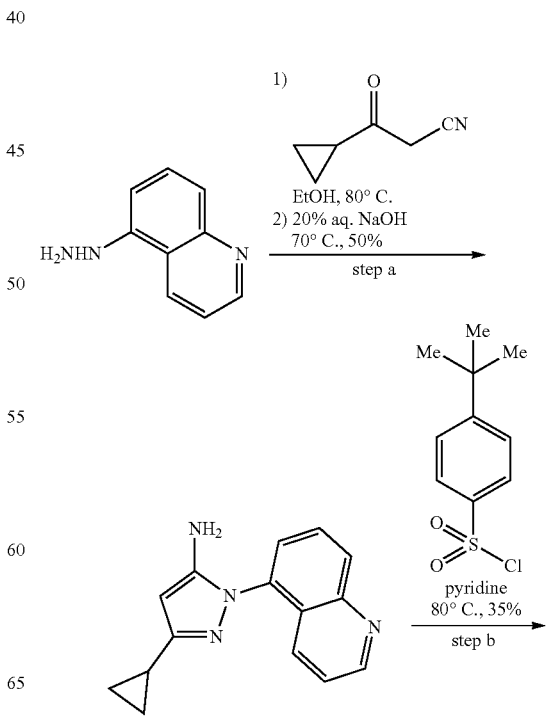

87
-continued

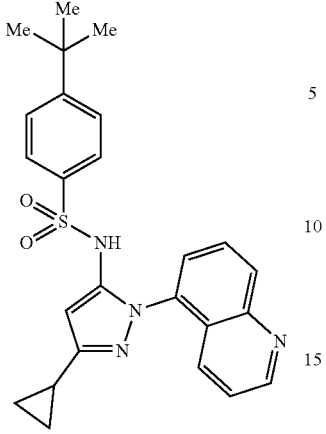

a) To a solution of 3-cyclopropyl-3-oxopropanenitrile (0.74 g, 7.6 mmol) and quinolin-5-yl-hydrazine (prepared from Example 4 step a, 1.0 g, 6.3 mmol) in ethanol (5 mL) was heated at 80° C. for 3 h with stirring. After cooling to room temperature, 20% aqueous sodium hydroxide (1.5 mL) was added to the reaction mixture and heated at 70° C. for 3 h. The mixture was cooled to room temperature and concentrated in vacuo. The crude residue was dissolved in 1:1 dichloromethane/methanol (40 mL) and the phases were separated. The organic layer was dried ($Na_2SO_4$), and filtered through a pad of Celite. The filtrate was concentrated in vacuo and the crude material was purified by flash chromatography ($SiO_2$, 1-10% methanol containing 10% ammonium hydroxide in dichloromethane) to give the desired product (0.80 g, 3.2 mmol, 50%).

b) A mixture of 4-t-butylbenzenesulfonyl chloride (0.061 g, 0.26 mmol) and 3-cyclopropyl-1-(quinolin-5-yl)-1H-pyrazol-5-amine (0.05 g, 0.20 mmol) in pyridine (1 mL) was heated at 80° C. for 15 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried ($Na_2SO_4$), filtered, and concentrated in vacuo. The resulting crude residue was dissolved in methanol (3 mL) and 1 M aqueous sodium hydroxide (1.0 mL, 1.0 mmol) and stirred at room temperature for 1 h. The reaction mixture was concentrated in vacuo and the resulting residue was partitioned between dichloromethane (3 mL) and 1 M aqueous sodium hydrogen sulfate (3 mL). The phases were separated and the aqueous layer was extracted with dichloromethane (2×5 mL). The combined organic layers were dried ($Na_2SO_4$), filtered, and concentrated in vacuo. The crude residue was purified by reverse phase HPLC (C18 column, acetonitrile-$H_2O$ with 0.1% TFA as eluent) to give the title compound as a white solid (0.031 g, 0.070 mmol, 35%). $^1$H NMR (400 MHz, $CDCl_3$) δ 8.84 (d, J=4.0 Hz, 1H), 8.08 (d, J=8.0 Hz, 1H), 7.55-7.51 (m, 5H), 7.41 (s, 1H), 7.39 (s, 1H), 6.94 (d, J=7.2 Hz, 1H), 6.12 (s, 1H), 1.99-1.93 (m, 1H), 1.36 (s, 9H), 1.01-0.92 (m, 2H), 0.84-0.79 (m, 2H); MS: (ES) m/z calculated for $C_{25}H_{27}N_4O_2S$ [M+H]$^+$ 447.2, found 447.2.

88

Example 19: Synthesis of 4-t-butyl-N-(3-(cyanomethyl)-1-(quinolin-5-yl)-1H-pyrazol-5-yl)benzenesulfonamide

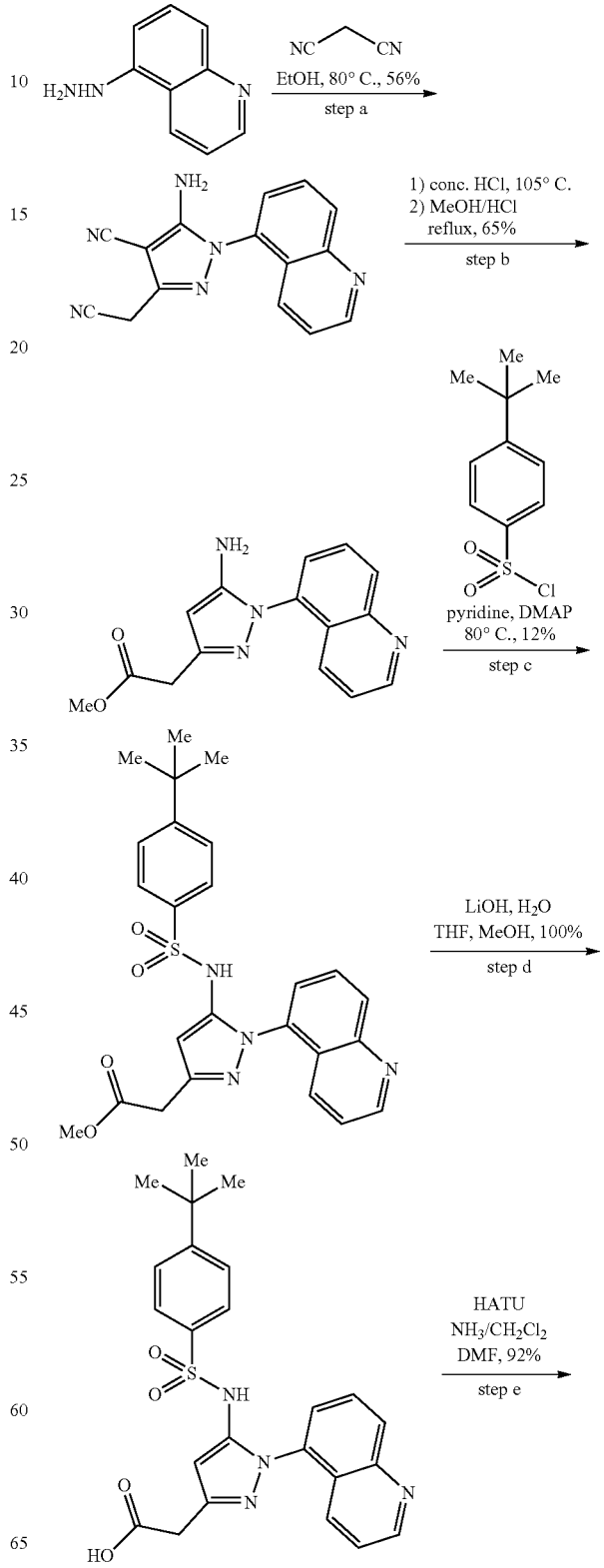

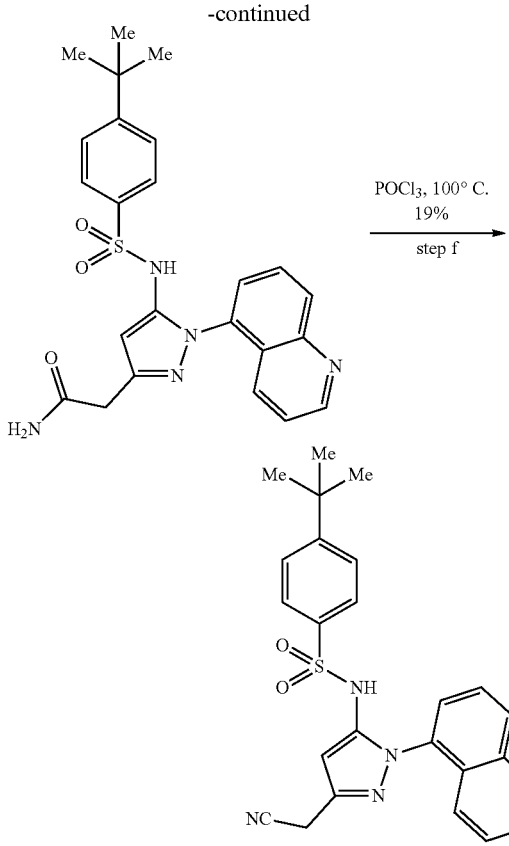

a) To a stirring solution of quinolin-5-yl-hydrazine (prepared from Example 4 step a, 0.62 g, 3.9 mmol) in ethanol (4 mL) was added malononitrile (0.51 g, 7.7 mmol). The reaction mixture was heated at 80° C. for 15 h. After cooling to room temperature, aqueous saturated ammonium chloride (1.5 mL) was added to the reaction mixture and extracted with 2:1 chloroform/iPrOH. The organic layer was washed with brine, dried (Na$_2$SO$_4$), filtered, and concentrated in vacuo. The crude residue was purified by flash chromatography (SiO$_2$, 0-5% methanol in dichloromethane) to give the desired product as a light-brown solid (0.60 g, 2.2 mmol, 56%).

b) To a solution of 5-amino-3-(cyanomethyl)-1-(quinolin-5-yl)-1H-pyrazole-4-carbonitrile (0.60 g, 2.2 mmol) in concentrated hydrochloric acid (50 mL) was heated at 105° C. for 22 h with stirring. The reaction mixture was cooled to room temperature and the solution was concentrated in vacuo. Methanol (50 mL) and concentrated hydrochloric acid (0.5 mL) were added to the resulting residue, and the reaction mixture was refluxed for 3 h. After cooling to room temperature, the reaction mixture was basified with aqueous saturated sodium bicarbonate. The aqueous layer was extracted with 2:1 chloroform/iPrOH and the organic layer was extracted with aqueous saturated ammonium chloride, dried (Na$_2$SO$_4$), filtered, and concentrated in vacuo. The crude residue was used directly without further purification (0.40 g, 1.7 mmol, 65%).

c) A mixture of crude methyl 2-(5-amino-1-(quinolin-5-yl)-1H-pyrazol-3-yl)acetate (0.55 g, 2.0 mmol), 4-t-butylbenzenesulfonyl chloride (0.30 g, 1.3 mmol), and DMAP (0.12 g, 1.0 mmol) in pyridine (5 mL) was heated at 80° C. for 2 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na$_2$SO$_4$), filtered, and concentrated in vacuo. The crude residue was purified by reverse phase HPLC (C18 column, acetonitrile-H$_2$O with 0.1% TFA as eluent) to give a white solid (0.075 g, 0.16 mmol, 12%).

d) To a suspension of methyl 2-(5-(4-t-butylphenylsulfonamido)-1-(quinolin-5-yl)-1H-pyrazol-3-yl)acetate (0.066 g, 0.14 mmol) in THF (1 mL) and methanol (1 mL) was added a solution of lithium hydroxide (0.05 g, 2.1 mmol) in deionized water (0.5 mL). The reaction mixture was stirred at room temperature for 1 h and the resulting solution was adjusted to pH-5 with 5 N aqueous hydrochloric acid. The aqueous layer was extracted with 2:1 chloroform/iPrOH and the organic layer was washed with brine, dried (Na$_2$SO$_4$), filtered, and concentrated in vacuo. The crude material was used directly without further purification (0.065 g, 0.14 mmol, 100%).

e) To a stirred solution of crude 2-(5-(4-t-butylphenylsulfonamido)-1-(quinolin-5-yl)-1H-pyrazol-3-yl)acetic acid (0.065 g, 0.14 mmol) and N,N,N',N'-tetramethyl-O-(7-azabenzotriazol-1-yl)uronium hexafluorophosphate (HATU, 0.11 g, 0.28 mmol) in DMF (1.5 mL) was added a solution of saturated ammonia in dichloromethane (0.5 mL). The reaction mixture was stirred at room temperature for 1 h and brine was added. The aqueous layer was extracted with 2:1 chloroform/iPrOH and the organic layer was washed with brine, dried (Na$_2$SO$_4$), filtered, and concentrated in vacuo. The crude material was used directly without further purification (0.060 g, 0.14 mmol, 92%).

f) To a stirring solution of crude 2-(5-(4-t-butylphenylsulfonamido)-1-(quinolin-5-yl)-1H-pyrazol-3-yl)acetamide (0.03 g, 0.07 mmol) and phosphorus(V) oxide chloride (POCl$_3$, 0.5 mL, 5.4 mmol) was heated at 100° C. for 30 min. After cooling to room temperature, the reaction mixture was concentrated in vacuo. Aqueous saturated sodium bicarbonate was added to the resulting residue and extracted with 2:1 chloroform/iPrOH. The organic layer was dried (Na$_2$SO$_4$), filtered, and concentrated in vacuo. The crude product was purified by reverse phase HPLC (C18 column, acetonitrile-H$_2$O with 0.1% TFA as eluent) to give the title compound as a white solid (0.006 g, 0.013 mmol, 19%). $^1$H NMR (400 MHz, CD$_3$OD) δ 8.86 (dd, J=2.0, 4.4 Hz, 1H), 8.12 (d, J=8.4 Hz, 1H), 7.77 (dd, J=7.2, 8.4 Hz, 1H), 7.68 (d, J=8.4 Hz, 1H), 7.55-7.53 (m, 2H), 7.45-7.42 (m, 3H), 7.34 (dd, J=1.2, 7.2 Hz, 1H), 6.21 (s, 1H), 3.88 (s, 2H), 1.35 (s, 9H); MS: (ES) m/z calculated for C$_{24}$H$_{24}$N$_5$O$_2$S [M+H]$^+$ 446.2, found 446.3.

Example 20: Synthesis of 4-t-butyl-N-(1-(quinolin-5-yl)-3-(trifluoromethyl)-1H-pyrazol-5-yl)benzenesulfonamide

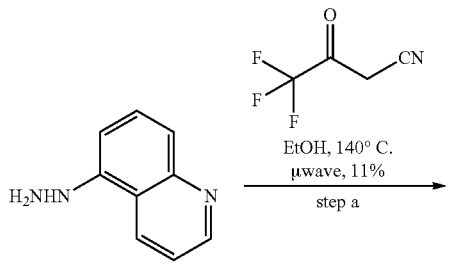

-continued

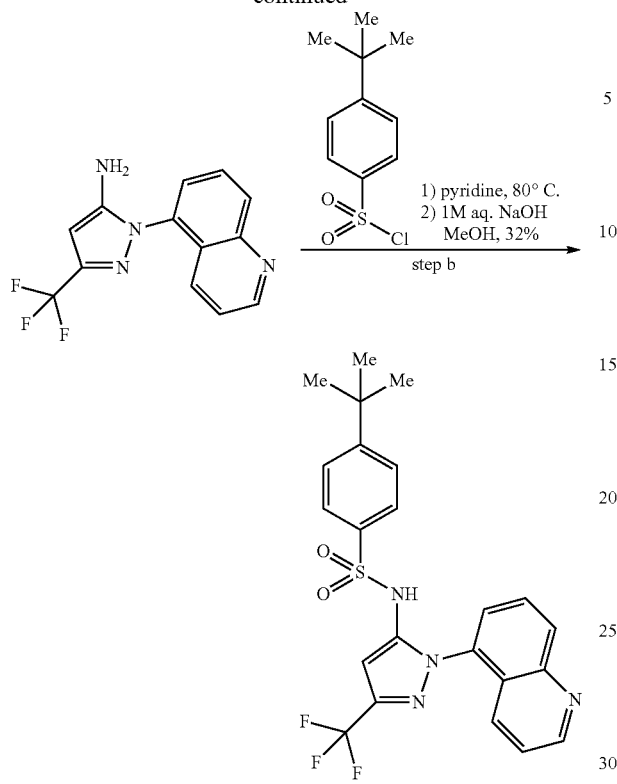

1H), 7.27-7.24 (m, 1H), 7.09 (d, J=6.0 Hz, 1H), 6.70 (s, 1H), 1.38 (s, 9H); MS: (ES) m/z calculated for $C_{23}H_{22}F_3N_4O_2S$ [M+H]+ 475.2, found 475.3.

Example 21: Synthesis of 4-isopropoxy-N-(1-(quinolin-5-yl)-3-(trifluoromethyl)-1H-pyrazol-5-yl)benzenesulfonamide

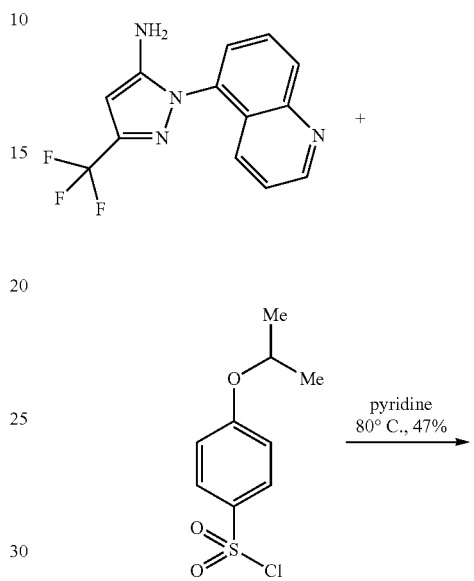

a) To a stirring solution of 4,4,4-trifluoro-3-oxobutanenitrile (0.40 g, 2.9 mmol) and quinolin-5-yl-hydrazine (prepared from Example 4 step a, 0.46 g, 2.9 mmol) in ethanol (3 mL) was heated at 140° C. in microwave for 40 min. After cooling to room temperature, the reaction mixture was concentrated in vacuo. The resulting crude residue was purified by flash chromatography (SiO₂, 5-60% ethyl acetate in hexanes) to give the desired product as a light-brown solid (0.087 g, 0.31 mmol, 11%).

b) To a mixture of 4-t-butylbenzenesulfonyl chloride (0.067 g, 0.29 mmol) and 1-(quinolin-5-yl)-3-(trifluoromethyl)-1H-pyrazol-5-amine (0.011 g, 0.04 mmol) in pyridine (0.5 mL) was heated at 80° C. for 2 h with stirring. After cooling to room temperature, dichloromethane was added to the reaction mixture and washed with 1 M aqueous sodium hydrogen sulfate (1 mL). The aqueous layer was further extracted with dichloromethane (2×5 mL), and the combined organic layers were dried (Na₂SO₄), filtered, and concentrated in vacuo. The crude residue was dissolved in methanol (3 mL) and 1 M aqueous sodium hydroxide (1.0 mL, 1.0 mmol), and stirred at room temperature for 1 h. The reaction mixture was concentrated in vacuo and partitioned between dichloromethane (3 mL) and 1 M aqueous sodium hydrogen sulfate (3 mL). The phases were separated and the aqueous layer was further extracted with dichloromethane (2×5 mL). The combined organic layers were dried (Na₂SO₄), filtered, and concentrated in vacuo. The crude residue was purified by reverse phase HPLC (C18 column, acetonitrile-H₂O with 0.1% TFA as eluent) to give the title compound as a white solid (0.006 g, 0.013 mmol, 32%). ¹H NMR (400 MHz, CDCl₃) δ 8.78 (dd, J=1.6, 4.4 Hz, 1H), 8.07 (d, J=8.4 Hz, 1H), 7.66 (s, 1H), 7.63 (s, 1H), 7.55 (t, J=8.4 Hz, 1H), 7.45 (s, 1H), 7.48 (s, 1H), 7.43 (d, J=6.0 Hz,

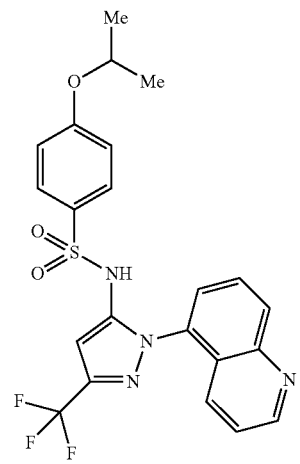 [SMILES: CC(C)Oc1ccc(S(=O)(=O)Nc2cc(C(F)(F)F)nn2-c2cccc3ncccc23)cc1]

To a mixture of 4-isopropoxybenzenesulfonyl chloride (0.080 g, 0.35 mmol) and 1-(quinolin-5-yl)-3-(trifluoromethyl)-1H-pyrazol-5-amine (prepared from Example 21 step a, 0.032 g, 0.11 mmol) in pyridine (0.5 mL) was heated at 80° C. for 4 h with stirring. After cooling to room temperature, the reaction mixture was concentrated in vacuo and the crude residue was purified by reverse phase HPLC (C18 column, acetonitrile-H₂O with 0.1% TFA as eluent) to give the title compound as a white solid (0.025 g, 0.052 mmol, 47%). ¹H NMR (400 MHz, DMSO-d₆) δ 8.94 (dd, J=1.6, 4.0 Hz, 1H), 8.19 (d, J=8.4 Hz, 1H), 7.82 (t, J=8.4 Hz, 1H), 7.50-7.46 (m, 2H), 7.40 (s, 1H), 7.38 (s, 1H), 7.35 (d, J=8.4 Hz, 1H), 6.83 (s, 1H), 6.81 (s, 1H), 6.64 (s, 1H), 4.63 (pent, J=6.0 Hz, 1H), 1.28 (d, J=6.0 Hz, 6H); MS: (ES) m/z calculated for $C_{27}H_{20}F_3N_4O_2S$ [M+H]⁺ 477.2, found 477.3.

Example 22: Synthesis of 4-t-butyl-N-(3-(1,1-difluoroethyl)-1-(quinolin-5-yl)-1H-pyrazol-5-yl)benzenesulfonamide

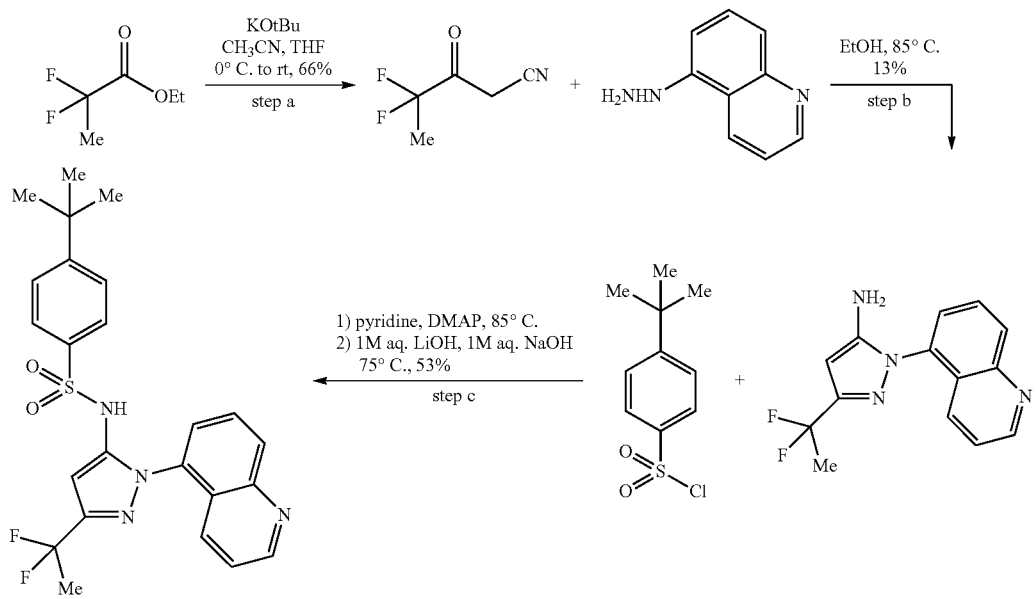

a) To a stirring solution of potassium t-butoxide (KOtBu, 1.7 M solution in THF, 32 mL, 54.4 mmol) in THF (10 mL) at 0° C. was added ethyl 2,2-difluoropropanoate (5.0 g, 36.2 mmol) and acetonitrile (2.8 mL, 54.3 mmol). The reaction mixture was warmed to room temperature and stirred for 18 h. Aqueous saturated potassium bisulfate was added to the reaction mixture and the pH was adjusted below 2. The aqueous layer was extracted with ethyl acetate (2×50 mL), and the combined organic layers were dried ($Na_2SO_4$), filtered, and concentrated in vacuo. The resulting brown crude oil was used directly without further purification (3.2 g, 24.1 mmol, 66%).

b) To a stirring solution of 5-hydrazinylquinoline (prepared from Example 4 step a, 0.90 g, 5.6 mmol) in ethanol (10 mL) was added crude 4,4-difluoro-3-oxopentanenitrile (0.75 g, 5.6 mmol) and heated at 85° C. for 6 h. After cooling to room temperature, ethyl acetate was added to the reaction mixture and washed with 5 M aqueous sodium hydroxide and brine. The organic layer was dried ($Na_2SO_4$), filtered, and concentrated in vacuo. The crude residue was purified by flash chromatography ($SiO_2$, 50-100% ethyl acetate in hexanes) to give the desired product (0.20 g, 0.73 mmol, 13%).

c) A mixture of 4-t-butylbenzene-1-sulfonyl chloride (0.080 g, 0.34 mmol), 3-(1,1-difluoroethyl)-1-(quinolin-5-yl)-1H-pyrazol-5-amine (0.045 g, 0.16 mmol), and DMAP (0.020 g, 0.16 mmol) in pyridine (1 mL) was heated at 85° C. for 5 h with stirring. After cooling to room temperature, 1 M aqueous lithium hydroxide (1 mL) and 1 M aqueous sodium hydroxide (1 mL) were added to the reaction mixture. The resulting mixture was heated at 75° C. for 1.5 h. After cooling to room temperature, the reaction mixture was neutralized with 1 N aqueous hydrochloric acid. The aqueous layer was extracted with ethyl acetate (2×10 mL). The combined organic layers were washed with aqueous saturated sodium bicarbonate, dried ($Na_2SO_4$), filtered, and concentrated in vacuo. The crude residue was purified by reverse phase HPLC (C18 column, acetonitrile-H₂O with 0.1% TFA as eluent) to give the title compound as a white solid (0.040 g, 0.085 mmol, 53%). ¹H NMR (400 MHz, CD₃OD) δ 10.70 (s, 1H), 8.88 (dd, J=1.6, 4.4 Hz, 1H), 8.14 (dd, J=1.2, 8.4 Hz, 1H), 7.77 (dd, J=7.2, 8.8 Hz, 1H), 7.64-7.61 (m, 2H), 7.52-7.42 (m, 5H), 7.31 (dd, J=1.2, 7.2 Hz, 1H), 1.96 (t, J=15.4 Hz, 3H), 1.35 (s, 9H); MS: (ES) m/z calculated for $C_{24}H_{25}F_2N_4O_2S$ [M+H]⁺ 471.2, found 471.2.

Example 23: Synthesis of 4-t-butyl-N-(3-(difluoromethyl)-1-(quinolin-5-yl)-1H-pyrazol-5-yl)benzenesulfonamide

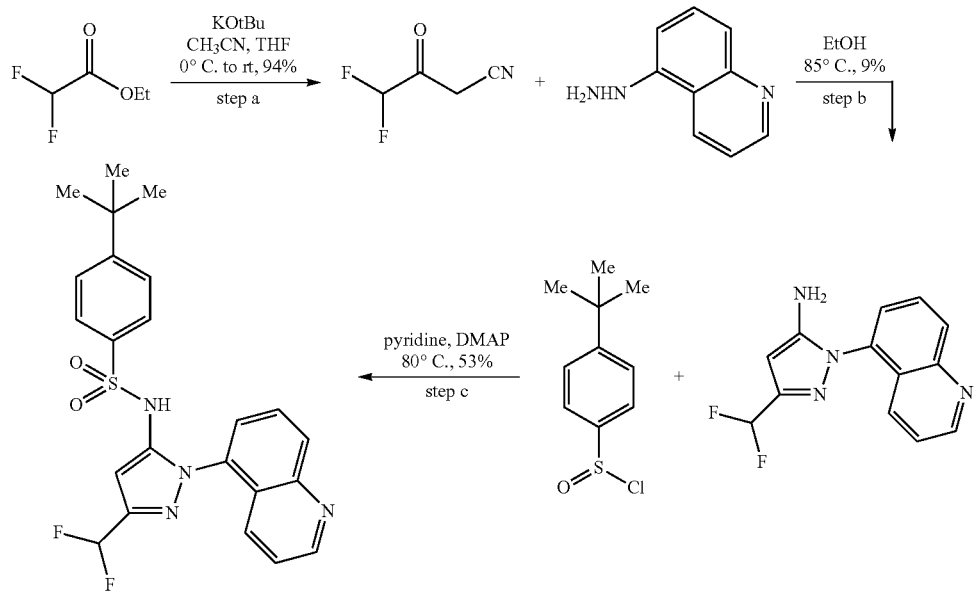

a) To a stirring solution of KOtBu (1.0 M solution in THF, 121 mL, 121 mmol) at 0° C. was added ethyl 2,2-difluoroacetate (10.0 g, 80.6 mmol) and acetonitrile (6.3 mL, 121 mmol). The reaction mixture was warmed to room temperature and stirred for 18 h. Aqueous saturated potassium bisulfate was added to the reaction mixture and the pH was adjusted below 2. The aqueous layer was extracted with ethyl acetate (2×50 mL), and he combined organic layers were dried (Na₂SO₄), filtered, and concentrated in vacuo. The brown crude oil was used directly without further purification (9.0 g, 75 mmol, 94%).

b) To a stirring solution of crude 4,4-difluoro-3-oxobutanenitrile (0.65 g, 4.0 mmol) and 5-hydrazinylquinoline (prepared from Example 4 step a, 0.50 g, 4.2 mmol) in ethanol (8 mL) was heated at 85° C. for 6 h. After cooling to room temperature, ethyl acetate was added to the reaction mixture and washed with aqueous saturated sodium bicarbonate and brine. The organic layer was dried (Na₂SO₄), filtered, and concentrated in vacuo. The crude residue was purified by flash chromatography (SiO₂, 2-10% methanol in ethyl acetate) to give the desired product (0.095 g, 0.36 mmol, 9%).

c) A mixture of 4-t-butylbenzene-1-sulfonyl chloride (0.070 g, 0.30 mmol), 3-(difluoromethyl)-1-(quinolin-5-yl)-1H-pyrazol-5-amine (0.045 g, 0.17 mmol), and DMAP (0.020 g, 0.17 mmol) in pyridine (2 mL) was heated at 80° C. for 5 h with stirring. After cooling to room temperature, the reaction mixture was concentrated in vacuo. The crude residue was purified by flash chromatography (SiO₂, 5% methanol in ethyl acetate), followed by reverse phase HPLC (C18 column, acetonitrile-H₂O with 0.1% TFA as eluent) to give the title compound as a white solid (0.040 g, 0.085 mmol, 53%). ¹H NMR (400 MHz, CD₃OD) δ 8.88 (dd, J=2.0, 4.0 Hz, 1H), 8.15 (d, J=8.0 Hz, 1H), 7.77 (dd, J=7.2, 8.4 Hz, 1H), 7.63 (dddd, J=0.8, 1.6, 1.2, 7.2 Hz, 1H), 7.53-7.43 (m, 5H), 7.31 (dd, J=0.8, 7.2 Hz, 1H), 6.71 (t, J=54.8 Hz, 1H), 6.42 (s, 1H), 1.35 (s, 9H); MS: (ES) m/z calculated for $C_{23}H_{23}F_2N_4O_2S$ [M+H]+ 457.2, found 457.2.

Example 24: Synthesis of 4-t-butyl-N-(2-(isoquinolin-5-yl)-2,4,5,6-tetrahydrocyclopenta[c]pyrazol-3-yl)benzenesulfonamide

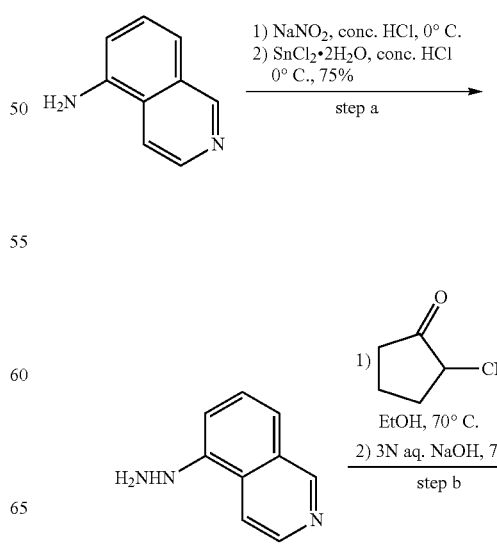

-continued

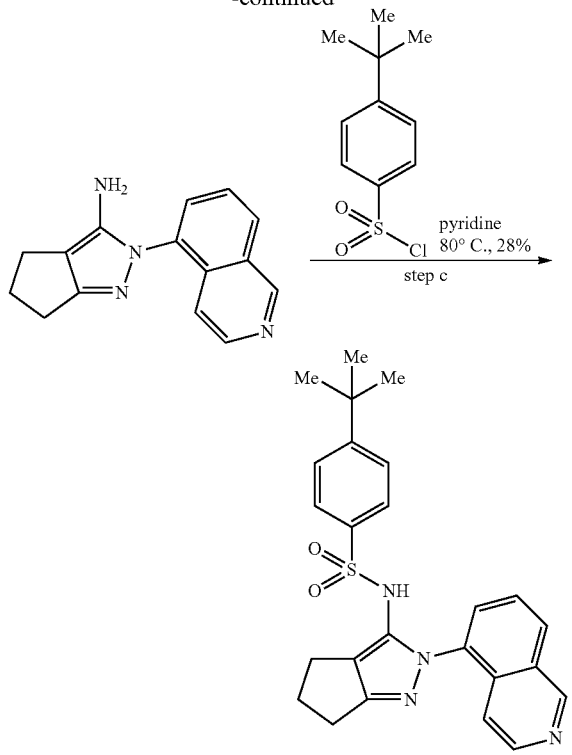

a) To a round bottom flask equipped with a stir bar containing isoquinolin-5-amine (15.4 g, 10.0 mmol) was slowly added concentrated hydrochloric acid (90 mL). The reaction slurry was stirred at 0° C. for 30 min and a solution of NaNO₂ (7.3 g, 105.8 mmol) in minimal amount of deionized water was added dropwise. The reaction mixture was stirred at 0° C. for 30 min and then at room temperature for 30 min to form a deep red solution. The reaction mixture was re-cooled to 0° C., and a solution of SnCl₂.2H₂O (47.4, 210.0 mmol) dissolved in minimal amount of concentrated hydrochloric acid was added then dropwise. The thick, brown mixture was stirred at 0° C. for 30 min and then at room temperature for 4 h. The solid was collected by filtration and washed with cold ethanol (200 mL). The yellow solid was suspended in 2:1 CHCl₃/iPrOH (300 mL) and the solution was adjusted to pH ~12-14 with 2 M aqueous sodium hydroxide (300 mL). The phases were separated and the aqueous layer was further extracted with CHCl₃/iPrOH (2×300 mL). The combined organic layers were dried with anhydrous magnesium sulfate (MgSO₄), filtered, and concentrated in vacuo. The resulting crude product was used directly without further purification (12.7 g, 79.8 mmol, 75%).

b) To a stirring suspension of crude 5-hydrazinylisoquinoline (0.45 g, 2.2 mmol) and 2-oxocyclopentanecarbonitrile (prepared as in Fleming, et al. *J. Org. Chem.*, 2007, 72, 1431-1436, 0.24 g, 2.2 mmol) in ethanol (10 mL) was heated at 70° C. for 2 h. After cooling to room temperature, 3 M aqueous sodium hydroxide (0.5 mL) was added to the reaction mixture and stirred at room temperature for 1 h. The mixture was then concentrated in vacuo and the resulting residue was extracted with ethyl acetate. The organic layer was dried (Na₂SO₄), filtered, and concentrated in vacuo. The crude residue was purified by flash chromatography (SiO₂, 5-10% ethyl acetate in hexanes) to give the desired product (0.48 g, 1.6 mmol, 73%).

c) A mixture of 4-t-butylbenzenesulfonyl chloride (0.075 g, 0.32 mmol) and 2-(isoquinolin-5-yl)-2,4,5,6-tetrahydrocyclopentapyrazol-3-amine (0.050 g, 0.20 mmol) in pyridine (1 mL) was stirred at room temperature for 1 h. The reaction mixture was added 1 N aqueous hydrochloric acid and extracted with in 2:1 CH₂Cl₂/iPrOH (2×10 mL). The combine organic layers were dried (Na₂SO₄), filtered, and concentrated in vacuo. The resulting material was purified by reverse phase HPLC (C18 column, acetonitrile-H₂O with 0.1% TFA as eluent) to give the title compound as a white solid (0.025 g, 0.056 mmol, 28%). ¹H NMR (400 MHz, DMSO-d₆) δ 10.10 (s, 1H), 9.35 (s, 1H), 8.42 (d, J=6.0 Hz, 1H), 8.17 (d, J=8.8 Hz, 1H), 7.68 (t, J=8.0 Hz, 1H), 7.49 (d, J=7.2 Hz, 1H), 7.41-7.37 (m, 3H), 7.18 (d, J=4.8 Hz, 1H), 2.64 (t, J=7.2 Hz, 2H), 2.21 (pent, J=7.2 Hz, 2H), 2.06 (t, J=7.5 Hz, 2H), 1.25 (s, 9H); MS: (ES) m/z calculated for C₂₅H₂₇N₄O₂S [M+H]⁺ 447.2, found 447.1.

Example 25: Synthesis of N-(1-(1-aminoisoquinolin-5-yl)-3-methyl-1H-pyrazol-5-yl)-4-t-butylbenzenesulfonamide

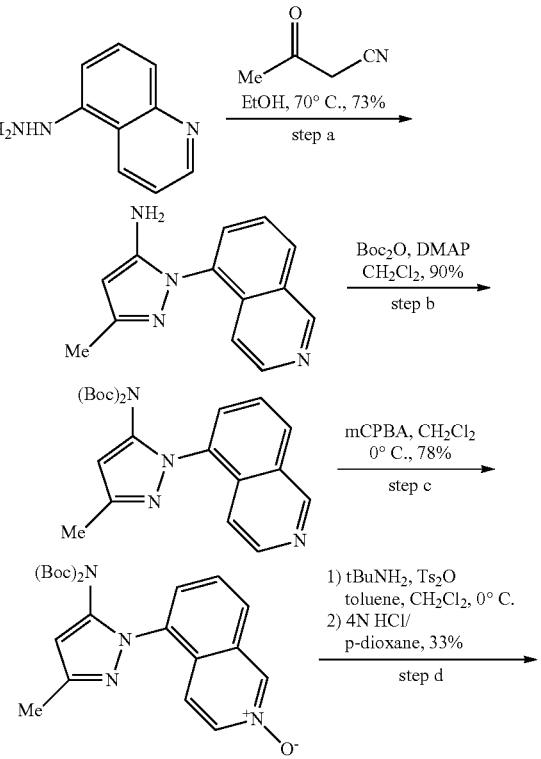

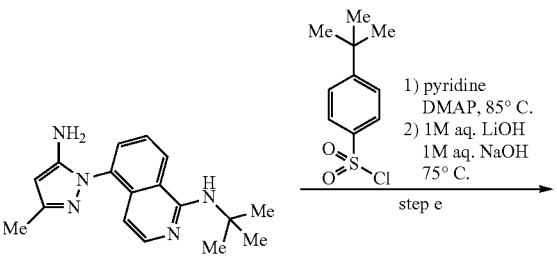

-continued

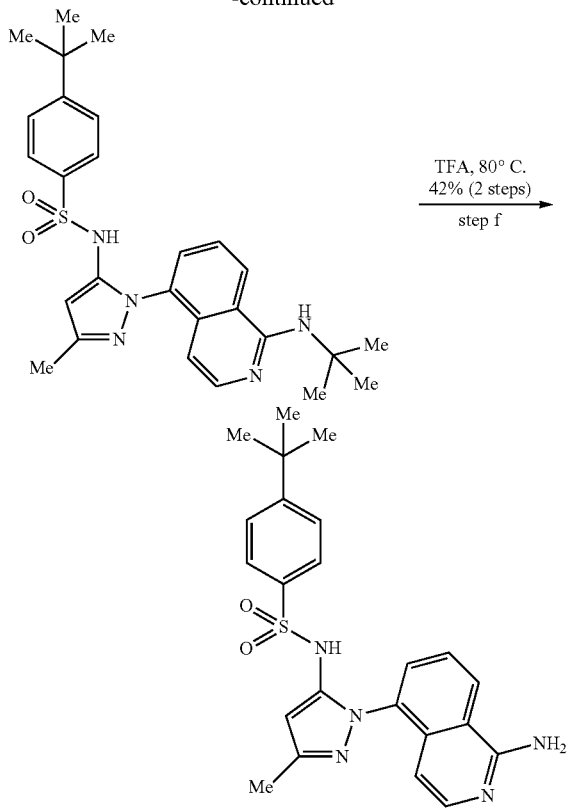

a) To a stirring suspension of 5-hydrazinylisoquinoline (prepared from Example 25 step a, 0.60 g, 3.8 mmol) and 3-oxobutanenitrile (0.31 g, 3.8 mmol) in ethanol (3 mL) was heated at 80° C. for 2 h. After cooling to room temperature, the reaction mixture was in vacuo and the resulting crude residue was purified by flash chromatography (SiO$_2$, 0-20% methanol in ethyl acetate) to give the desired product (0.067 g, 2.8 mmol, 73%).

b) To a solution of 1-(isoquinolin-5-yl)-3-methyl-1H-pyrazol-5-amine (0.45 g, 2.0 mmol) in dichloromethane (10 mL) was added DMAP (0.30 g, 2.5 mmol) and di-t-butyl dicarbonate (Boc$_2$O, 1.2 g, 5.5 mmol). The reaction mixture was stirred at room temperature for 15 h and ethyl acetate was added. The resulting solution was washed with 2 N aqueous sodium hydroxide, 2 N aqueous hydrochloric acid, and brine. The organic layer was dried (Na$_2$SO$_4$), filtered, and concentrated in vacuo. The crude product was purified by flash chromatography (SiO$_2$, 20-50% ethyl acetate in hexanes) to afford the desired product (0.76 g, 1.8 mmol, 90%).

c) To a stirring solution of di-t-butyl 1-(isoquinolin-5-yl)-3-methyl-1H-pyrazol-5-yliminodicarbonate (0.15 g, 0.35 mmol) in dichloromethane (10 mL) at 0° C. was added 3-chloroperbenzoic acid (mCPBA, 0.2 g, 0.90 mmol). The reaction mixture was slowly warmed to room temperature and stirred at the same temperature for 4 h. A solution of 15% iPrOH in dichloromethane was added to the reaction mixture and washed with aqueous saturated sodium bicarbonate. The organic layer was dried (Na$_2$SO$_4$), filtered, and concentrated in vacuo. The crude product was purified by flash chromatography (SiO$_2$, 5-10% methanol in dichloromethane) to afford the desired product (0.12 g, 0.27 mmol, 78%).

d) A stirring mixture of 5-(5-(bis(t-butoxycarbonyl)amino)-3-methyl-1H-pyrazol-1-yl)isoquinoline 2-oxide (0.12 g, 0.27 mmol) in toluene (3 mL) and dichloromethane (3 mL) at 0° C. was added t-butylamine (0.3 mL, 2.86 mmol) and p-toluenesulfonic anhydride (Ts$_2$O, 0.30 g, 0.93 mmol) in three portions. The reaction mixture was slowly warmed to room temperature over 2 h and ethyl acetate was added. The organic layer was washed with aqueous saturated sodium bicarbonate, 1 N aqueous hydrochloric acid, and brine. The organic layer was dried (Na$_2$SO$_4$), filtered, and concentrated in vacuo. The resulting crude product was then dissolved in dichloromethane (5 mL) and a solution of hydrochloric acid in p-dioxane (4.0 N solution in p-dioxane, 5.0 mL, 20 mmol) was added. The reaction mixture was stirred at room temperature for 2 h and ethyl acetate was added. The organic layer was washed with aqueous saturated sodium bicarbonate, dried (Na$_2$SO$_4$), filtered, and concentrated in vacuo. The crude product was used directly without further purification (0.026 g, 0.090 mmol, 33%)

e) A mixture of crude 5-(5-amino-3-methyl-1H-pyrazol-1-yl)-N-t-butylisoquinolin-1-amine (0.055 g, 0.30 mmol), 4-acetylbenzene-1-sulfonyl chloride (0.090 g, 0.39 mmol), and DMAP (0.037 g, 0.30 mmol) in pyridine (2 mL) was heated at 85° C. for 1 h with stirring. After cooling to room temperature, 1 M aqueous lithium hydroxide (1 mL) and 1 M aqueous sodium hydroxide (1 mL) were added to the reaction mixture. The resulting mixture was heated at 75° C. for 30 min. After cooling to room temperature, the reaction mixture was neutralized with 1 N aqueous hydrochloric acid. The aqueous layer was extracted with ethyl acetate and the organic layer was washed with aqueous saturated sodium bicarbonate, dried (Na$_2$SO$_4$), filtered, and concentrated in vacuo. The crude material was used directly to the next step.

f) The crude residue was dissolved in TFA (8 mL) and heated at 80° C. for 1.5 h with stirring. The reaction mixture was cooled to room temperature and concentrated in vacuo. The crude product was then dissolved in 15% methanol in dichloromethane and washed with aqueous saturated sodium bicarbonate. The organic layer was dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.035 g, 0.080 mmol, 42% for 2 steps). $^1$H NMR (400 MHz, CD$_3$OD) δ 8.23 (dd, J=0.8, 8.8 Hz, 1H), 7.60-7.54 (m, 3H), 7.50-7.42 (m, 4H), 6.31 (dd, J=0.8, 6.4 Hz, 1H), 5.93 (s, 1H), 2.22 (s, 3H), 1.36 (s, 9H); MS: (ES) m/z calculated for C$_{23}$H$_{26}$N$_5$O$_2$S [M+H]$^+$436.2, found 436.1.

Example 26: Synthesis of 4-t-butyl-3-fluoro-N-(3-methyl-1-(quinolin-5-yl)-1H-pyrazol-5-yl)benzenesulfonamide

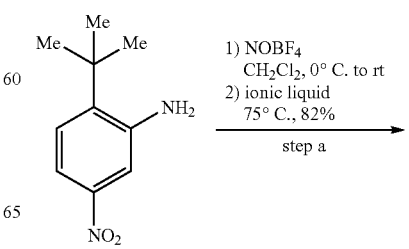

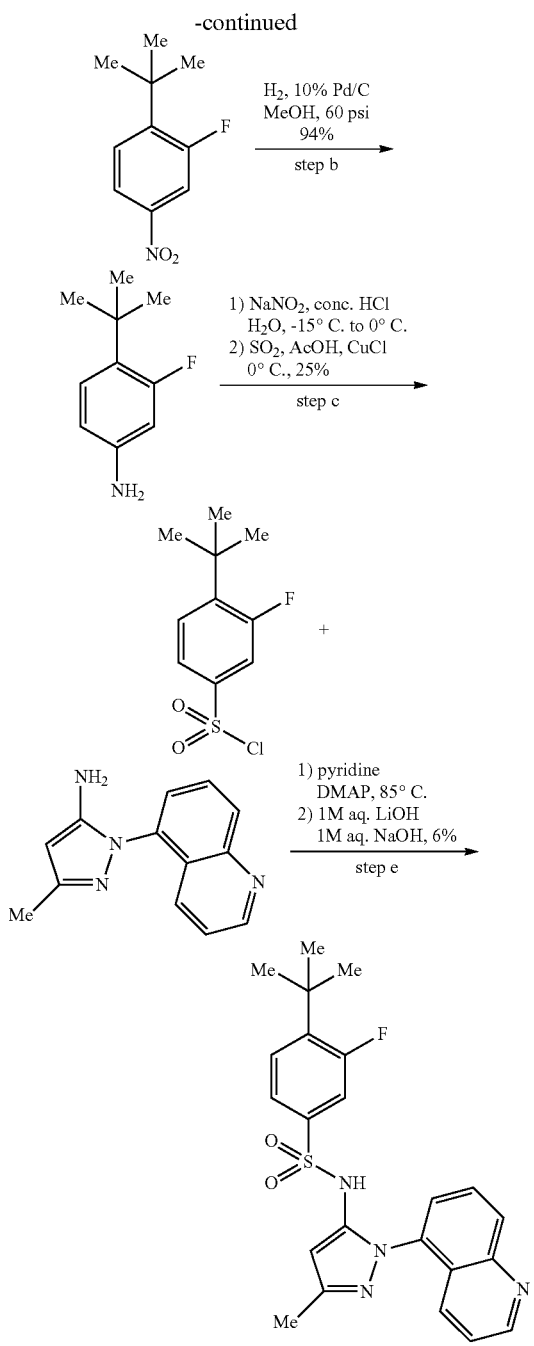

a) To a stirred suspension of nitrosyl tetrafluoroborate (8.4 g, 71.9 mmol) in dichloromethane at 0° C. was added quinolin-5-yl-hydrazine (prepared as in Laali, et al. *J. Fluorine Chem.*, 2001, 107, 31-34, 12.0 g, 61.8 mmol) in small portions over 5 min. After the addition is complete, the reaction mixture was stirred at 0° C. for 1 h and slowly warmed to room temperature over 1 h to form a fine suspension. To this suspension, 1-ethyl-3-methyl-imidazolium tetrafluoroborate (ionic liquid, 50 g, 252.6 mmol) was slowly added, and the resulting mixture was heated at 75° C. for 2 h. The organic volatile was removed by distillation via a Dean-Stark condenser. After cooling the mixture to room temperature, diisopropyl ethylamine (iPr$_2$NEt, 10 mL) was added to the reaction mixture and stirred for 10 min. Diethyl ether (300 mL) was added to the reaction mixture and washed with 1 N aqueous hydrochloric acid, and brine, dried (Na$_2$SO$_4$), filtered, and concentrated in vacuo. The crude product was used directly without further purification (10.0 g, 50.8 mmol, 82%).

b) In a Parr shaker flask containing crude 1-t-butyl-2-fluoro-4-nitrobenzene (1.0 g, 5.1 mmol) and Pd/C (10% by weight, 0.040 g) in methanol (60 mL) was hydrogenated at 60 psi for 2 h. The reaction mixture was diluted with methanol and filtered through a pad of Celite. The filtrate was concentrated in vacuo and the resulting residue was used directly without further purification (0.80 g, 4.8 mmol, 94%).

c) To a flask containing glacial acetic acid (2 mL) at 0° C. was bubbled in sulfur dioxide gas (SO$_2$) for 30 min. Copper (I) chloride (CuCl, 0.10 g, 1.0 mmol) was added to the reaction mixture and stirred 30 min at 0° C. to give a blue-green solution. To a separate flask, a solution of crude 4-t-butyl-3-fluro aniline (0.20 g, 1.2 mmol) in concentrated hydrochloric acid (3 mL) at −15° C. was added a solution of NaNO$_2$ (0.12 g, 1.7 mmol) in deionized water (1 mL). The reaction mixture was stirred at the same temperature for 30 min. This diazonium solution was slowly added to the prepared copper solution and the resulting solution was bubbled with SO$_2$ for another 5 min. The reaction mixture was stirred at −15° C. for 1 h and warmed to 0° C. over 1 h. Diethyl ether was then added to the reaction mixture and the content was poured over ice. The resulting mixture was extracted with diethyl ether and the organic layer was further washed with ice water, dried (Na$_2$SO$_4$), filtered, and concentrated in vacuo. The dark crude oil was purified by flash chromatography (SiO$_2$, 1-3% ethyl acetate in hexanes) to afford the desired product (0.075 g, 0.30 mmol, 25%).

d) A mixture of 4-t-butyl-3-fluorobenzene-1-sulfonyl chloride (0.075 g, 0.30 mmol), 3-methyl-1-(quinolin-5-yl)-1H-pyrazol-5-amine (prepared from Example 4 step b, 0.050 g, 0.22 mmol), and DMAP (0.027 g, 0.22 mmol) in pyridine (1 mL) was heated at 85° C. for 2.5 h with stirring. After cooling to room temperature, 1 M aqueous lithium hydroxide (1 mL) and 1 M aqueous sodium hydroxide (1 mL) were added to the reaction mixture. The resulting mixture was stirred at room temperature for 15 h and neutralized with 1 N aqueous hydrochloric acid. The aqueous layer was extracted with ethyl acetate and the organic layer was washed with aqueous saturated sodium bicarbonate, dried (Na$_2$SO$_4$), filtered, and concentrated in vacuo. The resulting crude residue was purified by reverse phase HPLC (C18 column, acetonitrile-H$_2$O with 0.1% TFA as eluent) to give the title compound as a white solid (0.006 g, 0.014 mmol, 6%). $^1$H NMR (400 MHz, CD$_3$OD) δ 8.83 (dd, J=1.6, 4.4 Hz, 1H), 8.08 (dd, J=1.2, 8.4 Hz, 1H), 7.79 (dd, J=7.2, 8.4 Hz, 1H), 7.69 (ddd, J=0.8, 1.6, 7.6 Hz, 1H), 7.44 (dd, J=1.2, 7.2 Hz, 1H), 7.40-7.31 (m, 3H), 7.20 (dd, J=1.6, 7.2 Hz, 1H), 5.88 (s, 1H), 2.21 (s, 3H), 1.39 (s, 9H); MS: (ES) m/z calculated for C$_{23}$H$_{24}$FN$_4$O$_2$S [M+H]$^+$ 439.2, found 439.2.

Example 27: Synthesis N-(1-(2-aminoquinolin-5-yl)-3-methyl-1H-pyrazol-5-yl)-4-t-butyl-3-fluorobenzenesulfonamide

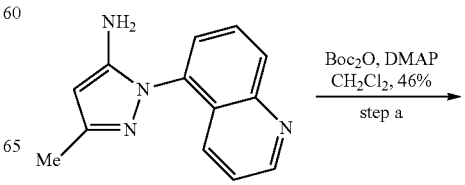

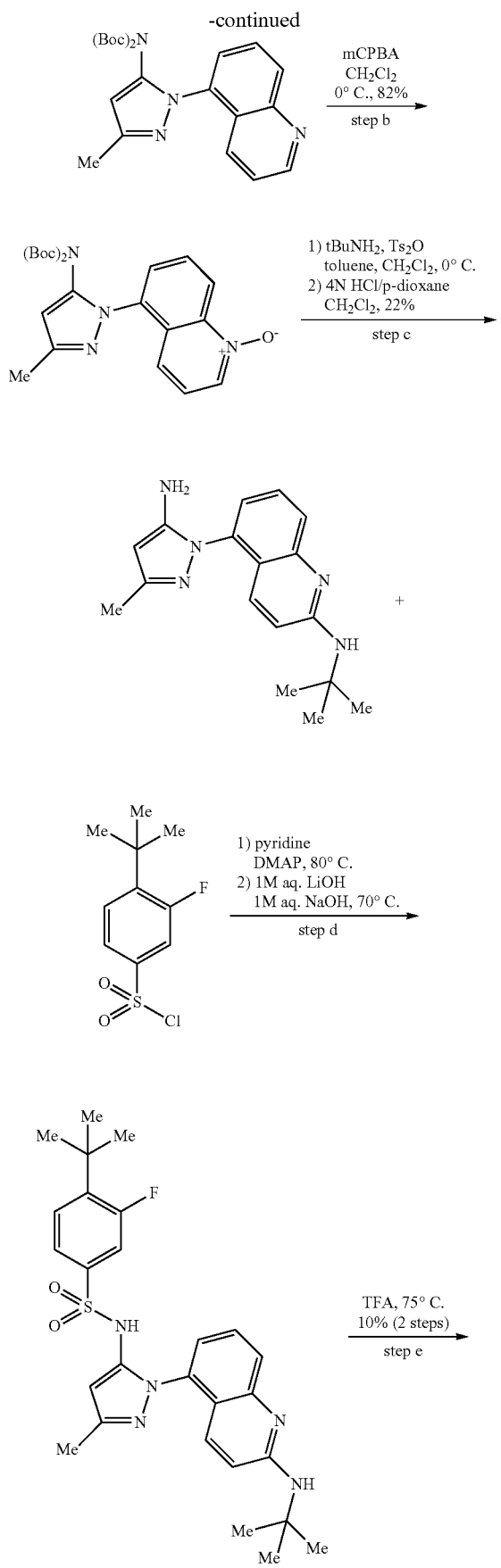

a) To a solution of 3-methyl-1-(quinolin-5-yl)-1H-pyrazol-5-amine (prepared from Example 4 step b, 4.0 g, 17.9 mmol) in dichloromethane (50 mL) was added DMAP (2.2 g, 17.9 mmol) and Boc$_2$O (7.8 g, 35.9 mmol). The reaction mixture was stirred at room temperature for 3 h and ethyl acetate was added. The organic layer was washed with 1 N aqueous hydrochloric acid, aqueous saturated sodium bicarbonate, and brine. The organic layer was dried (Na$_2$SO$_4$), filtered, and concentrated in vacuo and the crude product was used directly without further purification (3.5 g, 8.3 mmol, 46%).

b) To a stirring solution of crude di-t-butyl 3-methyl-1-(quinolin-5-yl)-1H-pyrazol-5-yliminodicarbonate (3.5 g, 8.3 mmol) in dichloromethane (50 mL) at 0° C. was slowly added mCPBA (4.0 g, 17.8 mmol). The reaction mixture was slowly warmed to room temperature and stirred for 2 h. A solution of 15% iPrOH in dichloromethane was added to the reaction mixture and washed with aqueous saturated sodium bicarbonate. The organic layer was dried (Na$_2$SO$_4$), filtered, and concentrated in vacuo. The crude product was purified by flash chromatography (SiO$_2$, 2-5% methanol in dichloromethane) to afford the desired product (3.0 g, 6.8 mmol, 82%).

c) A stirring mixture of 5-(5-(bis(t-butoxycarbonyl)amino)-3-methyl-1H-pyrazol-1-yl)quinoline 1-oxide (3.0 g, 6.8 mmol) in toluene (40 mL) and dichloromethane (40 mL) at 0° C. was added t-butylamine (5.5 mL, 52.3 mmol) and Ts$_2$O (5.0 g, 15.3 mmol) in two portions. The reaction mixture was slowly warmed to room temperature over 2 h and ethyl acetate was added. The organic layer was washed with aqueous saturated sodium bicarbonate, 1 N aqueous hydrochloric acid, and brine. The organic layer was dried (Na$_2$SO$_4$), filtered, and concentrated in vacuo. The crude product was then dissolved in dichloromethane (10 mL) and a solution of hydrochloric acid in p-dioxane (4.0 N solution in p-dioxane, 20 mL, 80 mmol) was added. The reaction mixture was stirred at room temperature for 2 h and ethyl acetate was added. The organic layer was washed with aqueous saturated sodium bicarbonate, dried (Na$_2$SO$_4$), filtered, and concentrated in vacuo. The crude product was used directly without further purification (0.45 g, 1.52 mmol, 22%)

d) A mixture of crude 5-(5-amino-3-methyl-1H-pyrazol-1-yl)-N-t-butylquinolin-2-amine (0.075 g, 0.25 mmol), 4-t-butyl-3-fluorobenzene-1-sulfonyl chloride (prepared from Example 27 step c, 0.11 g, 0.44 mmol), and DMAP (0.031 g, 0.25 mmol) in pyridine (2 mL) was heated at 80° C. for 2 h with stirring. After cooling to room temperature, 1 M aqueous lithium hydroxide (1 mL) and 1 M aqueous sodium hydroxide (1 mL) were added to the reaction mixture and heated at 70° C. for 30 min. After cooling to room temperature, the reaction mixture was neutralized with 1 N aqueous hydrochloric acid. The aqueous layer was extracted with ethyl acetate and the organic layer was washed with aqueous saturated sodium bicarbonate, dried ($Na_2SO_4$), filtered, and concentrated in vacuo. The crude material was used directly to the next step.

e) The crude residue was dissolved in TFA (6 mL) and heated at 75° C. for 2 h with stirring. After cooling to room temperature, the reaction mixture was concentrated in vacuo. The crude product was then dissolved in 10% methanol in dichloromethane and washed with aqueous saturated sodium bicarbonate. The organic layer was dried ($Na_2SO_4$), filtered, and concentrated in vacuo. The resulting crude product was purified by reverse phase HPLC (C18 column, acetonitrile-$H_2O$ with 0.1% TFA as eluent) to give the title compound as a white solid (0.011 g, 0.024 mmol, 10% for 2 steps). $^1$H NMR (400 MHz, DMSO-$d_6$) 11.01 (br s, 1H), 7.47 (m, 2H), 7.31 (d, J=8.0 Hz, 1H), 7.27 (d, J=8.0 Hz, 1H), 7.25 (dd, J=2.0, 8.0 Hz, 1H), 7.16 (dd, J=2.0, 8.0 Hz, 1H), 6.91 (m, 3H), 5.86 (s, 1H), 2.14 (s, 3H), 1.32 (s, 9H); MS: (ES) m/z calculated for $C_{23}H_{25}FN_5O_2S$ $[M+H]^+$ 454.2, found 454.1.

Example 28: Synthesis of 4-t-butyl-3-chloro-N-(3-methyl-1-(quinolin-5-yl)-1H-pyrazol-5-yl)benzenesulfonamide

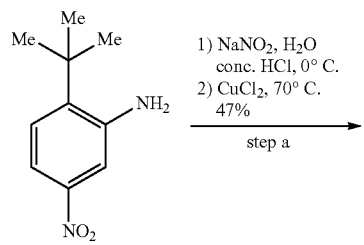

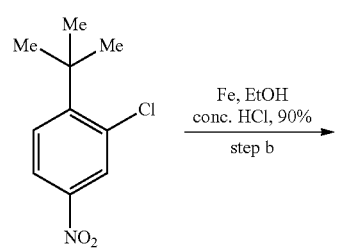

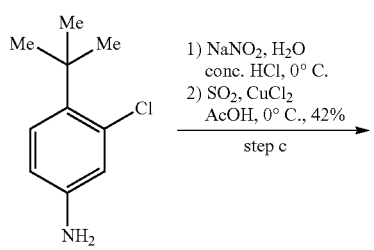

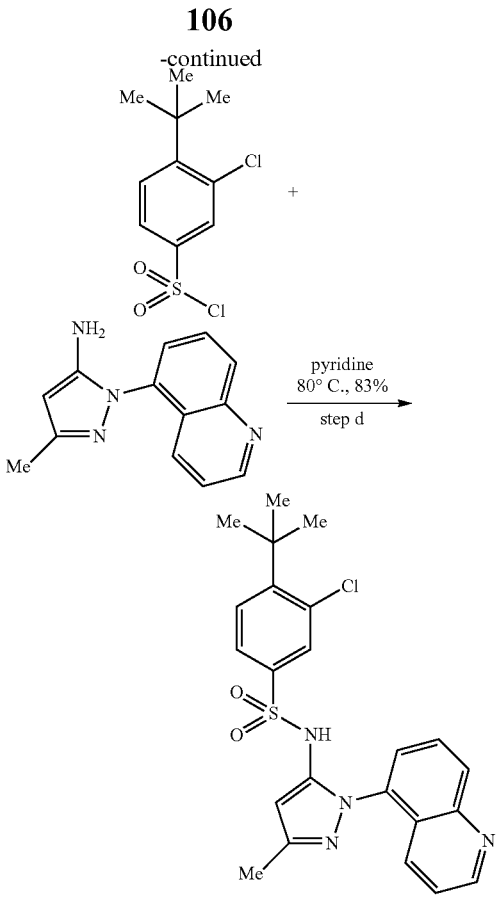

a) To a stirring solution of quinolin-5-yl-hydrazine (prepared as in Laali, et al. *J. Fluorine Chem.*, 2001, 107, 31-34, 0.25 g, 1.29 mmol) in concentrated hydrochloric acid (1.3 mL) at 0° C. was added a solution of $NaNO_2$ (0.13 g, 1.9 mmol) in deionized water (0.64 mL). The reaction mixture was stirred for 30 min at 0° C. and heated at 70° C. for 30 min. Copper(II) chloride (0.22 g, 1.6 mmol) was added to the hot mixture and stirred at 70° C. for 30 min. After cooling the reaction mixture to room temperature, a precipitate was formed and the solid was collected by filtration. The solid was rinsed with cold deionized water and dried under vacuum to give the desired product (0.13 g, 0.61 mmol, 47%).

b) Concentrated hydrochloric acid (0.25 mL) was added slowly to a solution of 1-t-butyl-2-chloro-4-nitrobenzene (0.13 g, 0.61 mmol) and iron powder (0.17 g, 3.0 mmol) in ethanol (1.2 mL). The reaction mixture was stirred at room temperature for 1 h and the slurry was diluted with ethanol. The resulting mixture was then filtered through a pad of Celite and rinsed with additional ethanol (30 mL). The filtrate was concentrated in vacuo and the resulting crude material was purified by flash chromatography ($SiO_2$, 0-80% ethyl acetate in hexanes) to afford the desired product (0.10 g, 0.55 mmol, 90%).

c) To a solution of glacial acetic acid (2 mL) at 0° C. was bubbled in sulfur dioxide gas ($SO_2$) for 30 min. Copper(II) chloride (0.073 g, 0.54 mmol) was added to the reaction mixture and stirred for an additional 30 min at 0° C. To another flask containing of 4-t-butyl-3-chloroaniline (0.10 g, 0.54 mmol) in concentrated hydrochloric acid (0.5 mL) was added a solution of $NaNO_2$ (0.06 g, 0.87 mmol) in deionized water (0.1 mL) at 0° C. with stirring. This diazonium solution was slowly added to the prepared copper solution and stirred at 0° C. for 30 min. Diethyl ether was added to the reaction mixture and the phases were separated. The aqueous layer was further extracted with ethyl acetate (2×10 mL), and the combined organic layers were dried (Na$_2$SO$_4$), filtered, and concentrated in vacuo. The crude residue was purified by flash chromatography (SiO$_2$, 0-20% ethyl acetate in hexanes) to afford the desired product (0.061 g, 0.23 mmol, 42%).

d) A mixture of 4-t-butyl-3-chlorobenzene-1-sulfonyl chloride (0.050 g, 0.19 mmol) and 3-methyl-1-(quinolin-5-yl)-1H-pyrazol-5-amine (prepared from Example 4 step b, 0.042 g, 0.095 mmol) in pyridine (0.2 mL) was heated at 80° C. for 1 h with stirring. After cooling to room temperature, the reaction mixture was concentrated in vacuo and the crude residue was purified by flash chromatography (SiO$_2$, 20% ethyl acetate in hexanes) to give the title compound as a white solid (0.066 g, 0.16 mmol, 83%). $^1$H NMR (400 MHz, DMSO-d$_6$) δ 8.86 (dd, J=2.0, 4.0 Hz, 1H), 7.98 (d, J=8.4 Hz, 1H), 7.76 (t, J=8.4 Hz, 1H), 7.70 (d, J=8.4 Hz, 1H), 7.44 (s, 3H), 7.40 (d, J=7.6 Hz, 1H), 7.34 (dd, J=4.0, 8.0 Hz, 1H), 5.48 (s, 1H), 2.02 (s, 3H), 1.44 (s, 9H); MS: (ES) m/z calculated for C$_{23}$H$_{24}$ClN$_4$O$_2$S [M+H]$^+$ 455.2, found 455.2.

Example 29: Synthesis of 3-fluoro-4-isopropoxy-N-(3-methyl-1-(quinolin-5-yl)-1H-pyrazol-5-yl)benzenesulfonamide

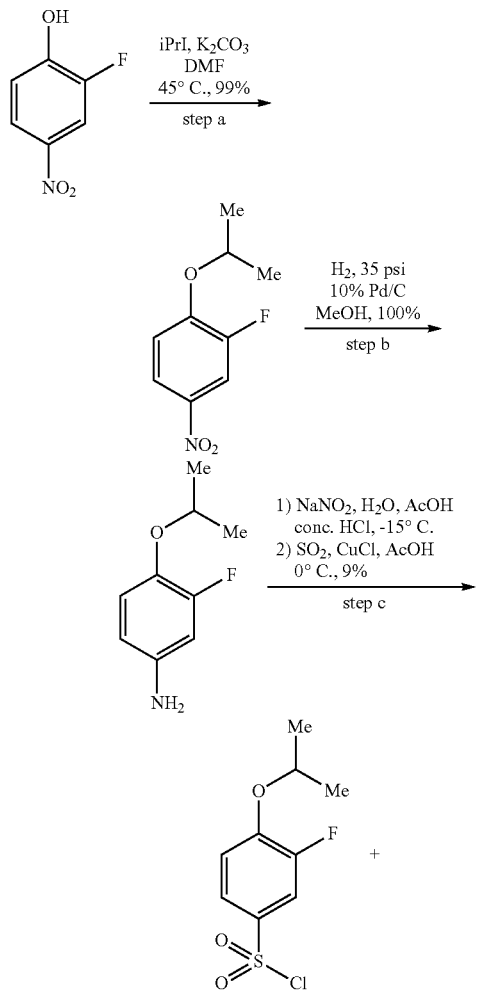

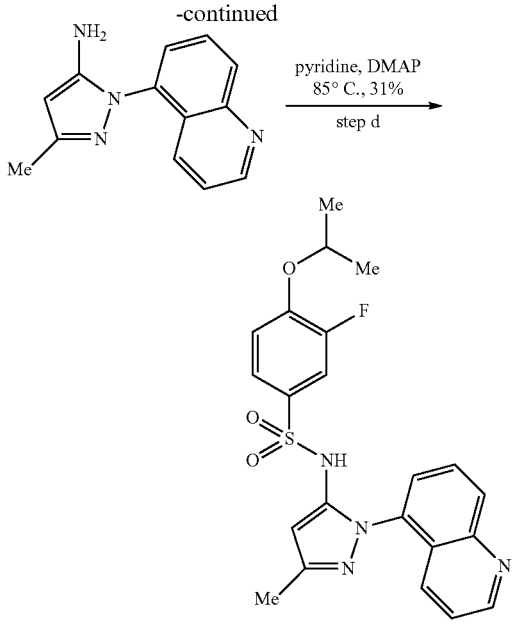

a) To a stirring solution of 2-fluoro-4-nitrophenol (1.6 g, 10.2 mmol) and potassium carbonate (K$_2$CO$_3$, 2.5 g, 18.1 mmol) in DMF (10 mL) was stirred at room temperature for 5 min. Isopropyl iodide (iPrI, 2 mL, 20.0 mmol) was then added to the reaction and the resulting mixture was stirred at room temperature for 2 h, and then heated at 45° C. for 6 h. The reaction mixture was cooled to room temperature and diethyl ether was added. The mixture was washed with deionized water and aqueous saturated sodium bicarbonate. The organic layer was dried (Na$_2$SO$_4$), filtered, and concentrated in vacuo. The crude product was used directly without further purification (2.0 g, 10.1 mmol, 99%).

b) To a Parr shaker flask containing crude 2-fluoro-1-isopropoxy-4-nitrobenzene (2.0 g, 10.1 mmol) and Pd/C (10% by weight, 0.50 g) in methanol (100 mL) was hydrogenated at 35 psi for 1 h. The reaction mixture was diluted with methanol and filtered through a pad of Celite. The filtrate was concentrated in vacuo and the resulting residue was used directly without further purification (1.7 g, 10.1 mmol, 100%).

c) To a solution of glacial acetic acid (40 mL) was bubbled in SO$_2$. After 15 min, copper (I) chloride (0.50 g, 5.1 mmol) was added and the bubbling of SO$_2$ gas continued until the solution maintained a green/blue color. To another flask containing of crude 3-fluoro-4-isopropoxyaniline (1.5 g, 8.9 mmol) in 1:1 glacial acetic acid and concentrated hydrochloric acid (10 mL) at −15° C. was added a solution of NaNO$_2$ (0.75 g, 10.8 mmol) in deionized water (3 mL) and stirred at −15° C. for 30 min. This diazonium solution was then slowly added to the prepared copper solution and stirred at −15° C. for 30 min. Diethyl ether (30 mL) was added to the reaction mixture and stirred at −15° C. for 1 h. The reaction mixture was poured into ice and additional diethyl ether (30 mL) was added. The phases were separated and the aqueous layer was further extracted with ethyl acetate (2×10 mL). The combined organic layers were dried (Na$_2$SO$_4$), filtered, and concentrated in vacuo. The crude residue was purified by flash chromatography (SiO$_2$, 5-10% ethyl acetate in hexanes) to afford the desired product (0.20 g, 0.79 mmol, 9%).

d) A mixture of 3-fluoro-4-isopropoxybenzene-1-sulfonyl chloride (0.050 g, 0.19 mmol), 3-methyl-1-(quinolin-5-yl)-1H-pyrazol-5-amine (prepared from Example 4 step b, 0.025 g, 0.11 mmol), and DMAP (0.020 g, 0.16 mmol) in pyridine (2 mL) was heated at 85° C. for 2 h with stirring. After cooling to room temperature, the reaction mixture was concentrated in vacuo and the crude residue was purified by reverse phase HPLC (C18 column, acetonitrile-H$_2$O with 0.1% TFA as eluent) to give the title compound as a white solid (0.015 g, 0.034 mmol, 31%). $^1$H NMR (400 MHz, CD$_3$OD) δ 8.85 (d, J=4.4 Hz, 1H), 8.11 (d, J=8.4 Hz, 1H), 7.80 (t, J=8.0 Hz, 1H), 7.62 (d, J=8.8 Hz, 1H), 7.45-7.40 (m, 2H), 7.25 (d, J=8.8 Hz, 1H), 7.12 (dd, J=2.4, 10.4 Hz, 1H), 6.92 (t, J=8.4 Hz, 1H), 6.10 (s, 1H), 4.63 (hept, J=6.4 Hz, 1H), 2.27 (s, 3H), 1.37 (d, J=6.4 Hz, 6H); MS: (ES) m/z calculated for 022H$_{22}$FN$_4$O$_3$S [M+H]$^+$ 441.2, found 441.2.

Example 30: Synthesis of N-(1-(8-aminoquinolin-5-yl)-3-methyl-1H-pyrazol-5-yl)-4-t-butyl-3-fluorobenzenesulfonamide

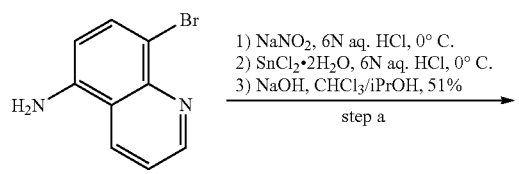

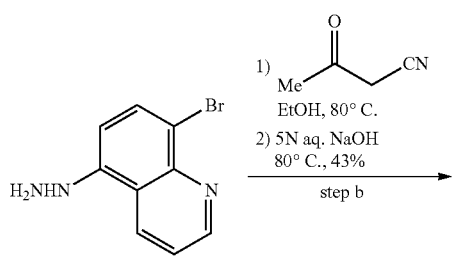

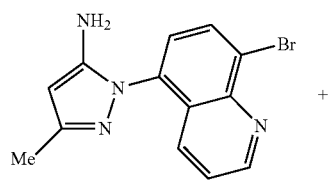

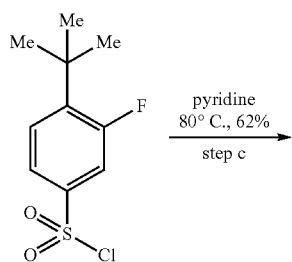

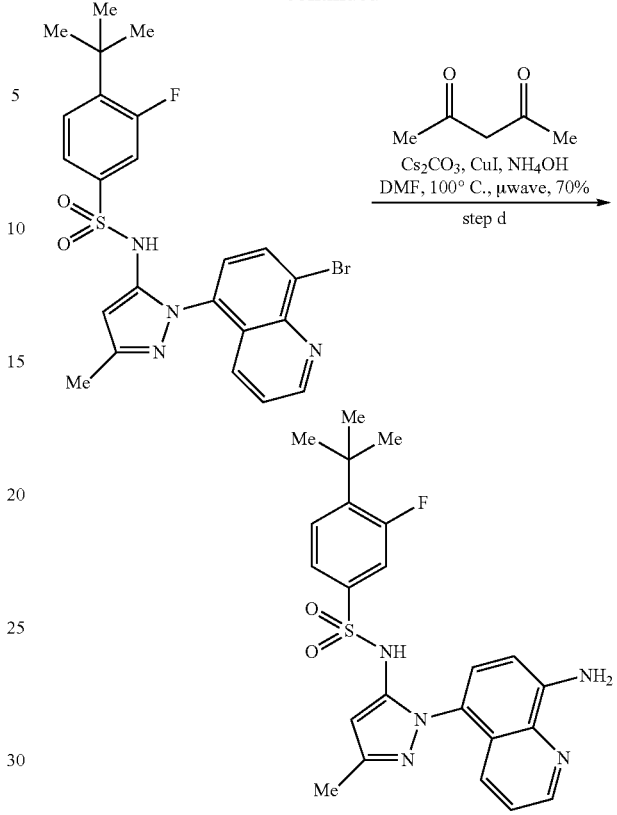

a) To a stirring solution of 5-amino-8-bromoquinoline (1.1 g, 5.0 mmol) in 6 N aqueous hydrochloric acid (10 mL) at 0° C. was slowly added solid NaNO$_2$ (1.0 g, 14.5 mmol), while maintaining the internal temperature below 0° C. The reaction mixture was stirred at 0° C. for 1 h and a solution of SnCl$_2$.2H$_2$O (3.2 g, 12.5 mmol) dissolved in 6 N aqueous hydrochloric acid (3 mL) was added then dropwise. The mixture was stirred at room temperature for 2 h and the solution was neutralized to pH ~7 with 1 M aqueous sodium hydroxide. The mixture was extracted with 2:1 CHCl$_3$/iPrOH and the organic layer was dried (Na$_2$SO$_4$), filtered, and concentrated in vacuo. The resulting crude product was purified by flash chromatography (SiO$_2$, 50% ethyl acetate in hexanes) to give the desired compound as a yellow solid (0.60 g, 2.6 mmol, 51%).

b) To a stirring suspension of 8-bromo-5-hydrazinylquinoline (2.0 g, 8.4 mmol) and 3-oxo-butyronitrile (0.70 g, 8.4 mmol) in ethanol (20 mL) was heated at 80° C. for 3 h. After cooling to room temperature, 5 M aqueous sodium hydroxide (1 mL) was added to the reaction mixture and heated at 80° C. for 1 h. The resulting mixture was cooled to room temperature and concentrated in vacuo. The crude residue was dissolved in 1:1 dichloromethane/methanol (40 mL) and the phases were separated. The organic layer was dried (Na$_2$SO$_4$), filtered, and concentrated in vacuo. The resulting crude was purified by flash chromatography (SiO$_2$, 50-100% ethyl acetate in hexanes) to give a brown product as the desired product (1.1 g, 3.6 mmol, 43%).

c) A stirring mixture of 4-t-butyl-3-fluorobenzene-1-sulfonyl chloride (prepared from Example 27 step c, 1.1 g, 4.2 mmol) and 1-(8-bromoquinolin-5-yl)-3-methyl-1H-pyrazol-5-amine (0.97 g, 3.2 mmol) in pyridine (5 mL) was heated at 80° C. for 15 h. After cooling to room temperature, the reaction mixture was concentrated in vacuo. The crude solid was recrystallized from hot ethanol (5 mL) and the resulting solid was collected by filtration to give the desired compound (0.10 g, 0.19 mmol, 62%).

d) To a stirring solution of N-(1-(8-bromoquinolin-5-yl)-3-methyl-1H-pyrazol-5-yl)-4-t-butyl-3-fluorobenzenesulfonamide (0.052 g, 0.10 mmol) in ammonium hydroxide (1 mL) and DMF (1 mL) was added 2,4-pentanedione (0.006 g, 0.06 mmol), cesium carbonate ($Cs_2CO_3$, 0.064 g, 0.20 mmol), and copper(I) iodide (CuI, 0.0095 g, 0.050 mmol). The reaction mixture was heated at 120° C. in microwave for 2 h. After cooling to room temperature, ethyl acetate (100 mL) was added to the reaction mixture and washed with deionized water (20 mL) and brine (2×20 mL). The organic layer was dried ($Na_2SO_4$), filtered, and concentrated in vacuo. The resulting crude purified by reverse phase HPLC (C18 column, acetonitrile-$H_2O$ with 0.1% TFA as eluent) to give the title compound as a brown solid (0.032 g, 0.070 mmol, 70%). $^1$H NMR (400 MHz, $CD_3OD$) δ 8.80 (d, J=3.2 Hz, 1H), 7.53 (dd, J=1.2, 8.4 Hz, 1H), 7.45 (dd, J=4.0, 8.4 Hz, 1H), 7.40 (t, J=8.0 Hz, 1H), 7.32 (dd, J=2.0, 8.4 Hz, 1H), 7.22 (dd, J=2.0, 12.0 Hz, 1H), 7.08 (s, 2H), 6.12 (s, 1H), 2.28 (s, 3H), 1.41 (s, 9H); MS: (ES) m/z calculated for $C_{23}H_{25}FN_5O_2S$ [M+H]$^+$ 454.2, found 454.2.

Example 31: Synthesis of N-(1-(2-aminoquinolin-5-yl)-3-methyl-1H-pyrazol-5-yl)-4-t-butylbenzenesulfonamide

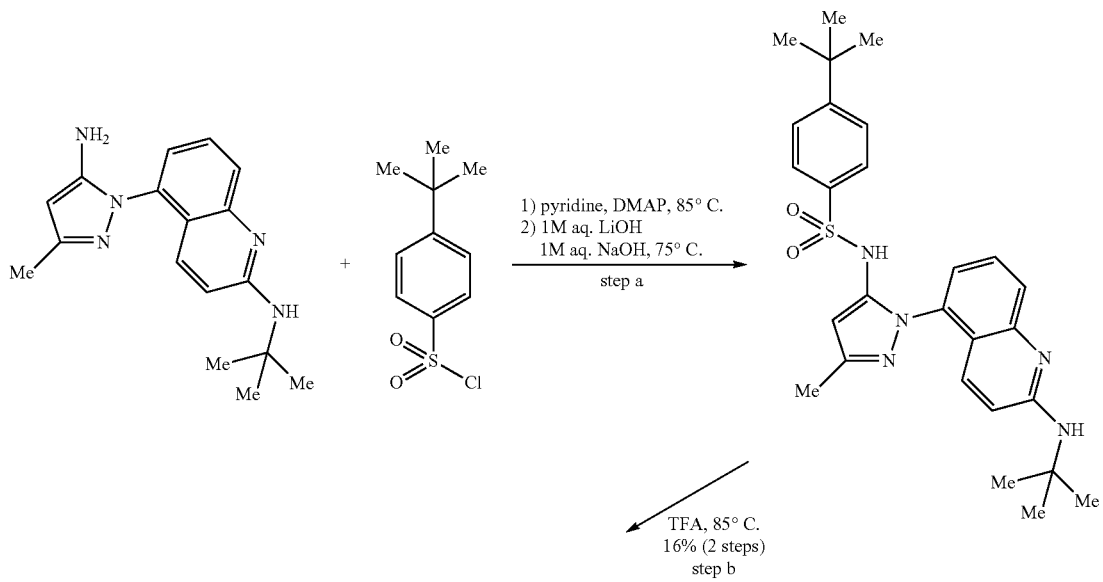

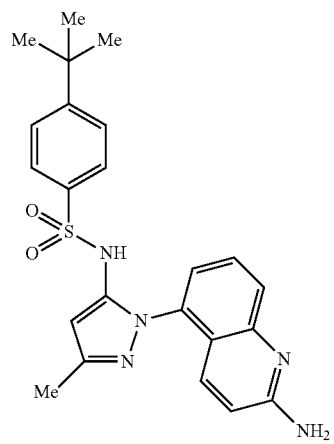

a) A mixture of crude 5-(5-amino-3-methyl-1H-pyrazol-1-yl)-N-t-butylquinoline-2-amine (prepared from Example 28 step c, 0.090 g, 0.31 mmol), 4-t-butylbenzenesulfonyl chloride (0.15 g, 0.65 mmol), and DMAP (0.022 g, 0.18 mmol) in pyridine (3 mL) was heated at 85° C. for 2 h with stirring. After cooling to room temperature, 1 M aqueous lithium hydroxide (1 mL) and 1 M aqueous sodium hydroxide (1 mL) were added to the reaction mixture and heated at 75° C. for 1 h. After cooling to room temperature, the reaction mixture was neutralized with 1 N aqueous hydrochloric acid. The aqueous layer was extracted with ethyl acetate and the organic layer was washed with aqueous saturated sodium bicarbonate, dried (Na$_2$SO$_4$), filtered, and concentrated in vacuo. The crude material was used directly to the next step.

b) The crude residue was dissolved in TFA (8 mL) and heated at 85° C. for 6 h with stirring. After cooling to room temperature, the reaction mixture was concentrated in vacuo. The crude product was then suspended in aqueous saturated sodium bicarbonate and extracted with ethyl acetate. The organic layer was dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.021 g, 0.048 mmol, 16% for 2 steps). $^1$H NMR (400 MHz, CD$_3$OD) 7.55 (d, J=6.4 Hz, 1H), 7.55-7.54 (m, 2H), 7.49 (dd, J=7.2, 8.4 Hz, 1H), 7.43 (d, J=2.0 Hz, 1H), 7.41 (s, 1H), 7.28 (d, J=9.2 Hz, 1H), 6.90 (d, J=7.2 Hz, 1H), 6.71 (d, J=9.2 Hz, 1H), 5.93 (s, 1H), 2.21 (s, 3H), 1.35 (s, 9H); MS: (ES) m/z calculated for C$_{23}$H$_{26}$N$_5$O$_2$S [M+H]$^+$ 436.2, found 436.3.

Example 32: Synthesis of 4-t-butyl-N-(3-(fluoromethyl)-1-(quinolin-5-yl)-1H-pyrazol-5-yl)benzenesulfonamide

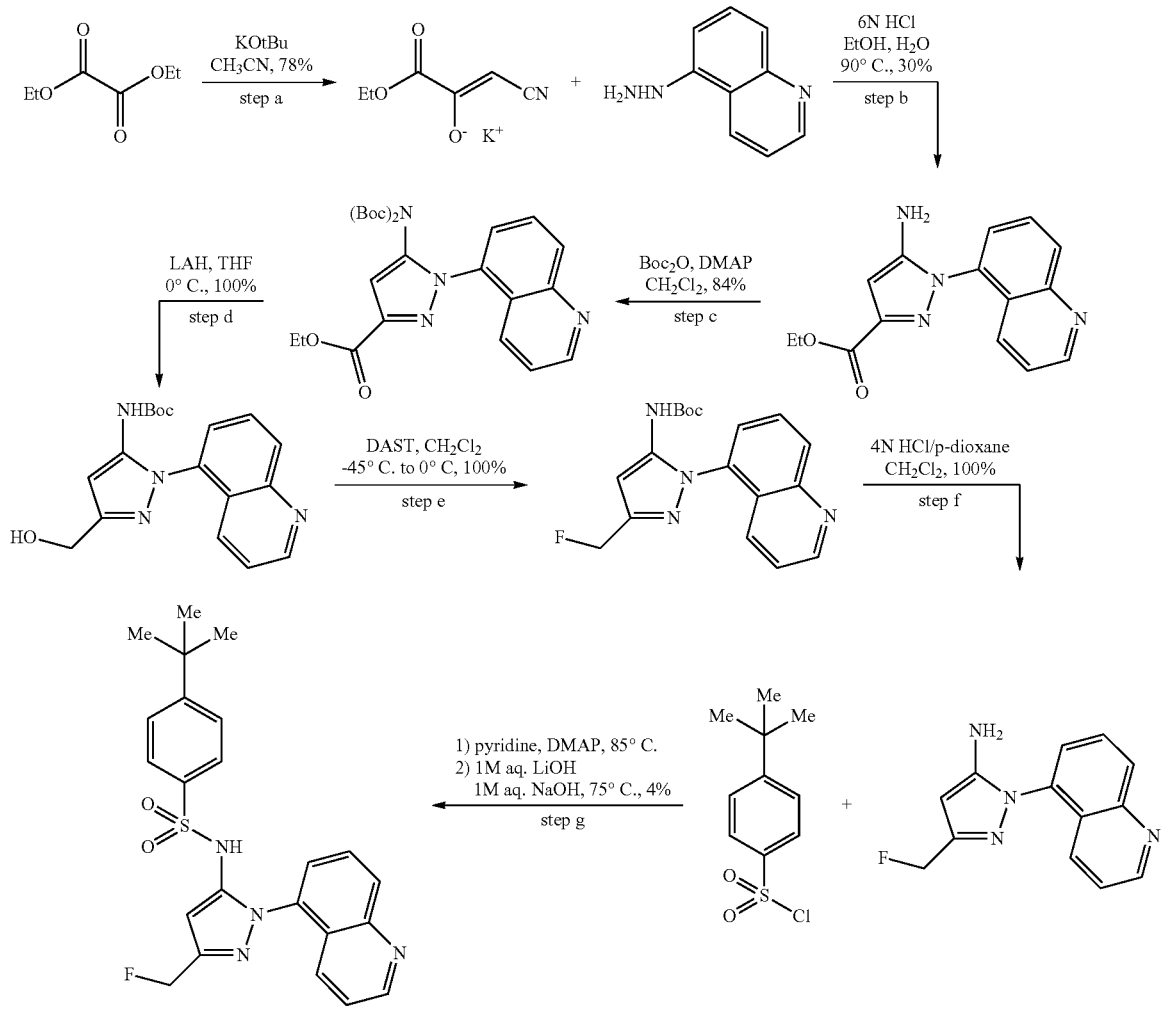

a) To a solution of diethyl oxalate (25.3 g, 173 mmol) in acetonitrile (100 mL) was added potassium t-butoxide (19.5 g, 173 mmol) over three portions. The orange suspension was stirred at room temperature for 1.5 h and the solid was collected by filtration to give a yellow powder as the desired product (24.3 g, 135.8 mmol, 78%).

b) To a stirring suspension of crude 5-hydrazinylisoquinoline (prepared from Example 25 step a, 6.0 g, 37.7 mmol) and potassium 1-cyano-3-ethoxy-3-oxoprop-1-en-2-olate (8.1 g, 45.2 mmol) in ethanol (36 mL) was added a solution of 6 N aqueous hydrochloric acid (7.7 mL, 45.2 mmol) and deionized water (10 mL). The reaction mixture was heated at 90° C. for 5 h. After cooling to room temperature, the reaction mixture was concentrated in vacuo and the resulting residue was extracted with 2:1 chloroform/iPrOH. The organic layer was washed with aqueous saturated sodium bicarbonate and the organic layer was dried ($Na_2SO_4$), filtered, and concentrated in vacuo. The resulting solid was suspended in dichloromethane/diethyl ether and the yellow solid was collected by filtration to give the desired product (3.14 g, 11.1 mmol, 30%).

c) To a solution of ethyl 5-amino-1-(quinolin-5-yl)-1H-pyrazole-3-carboxylate (0.25 g, 0.89 mmol) in dichloromethane (5 mL) was added DMAP (0.15 g, 1.2 mmol) and $Boc_2O$ (0.5 g, 2.3 mmol). The reaction mixture was stirred at room temperature for 6 h and ethyl acetate was added. The resulting solution was washed with aqueous saturated sodium bicarbonate and brine. The organic layer was dried ($Na_2SO_4$), filtered, and concentrated in vacuo. The crude product was purified by flash chromatography ($SiO_2$, 20-50% ethyl acetate in hexanes) to afford the desired product (0.36 g, 0.75 mmol, 84%).

d) To a solution of ethyl 5-(bis(t-butoxycarbonyl)amino)-1-(quinolin-5-yl)-1H-pyrazole-3-carboxylate (0.20 g, 0.41 mmol) in THF (6 mL) at 0° C. was added a solution of lithium aluminum hydride (LAH, 2.0 M solution in THF, 0.48 mL, 0.96 mmol). The reaction mixture was stirred at 0° C. for 5 min and aqueous saturated potassium sodium tartrate was added to the reaction mixture. The resulting solution was extracted with ethyl acetate (2×5 mL). The combined organic layers were dried ($Na_2SO_4$), filtered, and concentrated in vacuo to give the mono-protected crude product (0.14 g, 0.41 mmol, 100%).

e) To a stirring solution of t-butyl 3-(hydroxymethyl)-1-(quinolin-5-yl)-1H-pyrazol-5-ylcarbamate (0.20 g, 0.59 mmol) in dichloromethane (6 mL) at −45° C. was added N,N-diethylaminosulfur trifluoride (DAST, 0.15 mL, 1.2 mmol) dropwise, and the reaction mixture was stirred at 0° C. for 15 min. The reaction mixture was then poured into ice and aqueous sodium bicarbonate was added. The aqueous layer was extracted with ethyl acetate and the organic layer was dried ($Na_2SO_4$), filtered, and concentrated in vacuo. The resulting crude residue was used without further purification (0.20 g, 0.59 mmol, 100%).

f) To a stirring solution of t-butyl 3-(fluoromethyl)-1-(quinolin-5-yl)-1H-pyrazol-5-ylcarbamate (0.20 g, 0.59 mmol) in dichloromethane (5 mL) and methanol (1 mL) was added a solution of hydrochloric acid in p-dioxane (4 N solution in p-dioxane, 10 mL, 40 mmol). The reaction mixture was stirred at room temperature for 1 h and the organic volatile was removed in vacuo. The resulting residue was dissolved in 2:1 chloromethane/iPrOH and washed with aqueous 1 M sodium hydroxide and aqueous saturated sodium bicarbonate. The organic layer was dried ($Na_2SO_4$), filtered, and concentrated in vacuo. The crude residue was used without further purification (0.14 g, 0.59 mmol, 100%).

g) To a mixture of 4-t-butylbenzenesulfonyl chloride (0.085 g, 0.37 mmol), 3-(fluoromethyl)-1-(quinolin-5-yl)-1H-pyrazol-5-amine (0.05 g, 0.21 mmol), and DMAP (0.025 g, 0.19 mmol) in pyridine (1.0 mL) was heated at 85° C. for 2 h with stirring. After cooling to room temperature, 1 M aqueous lithium hydroxide (1 mL) and 1 M aqueous sodium hydroxide (1 mL) were added to the reaction mixture and heated at 75° C. for 1 h. After cooling to room temperature, the reaction mixture was neutralized with 1 N aqueous hydrochloric acid. The aqueous layer was extracted with ethyl acetate and the organic layer was washed with aqueous saturated sodium bicarbonate, dried ($Na_2SO_4$), filtered, and concentrated in vacuo. The crude residue was purified by reverse phase HPLC (C18 column, acetonitrile-$H_2O$ with 0.1% TFA as eluent) to give the title compound as a white solid (0.004 g, 0.009 mmol, 4%). $^1$H NMR (400 MHz, $CD_3OD$) δ 8.86 (dd, J=1.2, 4.0 Hz, 1H), 8.12 (d, J=8.8 Hz, 1H), 7.79 (dd, J=8.4, 8.4 Hz, 1H), 7.65 (d, J=8.4 Hz, 1H), 7.56 (s, 1H), 7.54 (s, 1H), 7.43-7.37 (m, 4H), 6.24 (s, 1H), 5.34 (s, 1H), 5.22 (s, 1H), 1.35 (s, 9H); MS: (ES) m/z calculated for $C_{23}H_{24}FN_4O_2S$ [M+H]$^+$ 439.2, found 439.1.

Example 33: Synthesis of 4-t-butyl-3-fluoro-N-(3-(fluoromethyl)-1-(quinolin-5-yl)-1H-pyrazol-5-yl)benzenesulfonamide

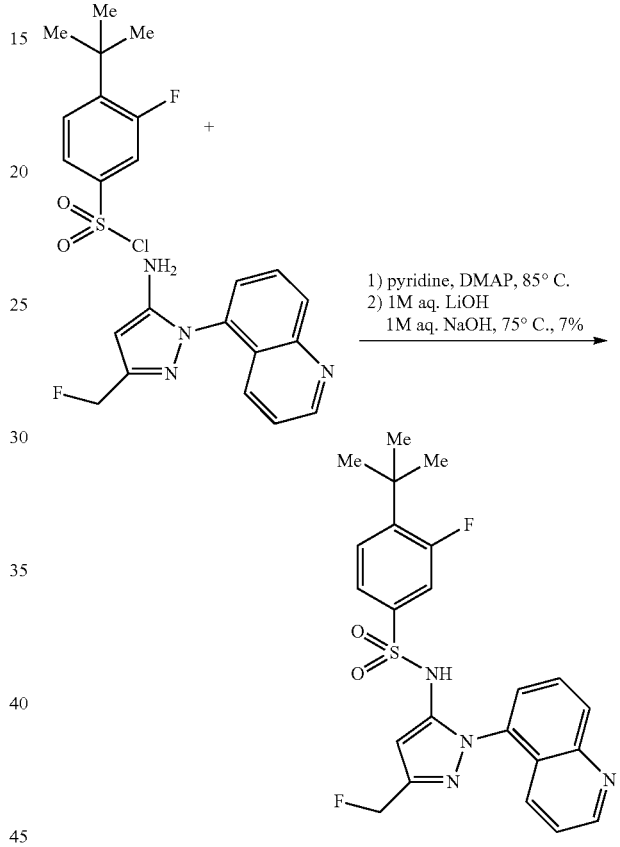

To a mixture of 4-t-butyl-3-fluorobenzene-1-sulfonyl chloride (prepared from Example 27 step c, 0.050 g, 0.20 mmol), 3-(fluoromethyl)-1-(quinolin-5-yl)-1H-pyrazol-5-amine (0.025 g, 0.10 mmol), and DMAP (0.012 g, 0.095 mmol) in pyridine (3 mL) was heated at 85° C. for 2 h with stirring. After cooling to room temperature, 1 M aqueous lithium hydroxide (1 mL) and 1 M aqueous sodium hydroxide (1 mL) were added to the reaction mixture and heated at 75° C. for 1 h. After cooling to room temperature, the reaction mixture was neutralized with 1 N aqueous hydrochloric acid. The aqueous layer was extracted with ethyl acetate and the organic layer was washed with aqueous saturated sodium bicarbonate, dried ($Na_2SO_4$), filtered, and concentrated in vacuo. The crude residue was purified by reverse phase HPLC (C18 column, acetonitrile-$H_2O$ with 0.1% TFA as eluent) to give the title compound as a white solid (0.003 g, 0.007 mmol, 7%). $^1$H NMR (400 MHz, $CD_3OD$) 8.83 (dd, J=4.4, 11.6 Hz, 1H), 8.10 (dd, J=1.2, 8.8 Hz, 1H), 7.83 (ddd, J=1.6, 7.6, 8.8 Hz, 1H), 7.63 (dd, J=0.8, 8.8 Hz, 1H), 7.53 (dd, J=0.8, 7.6 Hz, 1H), 7.41 (dd, J=1.6, 8.4 Hz, 1H), 7.38-7.31 (m, 2H), 7.24 (dd, J=1.6, 12.4 Hz, 1H), 6.05 (d, J=1.6 Hz, 1H), 5.28 (s, 1H), 5.16 (s, 1H), 1.40 (d, J=0.8 Hz, 9H); MS: (ES) m/z calculated for $C_{23}H_{26}N_5O_2S$ [M+H]$^+$ 457.2, found 457.2.

Measuring Efficacy of Chemokine Modulators

In Vitro Assays

A variety of assays can be used to evaluate the compounds provided herein, including signaling assays, chemotaxis (migration assays), ligand binding assays, and other assays of cellular response. Chemokine receptor signaling assays can be used to measure the ability of a compound, such as a potential CCR(9) antagonist, to block CCR(9) ligand- (e.g. TECK)-induced signaling. Blocking such signaling can be useful in treating various diseases such as inflammatory bowel diseases, an allergic disease, psoriasis, atopic dermatitis, asthma, fibrotic diseases, graft rejection, immune mediated food allergies, autoimmune diseases, Celiac disease, rheumatoid arthritis, thymoma, thymic carcinoma, leukemia, solid tumor, acute lymphocytic leukemia, melanoma, primary sclerosing cholangitis, hepatitis, inflammatory hepatic disease, or post-operative ileus. A chemotaxis assay can be used to measure the ability of a compound of interest, such as a possible chemokine antagonist, to block chemokine-mediated cell migration in vitro. The latter is believed to resemble chemokine-induced cell migration in vivo. A ligand binding assay can also be used to measure the ability of a compound, such as a potential CCR(9) antagonist, to block the interaction of TECK or other CCR(9) ligands with their receptor.

In a suitable assay, a chemokine protein (whether isolated or recombinant) or other ligand is used that has at least one property, activity, or functional characteristic of a mammalian chemokine protein. The property can be a binding property (to, for example, a ligand or inhibitor), a signaling activity (e.g., activation of a mammalian G protein, induction of rapid and transient increase in the concentration of cytosolic free calcium ion), cellular response function (e.g., stimulation of chemotaxis or inflammatory mediator release by leukocytes), and the like.

The assay can be a cell-based assay that utilizes cells stably or transiently transfected with a vector or expression cassette having a nucleic acid sequence that encodes the chemokine receptor. Cell lines or isolated primary cells naturally expressing the chemokine can also be used. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TECK) as a competitor.

Binding inhibition assays can be used to evaluate the present compounds. In these assays, the compounds are evaluated as inhibitors of ligand binding using, for example, TECK or small molecule ligands. The CCR(9) receptor is contacted with a ligand in the presence or absence of a test agent, and a measure of ligand binding is made. A reduction in the extent of ligand binding is indicative of inhibition of binding by the test agent. The binding inhibition assays can be carried out using whole cells which express the receptor, or a membrane fraction from cells which express the receptor.

Further, the binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., Cell, 72:415425 (1993); Van Riper et al., J. Exp. Med., 177:851-856 (1993) and Dahinden et al., J. Exp. Med., 179:751-756 (1994)). Calcium signaling assays also measure GPCR activity, by measuring intra-cellular calcium concentration over time, preferably before and after receptor/ligand binding in the presence or absence of a test agent. These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between a chemokine receptor and a known chemokine ligand, chemokine receptor-expressing cells (CCR(9)-expressing cells such as T cell line MOLT-4 cells) are first incubated with a compound of interest, such as a potential chemokine antagonist, at increasing concentrations. The cell number can be from $10^5$ to $5\times10^6$ cells per well in a 96-well microtiter plate. The concentration of the compound being tested may range from 0 to 100 µM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the chemokine ligand (TECK for CCR(9)) at 5-100 nM final concentration, and the signal of intracellular calcium increase (also called calcium flux) is recorded. The efficacy of a compound as an inhibitor of binding between the chemokine and the ligand can be calculated as an IC50 (the concentration needed to cause 50% inhibition in signaling) or IC90 (at 90% inhibition).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer et al., WO 94/20142; Berman et al., Immunol. Invest., 17:625-677 (1988); and Kavanaugh et al., J. Immunol., 146:4149-4156 (1991)).

In vitro cell chemotaxis assays can be performed (but are not limited to this format) using the 96-well microchamber (called ChemoTX™). The ChemoTX™ system is well known to those skilled in the art as a type of chemotactic/cell migration instrument. In this assay, CCR(9)-expressing cells (such as MOLT-4) are first incubated with a compound of interest, such as a possible CCR(9) antagonist at increasing concentrations. Typically, fifty thousand cells per well are used, but the amount can range from $10^3$-$10^6$ cells per well. The chemokine ligand (for example, CCR(9) ligand TECK, typically at 50 nM (but can range from 5-100 nM)), is placed at the lower chamber and the migration apparatus is assembled. Twenty microliters of test compound-treated cells are then placed onto the membrane. Migration is allowed to take place at 37° C. for a period of time, typically 2.5 hours for CCR(9). At the end of the incubation, the number of cells that migrated across the membrane into the lower chamber is then quantified. The efficacy of a compound as an inhibitor of chemokine-mediated cell migration can be calculated as an $IC_{50}$ (the concentration needed to reduce cell migration by 50%) or $IC_{90}$ (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR(9) is expressed on gut-homing T cells in peripheral blood, elevated in patients with small bowel inflammation such as Crohn's disease and Coeliac disease. CCR(9) ligand TECK is expressed in the small intestine. It is thus believed that this ligand-receptor pair plays a role in IBD development by mediating migration of T cells to the intestine. Several animal models exist and can be used for evaluating compounds of interest, such as potential CCR(9) antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala et al., *J Immunol.*, 161(10):5733-44 (1998)) involves genetic deletion of the murine multi-drug resistant gene (MDR). MDR knockout mice (MDR–/–) are susceptible to developing a severe, spontaneous intestinal inflammation when maintained under specific pathogen-free facility conditions. The intestinal inflammation seen in MDR–/– mice has a pathology similar to that of human inflammatory bowel disease (IBD) and is defined by Th1 type T cells infiltration into the lamina propria of the large intestine.

Another murine model was described by Davidson et al., *J Exp Med.*, 184(1):241-51(1986). In this model, the murine IL-10 gene was deleted and mice rendered deficient in the production of interleukin 10 (IL-10–/–). These mice develop a chronic inflammatory bowel disease (IBD) that predominates in the colon and shares histopathological features with human IBD.

Another murine model for IBD has been described by Powrie et al., *Int. Immunol.*, 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

The TNF ARE(–/–) Model.

The role of TNF in Crohn's disease in human has been demonstrated more recently by success of treatment using anti-TNF alpha antibody by Targan et al., *N. Engl. J Med.*, 337(15):1029-35 (1997). Mice with aberrant production of TNF-alpha due to genetic alteration in the TNF gene (ARE–/–) develop Crohn's-like inflammatory bowel diseases (see Kontoyiannis et al., *Immunity*, 10(3):387-98 (1999)).

The SAMP/Yit Model.

This model is described by Kosiewicz et al., *J Clin. Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Examples of In Vitro Assays

Reagents

MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine proteins TECK was obtained from R&D Systems (Minneapolis, Minn.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Evaluation of a Test Modulator in a Calcium Mobilization Assay

A cytoplasmic calcium mobilization assay was used to determine the efficacy of potential receptor antagonists at blocking the signals mediated through chemokine receptors, such as CCR(9). This assay was routinely performed using the Fluorescent Imaging Plate Reader (FLIPR, Molecular Devices). MOLT-4 cells were labeled with the fluorescent-indicator dye Fluo-4 (Molecular Devices) according to the manufacturer's directions. After labeling, the cells were collected by centrifugation (400×g for 5 min at room temperature) and resuspended in HBSS to a cell density of $2.5 \times 10^6$ cells/mL. Test compounds were prepared in 100% DMSO at 100× the final concentration; generally, a range of concentrations of each compound were tested, with final concentrations from 0.1 nM to 10,000 nM. Labeled cells (300 µL) were mixed with compound or an equal volume of DMSO (3 µL) in a 96-well plate; after thorough mixing, 50 µL of this cell/compound mixture was added to each of four wells of a 384-well FLIPR plate. The chemokine agonist (i.e., hTECK), prepared in HBSS at a 5× concentration of the previously determined $EC^{50}$ concentration, was added to each well and resulting changes in the fluorescent intensity, indicative of chemokine receptor-mediated signaling, were recorded on the FLIPR. The compound $IC^{50}$ values were calculated with these data using Graphpad Prism software (Graphpad Software) and a nonlinear regression, one-site competition model.

Evaluation of a Test Modulator in a Serum Chemotaxis Assay

A serum chemotaxis assay was used to determine the efficacy of potential receptor antagonists at blocking the migration mediated through chemokine receptors, such as CCR(9). This assay was performed using the ChemoTX® microchamber system with a 5-µm pore-sized polycarbonate membrane. MOLT-4 cells were collected by centrifugation at 400×g at room temperature, then suspended at 50 million/ml in human serum, containing 50 mM HEPES (final pH of 7.2). The compound being tested or an equivalent volume of its solvent (DMSO) was then added to the cell/serum mixture at a final DMSO concentration of 0.125% (v/v), and this mixture was then incubated together at 37° C. for one hour. Separately, recombinant human TECK was diluted with chemotaxis buffer (HBSS+0.1% BSA), generally spanning a range from 0.1 nM to 500 nM, after which 29 µl of diluted chemokine was placed in the lower wells of the ChemoTX® plate. The 5-µm (pore size) polycarbonate membrane was placed onto the plate, and 20 µL of the cell/compound mixture was transferred onto each well of the membrane. The plates were incubated at 37° C. for 90 minutes, after which the polycarbonate membranes were removed and 5 µl of the DNA-intercalating agent CyQUANT (Invitrogen, Carlsbad, Calif.) was added to the lower wells. The amount of fluorescence, corresponding to the number of migrated cells, was measured using a Spectrafluor Plus plate reader (TECAN, San Jose, Calif.).

The A2 values were calculated from the following equation, comparing the efficacy of the test compound with that of the DMSO-only control at equi-active chemokine levels:

$$\mathrm{Log}(A2) = \log[\mathrm{drug}(M)] - \log[(A'/A) - 1]$$

where A reflects the potency of the agonist in the absence of antagonist and A' reflects the potency of the agonist in the presence of antagonist at a given concentration of drug ([drug(M)]).

Examples of In Vivo Efficacy Assays

Evaluation of a Test Modulator in a CCR(9) Dependent T Cell Trafficking Model

Single cell suspensions were prepared from spleens and lymph nodes of OT-I Tg CD45.1 mice. $15 \times 10^6$ total cells (about $3 \times 10^6$ CD8 T cells) were injected into sex-matched congenic CD45.2 C57BL/6n mice (8-10 weeks old). 24 hours later, animals were immunized via oral gavage with 25 mg Ovalbumin protein (Sigma-Aldrich, St. Louis, Mo.)+10 ug Cholera Toxin (Calbiochem, San Diego, Calif.). CCR(9) antagonists were administered prior to oral ovalbumin in a time frame dictated by their mouse pharmacokinetics and dosed throughout. Five days post immunization, animals were euthanized, and small intestines were harvested. Peyer's patches were removed and, after flushing with PBS, the gut was opened on a wet square of Optima fabric (Allegiance Healthcare). The mucosa was scraped with a scalpel and then dissociated by stirring in 50 ml of medium containing 10% newborn calf serum and DTT (1 mM) for 15 min at room temperature. After centrifugation, pellets were resuspended in PBS containing 10% newborn calf serum, vortexed for 3 min, and rapidly passed through a glass wool column (1.6 g packed in a 20-ml syringe; Fisher Scientific). IEL were further purified on a Ficoll-Paque gradient and stained with mAbs for flow cytometry analysis. Transferred OT-1 Tg CD45.1 T cells were detected and quantified by flow cytometry. In this model treatment with a compound of the invention resulted in a significant reduction in the frequency of OT-1 Tg CD45.1 T cells that traffic to the small intestine in response to antigen.

Evaluation of a Test Modulator in a Cell Transfer Model of Colitis

Single cell suspensions of purified CD4+ CD25− T cells were generated from the spleen and lymph nodes of Balb/c mice. $1 \times 106$ CD4+ CD25− T cell were then transferred into sex and age-matched CB17 SCID mice. CD4+ CD25− recipient mice received either vehicle or a compound of the invention starting 2 hrs prior to the transfer. Mice body weights were monitored weekly, as mice develop disease they lose weight. Mice in which the disease progression has been slowed or inhibited will have a marked difference in their body weight relative to mice receiving vehicle. At the end of the study the colons of the mice are weighed and measured in order to assess the remodeling of the target tissue. Changes in cytokines were also measured in colonic tissue homogenates. Treatment with a compound of the invention results in significant protection from the wasting associated with disease as well as a normalization of the colonic remodeling and proinflammatory cytokine levels.

Evaluation of a Test Modulator in a Model of Inhibition of HIV Spread

In the bone marrow/liver/thymus, or "BLT" mouse, non-obese diabetic (NOD)/SCID mice (which lack endogenous T and B cells) are surgically implanted with fetal thymic and liver organoids, as in the SCID-hu system. The mice are then sublethally irradiated and transplanted with autologous $CD34^+$ stem cells obtained from fetal liver which take up residence in the murine bone marrow, effectively receiving a human bone marrow transplant and resulting in a range of human cells in peripheral blood, including mature T and B lymphocytes, monocytes, macrophages, and dendritic cells, all of which show extensive infiltration of organs and tissues including liver, lung, and gastrointestinal tract. Following transplantation, a compound of the invention is administered to transplanted mice to inhibit the trafficking of human cells to the gastrointestinal tract, a major source of T cell/HIV interaction. Compound efficacy is measured as a reduction in blood viral load by standard techniques.

Evaluation of a Test Modulator in a Model of Arthritis

A 17-day study of type II collagen-induced arthritis is conducted to evaluate the effects of a modulator on arthritis-induced clinical ankle swelling. Rat collagen-induced arthritis is an experimental model of polyarthritis that has been widely used for preclinical testing of numerous anti-arthritic agents (see Trentham et al., *J. Exp. Med.* 146(3):857-868 (1977), Bendele et al., *Toxicologic Pathol.* 27:134-142 (1999), Bendele et al., *Arthritis. Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. The test modulator is dosed daily by sub-cutaneous injection from day 9 to day 17 at a dose of 100 mg/kg and a volume of 1 mL/kg in the following vehicle (24.5% Cremaphore EL, 24.5% common oil, 1% Benzylalcohol and 50% Distilled water). Caliper measurements of the ankle joint diameter are taken daily, and reducing joint swelling is taken as a measure of efficacy.

Evaluation of a Test Modulator in a Model of Ulcerative Colitis

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, a CCR(9) antagonist of the invention was evaluated by prophylactic administration for its ability to delay disease onset. Female mice (n=34) were dosed with 10-100 mg/kg once a day by subcutaneous injections for 14 consecutive weeks starting at age 10 weeks. The study was evaluated for IBD-associated growth retardation, and the tested compound was shown to be efficacious in this model.

Evaluation of a Test Modulator in a Mouse Model of Asthma

This example describes a procedure to evaluate the efficacy of antagonists for treatment of asthma. An animal model of asthma can be induced by sensitizing rodents to an experimental antigen (e.g. OVA) by standard immunization, and subsequently introducing that same antigen into the rodents lung by aerosolization. Three series of rodent groups, comprising 10 rodents per group, are actively sensitized on Day 0 by a single i.p. injection with 100 ug OVA in phosphate-buffered saline (PBS), along with an adjuvant e.g. aluminum hydroxide. At 11 days after sensitization, the animals are placed in a Plexiglas chamber and challenged with aerosolized OVA (1%) for 30 minutes using the ultrasonic nebulizer (De Vilbliss). One series of mice additionally receives PBS and Tween 0.5% i.p. at the initial sensitization, and at different dosing schedules thereafter, up until the aerosolized OVA challenge. A second series consists of groups of mice receiving different doses of the CCR4 antagonist given either intraperitoneally, intra-venously, sub-cutaneously, intra-muscularly, orally, or via any other mode of administration at the initial sensitization, and at different dosing schedules thereafter, up until the aerosolized OVA challenge. A third series of mice, serving as positive control, consists of groups treated with either mouse IL-10 i.p., anti-IL4 antibodies i.p., or anti-IL5 antibodies i.p. at the initial sensitization, and at different dosing schedules thereafter, up until the aerosolized OV A challenge. Animals are subsequently analyzed at different time points after the aerosolized OVA challenge for pulmonary function, cellular infiltrates in bronchoalveolar lavage (BAL), histological examination of lungs, and measurement of serum OVA specific IgE titers.

It is therefore intended that the foregoing detailed description be regarded as illustrative rather than limiting, and that it be understood that it is the following claims, including all equivalents, that are intended to define the spirit and scope of this invention.

The invention claimed is:
1. A compound or salt thereof of formula (II):

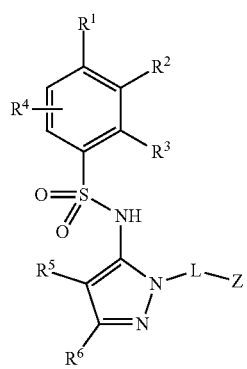

(II)

wherein:
R$^1$ is selected from the group consisting of substituted or unsubstituted C$_{2-8}$ alkyl, substituted or unsubstituted C$_{1-8}$ alkoxy, unsubstituted C$_{1-8}$ alkylamino, and substituted or unsubstituted C$_{3-10}$ heterocyclyl; and R$^2$ is H, F, Cl, or substituted or unsubstituted C$_{1-8}$ alkoxy; or R$^1$ and R$^2$ together with the carbon atoms to which they are attached form a non-aromatic carbocyclic ring or a heterocyclic ring;

R$^3$ is H, substituted or unsubstituted C$_{1-8}$ alkyl, substituted or unsubstituted C$_{1-8}$ alkoxy, or halo;

R$^4$ is H or F;

R$^5$ is H, F, Cl, or —CH$_3$; and

R$^6$ is H, halo, —CN, —CO$_2$R$^a$, —CONH$_2$, —NH$_2$, unsubstituted C$_{1-8}$ aminoalkyl, substituted or unsubstituted C$_{1-8}$ alkyl, or substituted or unsubstituted C$_{1-8}$ alkoxy, wherein R$^a$ is H or substituted or unsubstituted C$_{1-8}$ alkyl; or R$^5$ and R$^6$ together with the carbon atoms to which they are attached form a carbocyclic ring;

L is a bond, —CH$_2$—, or —CH(CH$_3$)—;

Z is selected from the group consisting of

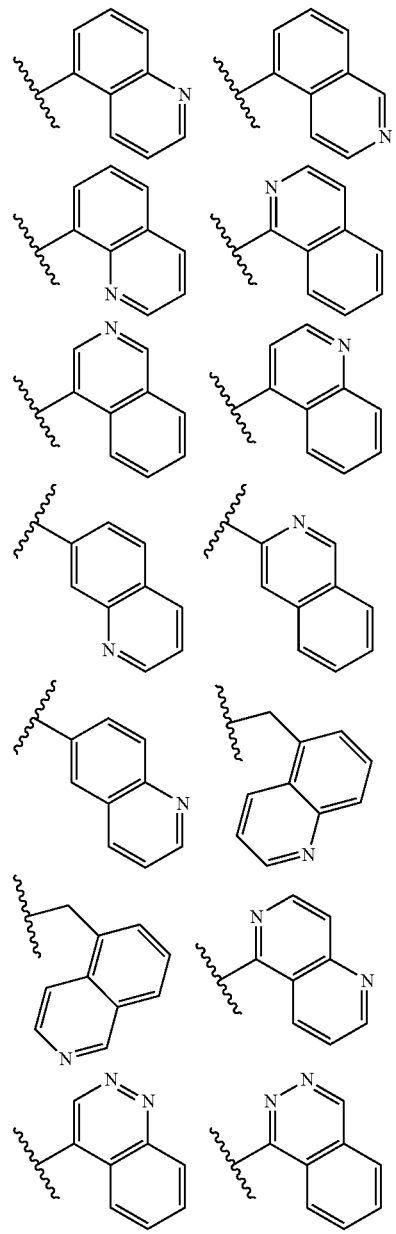

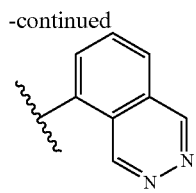

and N-oxides thereof;
the Z group is unsubstituted or substituted with 1 to 3 independently selected $R^8$ substituents;
each $R^8$ is independently selected from the group consisting of H, halo, —CN, —OH, oxo, substituted or unsubstituted $C_{1-8}$ alkyl, substituted or unsubstituted $C_{1-8}$ alkoxy, —$NR^{20}R^{21}$, substituted or unsubstituted aryl, substituted or unsubstituted heteroaryl, and substituted or unsubstituted heterocyclyl;
$R^{20}$ and $R^{21}$ are each independently H or substituted or unsubstituted $C_{1-8}$ alkyl,
wherein substituents for substituted alkyl including the alkyl portions of aminoalkyl, alkylamino, and alkoxy are independently selected from: halogen, —CN, —CO₂R', —C(O)R', —C(O)NR'R", oxo (═O or —O⁻), —OR', —OC(O)R', —OC(O)NR'R", —NO₂, —NR'C(O)R", —NR'''C(O)NR'R", —NR'R", —NR'CO₂R", —NR'S(O)R''', —NR'S(O)₂R''', —NR'''S(O)NR'R", —NR'''S(O)₂NR'R", —SR', —S(O)R', —S(O)₂R', —S(O)₂NR'R", —NR'—C(NHR")═NR''', —SiR'R"R''', —OSiR'R"R''', —N₃, unsubstituted $C_{6-10}$ aryl, unsubstituted 5- to 10-membered heteroaryl, and unsubstituted 3- to 10-membered heterocyclyl;
wherein the number of substituents is from zero to (2m'+1), where m' is the total number of carbon atoms in the alkyl, alkenyl, and alkynyl group;
wherein substituents for substituted aryl, heterocyclyl, and heteroaryl are independently selected from halogen, —CN, —CO₂R', —C(O)R', —C(O)NR'R", oxo (═O or —O⁻), —OR', —OSiR'R"R''', —OC(O)R', —OC(O)NR'R", —NO₂, —NR'C(O)R", —NR'''C(O)NR'R", —NR'R", —NR'CO₂R", —NR'S(O)R''', —NR'S(O)₂R''', —NR'''S(O)NR'R", —NR'''S(O)₂NR'R", —SR', —S(O)R', —S(O)₂R', —S(O)₂NR'R", —NR'—C(NHR")═NR''', —SiR'R"R''', —N₃, unsubstituted $C_{1-8}$ alkyl, unsubstituted $C_{2-8}$ alkenyl, unsubstituted $C_{2-8}$ alkynyl, unsubstituted $C_{6-10}$ aryl, unsubstituted 5- to 10-membered heteroaryl, and unsubstituted 3- to 10-membered heterocyclyl;
wherein the number of possible substituents to substituted aryl, heterocyclyl, and heteroaryl is from 0 to the total number of open valences on the ring system; and
wherein R', R" and R''' are each independently hydrogen, unsubstituted $C_{1-8}$ alkyl, unsubstituted $C_{2-8}$ alkenyl, or unsubstituted $C_{2-8}$ alkynyl.

2. The compound claim 1 or salt thereof, wherein Z is

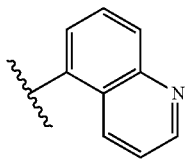 [SMILES: *c1cccc2ncccc12]

wherein the Z group is unsubstituted or substituted with 1 to 3 independently selected $R^8$ substituents.

3. The compound of claim 2 or salt thereof, wherein $R^1$ is selected from the group consisting of: —CH₂CH₃, —CH(CH₃)₂, —C(CH₃)₃, —C(CH₃)₂CH₂CH₃, —C(CH₂CH₂)CN, —C(OH)(CH₃)₂, —OCH₃, —OCH₂CH₃, —OCH(CH₃)₂, —OC(CH₃)₃, —OCH₂CH(CH₃)₂, —OCF₃, and morpholino;

$R^2$ is H, F, or Cl; or $R^3$ is H, —CH₃, or —OCH₃;

$R^4$ is H or F;

$R^5$ is H;

$R^6$ is H, —CH₃, —CH₂CH₃, —CH(CH₃)₂, —C₃H₇, —CH₂F, —CHF₂, —CF₂CH₃, —CF₃, —CH₂OCH₃, —CH₂OH, —CH₂CN, —CN, or —CONH₂; and each $R^8$ is independently selected from the group consisting of H, F, Cl, Br, —CH₃, —OH, —OCH₃, —OCH₂CH₃, —NH₂, —N(CH₃)₂, and —CN.

4. The compound of claim 2 or salt thereof, wherein $R^1$ is —C(CH₃)₃;

$R^2$ is H or F;

$R^3$ is H;

$R^4$ is H;

$R^5$ is H; and $R^6$ is —CH₃, —CH₂F, —CHF₂, or —CF₃.

5. The compound of claim 1 or salt thereof, of formula (IIIa) or (IIIb):

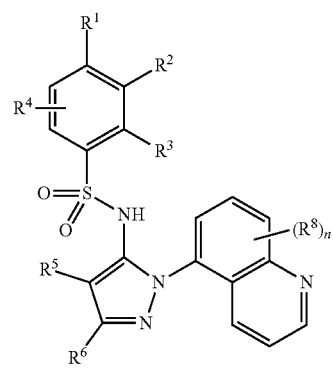

(IIIa)

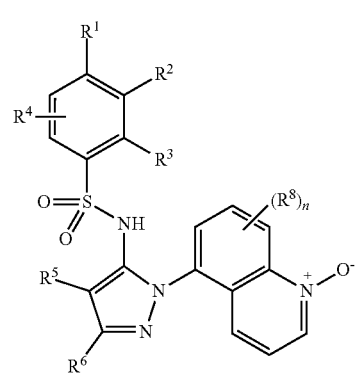

(IIIb)

wherein:
R¹ is selected from the group consisting of substituted or unsubstituted $C_{2-8}$ alkyl, substituted or unsubstituted $C_{1-8}$ alkoxy, unsubstituted $C_{1-8}$ alkylamino, and substituted or unsubstituted $C_{3-10}$ heterocyclyl; and
R² is H, F, Cl, or substituted or unsubstituted $C_{1-8}$ alkoxy; or
R¹ and R² together with the carbon atoms to which they are attached form a non-aromatic carbocyclic ring or a heterocyclic ring;
R³ is H, substituted or unsubstituted $C_{1-8}$ alkyl, substituted or unsubstituted $C_{1-8}$ alkoxy, or halo;
R⁴ is H or F;
R⁵ is H, F, Cl, or —CH₃; and
R⁶ is H, halo, —CN, —CO₂Rᵃ, —CONH₂, —NH₂, unsubstituted $C_{1-8}$ aminoalkyl, substituted or unsubstituted $C_{1-8}$ alkyl, or substituted or unsubstituted $C_{1-8}$ alkoxy, wherein Rᵃ is H or substituted or unsubstituted $C_{1-8}$ alkyl; or
R⁵ and R⁶ together with the carbon atoms to which they are attached form a carbocyclic ring;
each R⁸ is independently selected from the group consisting of H, halo, —CN, —OH, oxo, substituted or unsubstituted $C_{1-8}$ alkyl, substituted or unsubstituted $C_{1-8}$ alkoxy, —NR²⁰R²¹, substituted or unsubstituted aryl, substituted or unsubstituted heteroaryl, and substituted or unsubstituted heterocyclyl;
R²⁰ and R²¹ are each independently H or substituted or unsubstituted $C_{1-8}$ alkyl; and
n is 0, 1, 2 or 3.

6. The compound of claim 5 or salt thereof, wherein
R¹ is selected from the group consisting of: —CH₂CH₃, —CH(CH₃)₂, —C(CH₃)₃, —C(CH₃)₂CH₂CH₃, —C(CH₂CH₂)CN, —C(OH)(CH₃)₂, —OCH₃, —OCH₂CH₃, —OCH(CH₃)₂, —OC(CH₃)₃, —OCH₂CH(CH₃)₂, —OCF₃, and morpholino; and
R² is H, F, or C₁; or
R¹ and R² together form —OC(CH₃)₂CH₂— or —C(CH₃)₂CH₂CH₂—;
R³ is H, —CH₃, or —OCH₃;
R⁴ is H or F;
R⁵ is H;
R⁶ is H, —CH₃, —CH₂CH₃, —CH(CH₃)₂, —C₃H₇, —CH₂F, —CHF₂, —CF₂CH₃, —CF₃, —CH₂OCH₃, —CH₂OH, —CH₂CN, —CN, or —CONH₂; and
each R⁸ is independently selected from the group consisting of H, F, Cl, Br, —CH₃, —OH, —OCH₃, —OCH₂CH₃, —NH₂, —N(CH₃)₂, and —CN.

7. The compound of claim 5 or salt thereof, wherein R¹ is —C(CH₃)₃.

8. The compound of claim 5 or salt thereof, wherein
R² is H or F;
R³ is H;
R⁴ is H; and
R⁶ is —CH₃, —CH₂F, —CHF₂, or —CF₃.

9. A composition comprising a pharmaceutically acceptable carrier and a compound or salt of formula (I):

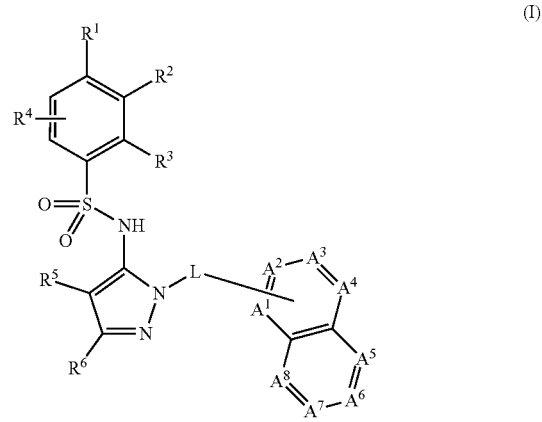

(I)

wherein:
R¹ is selected from the group consisting of substituted or unsubstituted $C_{2-8}$ alkyl, substituted or unsubstituted $C_{1-8}$ alkoxy, unsubstituted $C_{1-8}$ alkylamino, and substituted or unsubstituted $C_{3-10}$ heterocyclyl; and
R² is H, F, Cl, or substituted or unsubstituted $C_{1-8}$ alkoxy; or
R¹ and R² together with the carbon atoms to which they are attached form a non-aromatic carbocyclic ring or a heterocyclic ring;
R³ is H, substituted or unsubstituted $C_{1-8}$ alkyl, substituted or unsubstituted $C_{1-8}$ alkoxy, or halo;
R⁴ is H or F;
R⁵ is H, F, Cl, or —CH₃; and
R⁶ is H, halo, —CN, —CO₂Rᵃ, —CONH₂, —NH₂, substituted or unsubstituted $C_{1-8}$ alkyl, substituted or unsubstituted $C_{1-8}$ alkoxy, or unsubstituted $C_{1-8}$ aminoalkyl, wherein Rᵃ is H or substituted or unsubstituted $C_{1-8}$ alkyl; or
R⁵ and R⁶ together with the carbon atoms to which they are attached form a carbocyclic ring;
L is a bond, —CH₂—, or —CH(CH₃)—;
each of A¹, A², A³, A⁴, A⁵, A⁶, A⁷, and A⁸ are independently selected from the group consisting of N, N—O, and —CR⁸—; wherein at least one and not more than two of A¹, A², A³, A⁴, A⁵, A⁶, A⁷, and A⁸ are N or N—O;
R⁸ is each independently selected from the group consisting of H, halo, —CN, —OH, oxo, substituted or unsubstituted $C_{1-8}$ alkyl, substituted or unsubstituted $C_{1-8}$ alkoxy, —NR²⁰R²¹, substituted or unsubstituted aryl, substituted or unsubstituted heteroaryl, and substituted or unsubstituted heterocyclyl;
R²⁰ and R²¹ are each independently H or substituted or unsubstituted $C_{1-8}$ alkyl,
wherein substituents for substituted alkyl including the alkyl portions of aminoalkyl, alkylamino, and alkoxy are independently selected from: halogen, —CN, —CO₂R', —C(O)R', —C(O)NR'R", oxo (=O or —O—), —OR', —OC(O)R', —OC(O)NR'R", —NO₂, —NR'C(O)R", —NR'''C(O)NR'R", —NR'R", —NR'CO₂R", —NR'S(O)R", —NR'S(O)₂R''', —NR'''S(O)NR'R", —NR'''S(O)₂NR'R", —SR', —S(O)R', —S(O)₂R', —S(O)₂NR'R", —NR'—C(NHR")=NR''', —SiR'R"R''', —OSiR'R"R''', —N₃, unsubstituted C<sub>6-10</sub> aryl, unsubstituted 5- to 10-membered heteroaryl, and unsubstituted 3- to 10-membered heterocyclyl;

wherein the number of substituents is from zero to (2m'+1), where m' is the total number of carbon atoms in the alkyl, alkenyl, and alkynyl group;

wherein substituents for substituted aryl, heterocyclyl, and heteroaryl are independently selected from halogen, —CN, —CO₂R', —C(O)R', —C(O)NR'R", oxo (═O or —O⁻), —OR', —OSiR'R"R'", —OC(O)R', —OC(O)NR'R", —NO₂, —NR'C(O)R", —NR'"C(O)NR'R", —NR'R", —NR'CO₂R", —NR'S(O)R", —NR'S(O)₂R", —NR'"S(O)NR'R", —NR'"S(O)₂NR'R", —SR', —S(O)R', —S(O)₂R', —S(O)₂NR'R", —NR'—C(NHR")═NR'", —SiR'R"R'", —N₃, unsubstituted $C_{1-8}$ alkyl, unsubstituted $C_{2-8}$ alkenyl, unsubstituted $C_{2-8}$ alkynyl, unsubstituted $C_{6-10}$ aryl, unsubstituted 5- to 10-membered heteroaryl, and unsubstituted 3- to 10-membered heterocyclyl;

wherein the number of possible substituents to substituted aryl, heterocyclyl, and heteroaryl is from 0 to the total number of open valences on the ring system; and wherein R', R" and R'" are each independently hydrogen, unsubstituted $C_{1-8}$ alkyl, unsubstituted $C_{2-8}$ alkenyl, or unsubstituted $C_{2-8}$ alkynyl.

10. The composition of claim 9, wherein the compound or salt thereof is of formula (II):

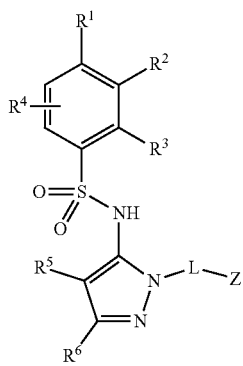

(II)

wherein:
$R^1$ is selected from the group consisting of substituted or unsubstituted $C_{2-8}$ alkyl, substituted or unsubstituted $C_{1-8}$ alkoxy, unsubstituted $C_{1-8}$ alkylamino, and substituted or unsubstituted $C_{3-10}$ heterocyclyl; and
$R^2$ is H, F, Cl, or substituted or unsubstituted $C_{1-8}$ alkoxy; or
$R^1$ and $R^2$ together with the carbon atoms to which they are attached form a non-aromatic carbocyclic ring or a heterocyclic ring;
$R^3$ is H, substituted or unsubstituted $C_{1-8}$ alkyl, substituted or unsubstituted $C_{1-8}$ alkoxy, or halo;
$R^4$ is H or F;
$R^5$ is H, F, C₁, or —CH₃;
$R^6$ is H, halo, —CN, —CO₂R$^a$, —CONH₂, —NH₂, unsubstituted $C_{1-8}$ aminoalkyl, substituted or unsubstituted $C_{1-8}$ alkyl, or substituted or unsubstituted $C_{1-8}$ alkoxy;

R$^a$ is H or substituted or unsubstituted $C_{1-8}$ alkyl;
L is a bond; and
Z is

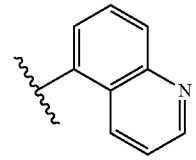

wherein the Z group is unsubstituted or substituted with 1 to 3 independently selected $R^8$ substituents;
each $R^8$ is independently selected from the group consisting of H, halo, —CN, —OH, oxo, substituted or unsubstituted $C_{1-8}$ alkyl, substituted or unsubstituted $C_{1-8}$ alkoxy, —NR²⁰R²¹, substituted or unsubstituted aryl, substituted or unsubstituted heteroaryl, and substituted or unsubstituted heterocyclyl; and
$R^{20}$ and $R^{21}$ are each independently H or substituted or unsubstituted $C_{1-8}$ alkyl.

11. A method of modulating CCR(9) function in a cell, comprising contacting the cell with a CCR(9) modulating amount of the compound of claim 1.

12. A method for treating a CCR(9)-mediated condition or disease comprising administering to a subject in need thereof a therapeutically effective amount of a compound or salt thereof of formula (I):

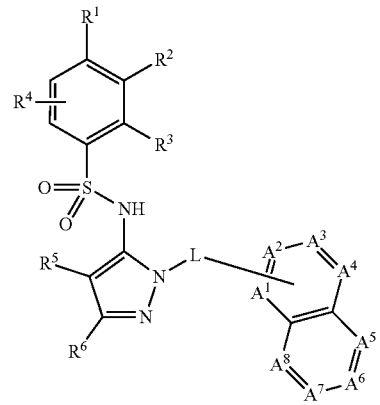

(I)

wherein:
$R^1$ is selected from the group consisting of substituted or unsubstituted $C_{2-8}$ alkyl, substituted or unsubstituted $C_{1-8}$ alkoxy, unsubstituted $C_{1-8}$ alkylamino, and substituted or unsubstituted $C_{3-10}$ heterocyclyl; and
$R^2$ is H, F, Cl, or substituted or unsubstituted $C_{1-8}$ alkoxy; or
$R^1$ and $R^2$ together with the carbon atoms to which they are attached form a non-aromatic carbocyclic ring or a heterocyclic ring;
$R^3$ is H, substituted or unsubstituted $C_{1-8}$ alkyl, substituted or unsubstituted $C_{1-8}$ alkoxy, or halo;
$R^4$ is H or F;
$R^5$ is H, F, Cl, or —CH₃; and
$R^6$ is H, halo, —CN, —CO₂R$^a$, —CONH₂, —NH₂, substituted or unsubstituted $C_{1-8}$ alkyl, substituted or unsubstituted $C_{1-8}$ alkoxy, or unsubstituted $C_{1-8}$ aminoalkyl, wherein R$^a$ is H or substituted or unsubstituted $C_{1-8}$ alkyl; or $R^5$ and $R^6$ together with the carbon atoms to which they are attached form a carbocyclic ring;

L is a bond, —$CH_2$—, or —$CH(CH_3)$—;

each of $A^1$, $A^2$, $A^3$, $A^4$, $A^5$, $A^6$, $A^7$, and $A^8$ are independently selected from the group consisting of N, N—O, and —$CR^8$—; wherein at least one and not more than two of $A^1$, $A^2$, $A^3$, $A^4$, $A^5$, $A^6$, $A^7$, and $A^8$ are N or N—O;

$R^8$ is each independently selected from the group consisting of H, halo, —CN, —OH, oxo, substituted or unsubstituted $C_{1-8}$ alkyl, substituted or unsubstituted $C_{1-8}$ alkoxy, —$NR^{20}R^{21}$, substituted or unsubstituted aryl, substituted or unsubstituted heteroaryl, and substituted or unsubstituted heterocyclyl; and $R^{20}$ and $R^{21}$ are each independently H or substituted or unsubstituted $C_{1-8}$ alkyl, wherein substituents for substituted alkyl including the alkyl portions of aminoalkyl, alkylamino, and alkoxy are independently selected from: halogen, —CN, —$CO_2R'$, —C(O)R', —C(O)NR'R'', oxo (=O or —O⁻), —OR', —OC(O)R', —OC(O)NR'R'', —$NO_2$, —NR'C(O)R'', —NR'''C(O)NR'R'', —NR'R'', —$NR'CO_2R''$, —NR'S(O)R'', —$NR'S(O)_2R''$, —NR'''S(O)NR'R'', —$NR'''S(O)_2NR'R''$, —SR', —S(O)R', —$S(O)_2R'$, —$S(O)_2NR'R''$, —NR'—C(NHR'')=NR''', —SiR'R''R''', —OSiR'R''R''', —$N_3$, unsubstituted $C_{6-10}$ aryl, unsubstituted 5- to 10-membered heteroaryl, and unsubstituted 3- to 10-membered heterocyclyl;

wherein the number of substituents is from zero to (2m'+1), where m' is the total number of carbon atoms in the alkyl, alkenyl, and alkynyl group;

wherein substituents for substituted aryl, heterocyclyl, and heteroaryl are independently selected from halogen, —CN, —$CO_2R'$, —C(O)R', —C(O)NR'R'', oxo (=O or —O⁻), —OR', —OSiR'R''R''', —OC(O)R', —OC(O)NR'R'', —$NO_2$, —NR'C(O)R'', —NR'''C(O)NR'R'', —NR'R'', —$NR'CO_2R''$, —NR'S(O)R'', —$NR'S(O)_2R''$, —NR'''S(O)NR'R'', —NR'''S(O)$_2$NR'R'', —SR', —S(O)R', —$S(O)_2R'$, —$S(O)_2NR'R''$, —NR'—C(NHR'')=NR''', —SiR'R''R''', —$N_3$, unsubstituted $C_{1-8}$ alkyl, unsubstituted $C_{2-8}$ alkenyl, unsubstituted $C_{2-8}$ alkynyl, unsubstituted $C_{6-10}$ aryl, unsubstituted 5- to 10-membered heteroaryl, and unsubstituted 3- to 10-membered heterocyclyl;

wherein the number of possible substituents to substituted aryl, heterocyclyl, and heteroaryl is from 0 to the total number of open valences on the ring system;

wherein R', R'' and R''' are each independently hydrogen, unsubstituted $C_{1-8}$ alkyl, unsubstituted $C_{2-8}$ alkenyl, or unsubstituted $C_{2-8}$ alkynyl; and wherein the CCR(9)-mediated disease or condition is selected from the group consisting of ulcerative colitis, Crohn's disease, inflammatory bowel disease, asthma, graft rejection, immune mediated food allergies, celiac disease, primary sclerosing cholangitis, and graft-v-host disease.

13. The method of claim 12, wherein the compound or salt thereof is of formula (II):

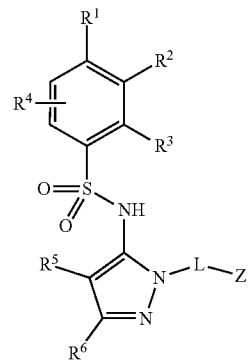

(II)

wherein:

$R^1$ is selected from the group consisting of substituted or unsubstituted $C_{2-8}$ alkyl, substituted or unsubstituted $C_{1-8}$ alkoxy, unsubstituted $C_{1-8}$ alkylamino, and substituted or unsubstituted $C_{3-10}$ heterocyclyl; and $R^2$ is H, F, Cl, or substituted or unsubstituted $C_{1-8}$ alkoxy; or $R^1$ and $R^2$ together with the carbon atoms to which they are attached form a non-aromatic carbocyclic ring or a heterocyclic ring;

$R^3$ is H, substituted or unsubstituted $C_{1-8}$ alkyl, substituted or unsubstituted $C_{1-8}$ alkoxy, or halo;

$R^4$ is H or F;

$R^5$ is H, F, Cl, or —$CH_3$;

$R^6$ is H, halo, —CN, —$CO_2R^a$, —$CONH_2$, —$NH_2$, unsubstituted $C_{1-8}$ aminoalkyl, substituted or unsubstituted $C_{1-8}$ alkyl, or substituted or unsubstituted $C_{1-8}$ alkoxy;

$R^a$ is H or substituted or unsubstituted $C_{1-8}$ alkyl;

L is a bond;

Z is

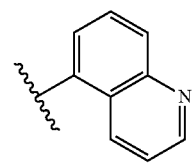 [SMILES: *c1cccc2ncccc12]

wherein the Z group is unsubstituted or substituted with 1 to 3 independently selected $R^8$ substituents;

each $R^8$ is independently selected from the group consisting of H, halo, —CN, —OH, oxo, substituted or unsubstituted $C_{1-8}$ alkyl, substituted or unsubstituted $C_{1-8}$ alkoxy, —$NR^{20}R^{21}$, substituted or unsubstituted aryl, substituted or unsubstituted heteroaryl, and substituted or unsubstituted heterocyclyl; and $R^{20}$ and $R^{21}$ are each independently H or substituted or unsubstituted $C_{1-8}$ alkyl.

14. The method of claim 12, wherein the subject is a human.

15. The method of claim 12, wherein the administering is oral, parenteral, rectal, transdermal, sublingual, nasal or topical.

16. The method of claim 12, wherein the CCR(9)-mediated disease or condition is an inflammatory bowel disease selected from Crohn's disease or ulcerative colitis.

17. The method of claim 12, wherein the CCR(9)-mediated disease or condition is asthma.

18. The method of claim 12, wherein the CCR(9)-mediated disease is graft-v-host disease.

19. The method of claim 12, further comprising administering an anti-inflammatory or analgesic agent.

* * * * *

UNITED STATES PATENT AND TRADEMARK OFFICE
CERTIFICATE OF CORRECTION

PATENT NO. : 10,596,163 B2
APPLICATION NO. : 16/170752
DATED : March 24, 2020
INVENTOR(S) : Xi Chen et al.

Page 1 of 1

It is certified that error appears in the above-identified patent and that said Letters Patent is hereby corrected as shown below:

In the Claims

In Claim 6, Column 127, Line 44, please delete "$C_1$" and insert in place thereof --Cl--
In Claim 10, Column 129, Line 63, please delete "$C_1$" and insert in place thereof --Cl--

Signed and Sealed this
Fourth Day of August, 2020

Andrei Iancu
*Director of the United States Patent and Trademark Office*